US010041082B2

(12) United States Patent
Kuhn et al.

(10) Patent No.: US 10,041,082 B2
(45) **Date of Patent: *Aug. 7, 2018**

(54) REGULATORY NUCLEIC ACID MOLECULES FOR ENHANCING SEED-SPECIFIC AND/OR SEED-PREFERENTIAL GENE EXPRESSION IN PLANTS

(71) Applicant: BASF Plant Science Company GmbH, Ludwigshafen (DE)

(72) Inventors: Josef Martin Kuhn, Ludwigshafen (DE); Linda Patricia Loyall, Limburgerhof (DE); Malte Siebert, Heidelberg (DE); Elke Duwenig, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,906

(22) Filed: Oct. 28, 2016

(65) Prior Publication Data

US 2017/0044562 A1 Feb. 16, 2017

Related U.S. Application Data

(60) Continuation of application No. 14/838,950, filed on Aug. 28, 2015, which is a division of application No. 13/393,045, filed as application No. PCT/EP2010/061661 on Aug. 11, 2010, now Pat. No. 9,150,871.

(60) Provisional application No. 61/238,233, filed on Aug. 31, 2009.

(30) Foreign Application Priority Data

Aug. 31, 2009 (EP) .................................... 09169017

(51) Int. Cl.
*C12N 15/82* (2006.01)
*C12N 5/04* (2006.01)

(52) U.S. Cl.
CPC ........... *C12N 15/8234* (2013.01); *C12N 5/04* (2013.01); *C12N 15/8216* (2013.01); *C12N 15/8241* (2013.01)

(58) Field of Classification Search
None
See application file for complete search history.

(56) References Cited

U.S. PATENT DOCUMENTS 5,750,866 A 5/1998 Dietrich et al.
8,071,383 B2 12/2011 Arias et al.
9,428,757 B2 * 8/2016 Senger ............... C12N 15/8216
9,727,757 B2 8/2017 Frosch et al.
2005/0216967 A1 9/2005 Heim et al.
2005/0246785 A1 11/2005 Cook et al.
2006/0195934 A1 8/2006 Apuya et al.
2006/0195943 A1 8/2006 Feldmann et al.
2007/0006335 A1 1/2007 Cook et al.
2007/0006345 A1 1/2007 Alexandrov et al.
2007/0006347 A1 1/2007 Plesch et al.
2009/0172837 A1 7/2009 Geiger et al.
2010/0192237 A1 7/2010 Ren et al.
2010/0199365 A1 8/2010 Senger et al.
2010/0255584 A1 * 10/2010 Yongwei ............. C07K 14/415 435/419
2011/0014706 A2 1/2011 Cao et al.
2012/0167248 A1 2/2012 Kuhn et al.
2012/0084885 A1 4/2012 Alexandrov et al.
2012/0185965 A1 7/2012 Senger et al.
2015/0052636 A1 2/2015 Hartig et al.
2015/0361440 A1 * 12/2015 Kuhn ................ C12N 15/8234 800/287

FOREIGN PATENT DOCUMENTS

CL 2007000696 A1 6/2008
EP 1645633 A2 4/2006
JP 2009/529863 A 8/2009
RU 2197527 C2 1/2003
WO WO-93/20216 A1 10/1993
WO WO-99/67389 A2 12/1999
WO WO-00/55325 A2 9/2000
WO WO-01/98480 A2 12/2001
WO WO-02/16655 A2 2/2002
WO WO-03/006660 A1 1/2003
WO WO-03/008596 A2 1/2003
WO WO-03/102198 A1 12/2003

(Continued)

OTHER PUBLICATIONS

"Transgenic plant; promoter; ds; gene silencing; RNA interference; gene expression; PT0723", Genbank Database, Accession No. AJV39144, Nov. 29, 2007.
Baeumlein, H., et al., "A Novel Seed Protein Gene from *Vicia faba* is Developmentally Regulated in Transgenic Tobacco and *Arabidopsis* Plants", Mol. Gen. Genet., vol. 225, (1991), pp. 459-467.
Bruce, W. B., et al., "cis-Acting Elements Involved in Photoregulation of an Oat Phytochrome Promoter in Rice", The Plant Cell, vol. 2, (1990), pp. 1081-1089.
Callis, J., et al., "Introns Increase Gene Expression in Cultured Maize Cells", Genes & Development, vol. 1, (1987), pp. 1183-1200.
Chen, Z.L., et al., "A DNA Sequence Element that Confers Seed-Specific Enhancement to a Constitutive Promoter", The EMBO Journal, vol. 7, No. 2, (1988), pp. 297-302.

(Continued)

*Primary Examiner* — Ashley K Buran
(74) *Attorney, Agent, or Firm* — Marshall, Gerstein & Borun LLP

(57) ABSTRACT

The present invention is in the field of plant molecular biology and provides methods for production of high expressing seed-specific and/or seed-preferential promoters and the production of plants with enhanced seed-specific and/or seed-preferential expression of nucleic acids wherein nucleic acid expression enhancing nucleic acids (NEENAs) are functionally linked to the promoters and/or introduced into plants.

20 Claims, 5 Drawing Sheets

(56) References Cited

FOREIGN PATENT DOCUMENTS

| | | |
|---|---|---|
| WO | WO-2006/003186 A1 | 1/2006 |
| WO | WO-2006/032426 A2 | 3/2006 |
| WO | WO-2006/089950 A2 | 8/2006 |
| WO | WO-2007/039454 A1 | 4/2007 |
| WO | WO-2007/098042 A2 | 8/2007 |
| WO | WO-2007/107516 A2 | 9/2007 |
| WO | WO-2007/112326 A1 | 10/2007 |
| WO | WO-2008/009600 A1 | 1/2008 |
| WO | WO-2008/064128 A2 | 5/2008 |
| WO | WO-2008/104559 A1 | 9/2008 |
| WO | WO-2009/016202 A2 | 2/2009 |
| WO | WO-2009/037329 A2 | 3/2009 |
| WO | WO-2011/023537 A1 | 3/2011 |
| WO | WO-2011/023539 A1 | 3/2011 |
| WO | WO-2011/023800 A1 | 3/2011 |

OTHER PUBLICATIONS

Chung, B.Y.W., et al., "Effect of 5_UTR Introns on Gene Expression in *Arabidopsis thaliana*", BMC Genomics, vol. 7, No. 120, (2006), pp. 1-13.

Fu, H., et al., "High-Level Tuber Expression and Sucrose Inducibility of a Potato Sus4 *Sucrose synthase* Gene Require 5' and 3' Flanking Sequences and the Leader Intron", Plant Cell, vol. 7, 1387-1394.

Fu, H., et al., "A Potato Sus3 Sucrose Synthase Gene Contains a Context-Dependent 3' Element and a Leader Intron with Both Positive and Negative Tissue-Specific Effects", The Plant Cell, vol. 7, (1995), pp. 1395-1403.

Huang, M.T.F., "Intervening Sequences Increase Efficiency of RNA 3' Processing and Accumulation of Cytoplasmic RNA", Nucleic Acid Research, vol. 18, No. 4, ((1989), pp. 937-947.

Kim, M. J., et al., "Seed-Specific Expression of Sesame Microsomal Oleic Acid Desaturase is Controlled by Combinatorial Properties Between Negative cis-Regulatory Elements in the SeFAD2 Promoter and Enhancers in the 5'-UTR Intron", Mol. Gen., Genomics, vol. 276, (2006), pp. 351-368.

Le Hir, H., et al., "How Introns Influence and Enhance Eukaryotic Gene Expression", Trends in Biochemical Sciences, vol. 28, No. 4, (2003), pp. 215-220.

Lu, J., et al., "Gene Expression Enhancement Mediated by the 5' UTR Intron of the Rice rubi3 Gene Varied Remarkably Among Tissues in Transgenic Rice Plants", Mol. Genet. Genomics, vol. 279, (2008), pp. 563-572.

Nott, A., et al., "Splicing Enhances Translation in Mammalian Cells: an Additional Function of the Exon Junction Complex", Genes & Development, vol. 18, (2004), pp. 210-222.

Rose, A. B., "The Effect of Intron Location on Intron-Mediated Enhancement of Gene Expression in *Arabidopsis*", The Plant Journal, vol. 40, (2004), pp. 744-751.

Rose, A., B., et al., "Promoter-Proximal Introns in *Arabidopsis thatliana* are Enriched in Dispersed Signals that Elevate Gene Expression", The Plant Cell, vol. 20, (2008), pp. 543-551.

International Preliminary Report on Patentability for PCT/EP2010/061661, dated Mar. 6, 2012.

Schünmann, P.H.D., et al., Characterization of Promoter Expression Patterns Derived from the Pht1 Phosphate Transporter Genes of Barley (*Hordeum vulgare* L.), Journal of Experimental Botany, vol. 55, No. 398, (2004), pp. 855-865.

Sieburth, L. E., "Molecular Dissection of the *Agamous* Control Region Shows that cis Elements for Spatial Regulation are Located Intragenically", The Plant Cell, vol. 9, (1997), pp. 355-365.

Vasil, V., et al., "Increased Gene Expression by the First Intron of Maize *Shrunken-1* Locus in Grass Species", Plant Physiol., vol. 91, (1989), pp. 1575-1579.

Vitale, A., et al., "Multiple Conserved 5' Elements are Required for High-Level Pollen Expression of the *Arabidopsis* Reproductive Actin ACT1", Plant Molecular Biology, vol. 52, (2003), pp. 1135-1151.

Wang, S., et al., "Control of Plant Trichome Development by a Cotton Fiber MYB Gene", The Plant Cell, vol. 16, (2004), pp. 2323-2334.

"Petroselinum crispum ubiquitin promoter DNA", NCBI database, Accession No. ADH50767, Mar. 25, 2004.

"*A. thaliana* At5g17920 gene constitutive promoter pSUH303GB", NCBI database, Accession No. AEH04981, Jun. 15, 2006.

"Petroselinum crispum UBI4-2 promoter sequence, SEQ ID 7", NCBI database, Accession No. AJV61209, Nov. 29, 2007.

"Sequence 230 from Patent WO0198480", EMBL Database, Accession No. AX461301, Jul. 8, 2002.

"*Arabidopsis thaliana* DNA chromosome 6, BAC clone F13G24 (ESSA project)", EMBL database, Accession No. AL133421, Dec. 10, 1999.

Thomas, M. S., et al, "Identification of an Enhancer Element for the Endosperm-Specific Expression of High Molecular Weight Glutenin", The Plant Cell, vol. 2, (1990), pp. 1171-1180.

Xie, M., et al., "Bidirectionalization of Polar Promoters in Plants", Nature Biotechnology, vol. 19, (2001), pp. 677-678.

Wilmink, A., et al., "Activity of Constitutive Promoters in Various Species from the *Liliaceae*", Plant Molecular Biology, 1995, vol. 28, pp. 949-955.

Chilean Office Action Issued in Chilean Patent Application No. 2012-000550 dated Feb. 11, 2015.

Decision of Grant Issued in Russian Patent Application No. 2012 112 347 dated Apr. 1, 2015.

Decision of Grant Issued in Russian Patent Application No. 2012 112 346 dated Apr. 1, 2015.

Japanese Office Action for Japanese Application No. 2012-525978 dated Oct. 21, 2014 with English Translation Attached.

"*Arabidopsis thaliana* Chromosome 1 BAC T23K8 Sequence, Complete Sequence", GenBank Database Accession No. AC007230, May 13, 1999.

Last, D. I., et al., "pEmu: An Improved Promoter for Gene Expression in Cereal Cells", Theor. Appl. Genet., 1991, vol. 81, No. 5, pp. 581-588.

Gidekel, M., et al., "The First Intron of the *Arabidopsis thaliana* Gene Coding for Elongation Factor 1β Contains an Enhancer-Like Element", Gene, 1996, vol. 170, No. 2, pp. 201-206.

Chen, Z. L., et al., "A DNA Sequence Element that Confers Seed-Specific Enhancement to a Constitutive Promoter", The EMBO J., 1988, vol. 7, No. 2, pp. 297-302.

"*Arabidopsis thaliana* cDNA Clone: RAFL22-53-N05, 5' End", EBI Database Accession No. BP820219, Jan. 22, 2005.

"*Arabidopsis thaliana* Stress Regulated Gene SEQ ID No. 3093", Database GeneSeq, Accession No. ABZ15288, Jan. 21, 2003.

Extended European Search Report for European Application No. 16195551.3 dated Jun. 1, 2017.

* cited by examiner

A)

B)

REGULATORY NUCLEIC ACID MOLECULES FOR ENHANCING SEED-SPECIFIC AND/OR SEED-PREFERENTIAL GENE EXPRESSION IN PLANTS

RELATED APPLICATIONS

This application is a continuation of U.S. application Ser. No. 14/838,950 filed Aug. 28, 2015, which is a divisional application of U.S. application Ser. No. 13/393,045 filed Feb. 28, 2012, now U.S. Pat. No. 9,150,871, which is a national stage application (under 35 U.S.C. § 371) of PCT/EP2010/061661 filed Aug. 11, 2010, which claims benefit of U.S. Provisional Application No. 61/238,233 filed Aug. 31, 2009 and European Application No. 09169017.2 filed Aug. 31, 2009. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074021_0172_03. The size of the text file is 116 KB and the text file was created on Oct. 27, 2016.

FIELD OF THE INVENTION

The present invention is in the field of plant molecular biology and provides methods for production of high expressing seed-specific and/or seed-preferential promoters and the production of plants with enhanced seed-specific and/or seed-preferential expression of nucleic acids wherein nucleic acid expression enhancing nucleic acids (NEENAs) are functionally linked to said promoters and/or introduced into plants.

BACKGROUND OF THE INVENTION

Expression of transgenes in plants is strongly affected by various external and internal factors resulting in a variable and unpredictable level of transgene expression. Often a high number of transformants have to be produced and analyzed in order to identify lines with desirable expression strength. As transformation and screening for lines with desirable expression strength is costly and labor intensive there is a need for high expression of one or more transgenes in a plant. This problem is especially pronounced, when several genes have to be coordinately expressed in a transgenic plant in order to achieve a specific effect as a plant has to be identified in which each and every gene is strongly expressed.

For example, expression of a transgene can vary significantly, depending on construct design and positional effects of the T-DNA insertion locus in individual transformation events.

Strong promoters can partially overcome these challenges. However, availability of suitable promoters showing strong expression with the desired specificity is often limited. In order to ensure availability of sufficient promoters with desired expression specificity, the identification and characterization of additional promoters can help to close this gap. However, natural availability of promoters of the respective specificity and strength and the time consuming characterization of promoter candidates impedes the identification of suitable new promoters.

In order to overcome these challenges, diverse genetic elements and/or motifs have been shown to positively affect gene expression. Among these, some introns have been recognized as genetic elements with a strong potential for improving gene expression. Although the mechanism is largely unknown, it has been shown that some introns positively affect the steady state amount of mature mRNA, possibly by enhanced transcriptional activity, improved mRNA maturation, enhanced nuclear mRNA export and/or improved translation initiation (e.g. Huang and Gorman, 1990; Le Hir et al., 2003; Nott et al., 2004). Since only selected introns were shown to increase expression, splicing as such is likely not accountable for the observed effects.

The increase of gene expression observed upon functionally linking introns to promoters is called intron mediated enhancement (IME) of gene expression and has been shown in various monocotyledonous (e.g. Callis et al., 1987; Vasil et al., 1989; Bruce et al., 1990; Lu et al., 2008) and dicotyledonous plants (e.g. Chung et al., 2006; Kim et al., 2006; Rose et al., 2008). In this respect, the position of the intron in relation to the translational start site (ATG) was shown to be crucial for intron mediated enhancement of gene expression (Rose et al., 2004).

Next to their potential for enhancing gene expression, few introns were shown to also affect the tissue specificity in their native nucleotide environment in plants. Reporter gene expression was found to be dependent on the presence of genomic regions containing up to two introns (Sieburth et al., 1997; Wang et al., 2004). 5' UTR introns have also been reported to be of importance for proper functionality of promoter elements, likely due to tissue specific gene control elements residing in the introns (Fu et al., 1995a; Fu et al., 1995b; Vitale et al., 2003; Kim et al., 2006). However, these studies also show that combination of introns with heterologous promoters can have strong negative impacts on strength and/or specificity of gene expression (Vitale et al., 2003; Kim et al., 2006, WO2006/003186, WO2007/098042). For example the strong constitutive Cauliflower Mosaic Virus CaMV35S promoter is negatively affected through combination with the sesame SeFAD2 5'UTR intron (Kim et al., 2006). In contrast to these observations, some documents show enhanced expression of a nucleic acid by IME without affecting the tissue specificity of the respective promoter (Schünmann et al., 2004). Introns or NEENAs that enhance seed-specific and/or seed-preferential expression when functionally linked to a heterologous promoter have not been shown in the art.

In the present application further nucleic acid molecules are described that enhance the expression of said promoters without affecting their specificity upon functionally linkage to seed-specific and/or seed-preferential promoters. These nucleic acid molecules are in the present application described as "nucleic acid expression enhancing nucleic acids" (NEENA). Introns have the intrinsic feature to be spliced out of the respective pre-mRNA. In contrast to that the nucleic acids presented in the application at hand, do not necessarily have to be included in the mRNA or, if present in the mRNA, have not necessarily to be spliced out of the mRNA in order to enhance the expression derived from the promoter the NEENAs are functionally linked to.

DETAILED DESCRIPTION OF THE INVENTION

Figure 1:
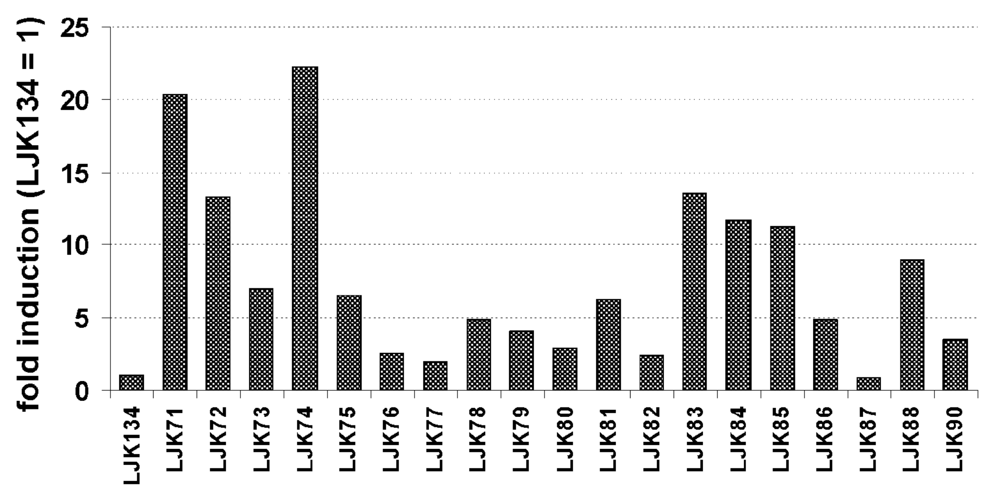
FIG. 1: Luciferase reporter gene expression analysis in cotyledons of stably transformed *A. thaliana* plants of NEENA-less (LJK134) and NEENA-containing constructs (LJK71-LJK90) representing putative NEENA molecules deriving from seed-preferred expressed genes under the control of the p-AtPXR promoter. Expression values are shown in relation to the NEENA-less control construct (LJK134=1).

A first embodiment of the invention comprises a method for production of a high expression seed-specific and/or seed-preferential promoter comprising functionally linking to a promoter one or more nucleic acid expression enhancing nucleic acid (NEENA) molecule comprising i) the nucleic acid molecule having a sequence as defined in any of SEQ ID NO: 1 to 15, or ii) a nucleic acid molecule having a sequence with an identity of 80% or more to any of the sequences as defined by SEQ ID NO:1 to 15, preferably, the identity is 85% or more, more preferably the identity is 90% or more, even more preferably, the identity is 95% or more, 96% or more, 97% or more, 98% or more or 99% or more, in the most preferred embodiment, the identity is 100% to any of the sequences as defined by SEQ ID NO:1 to 15 or iii) a fragment of 100 or more consecutive bases, preferably 150 or more consecutive bases, more preferably 200 consecutive bases or more even more preferably 250 or more consecutive bases of a nucleic acid molecule of i) or ii) which has an expressing enhancing activity, for example 65% or more, preferably 70% or more, more preferably 75% or more, even more preferably 80% or more, 85% or more or 90% or more, in a most preferred embodiment it has 95% or more of the expression enhancing activity as the corresponding nucleic acid molecule having the sequence of any of the sequences as defined by SEQ ID NO:1 to 15, or iv) a nucleic acid molecule which is the complement or reverse complement of any of the previously mentioned nucleic acid molecules under i) to iii), or v) a nucleic acid molecule which is obtainable by PCR using oligonucleotide primers described by SEQ ID NO: 20 to 29, 34 to 41, 44 to 51 and 54 to 57 as shown in Table 2 or vi) a nucleic acid molecule of 100 nucleotides or more, 150 nucleotides or more, 200 nucleotides or more or 250 nucleotides or more, hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO:1 to 15 or the complement thereof. Preferably, said nucleic acid molecule is hybridizing under conditions equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO:1 to 15 or the complement thereof, more preferably, said nucleic acid molecule is hybridizing under conditions equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by any of the sequences as defined by SEQ ID NO:1 to 15 or the complement thereof.

In one embodiment, the one or more NEENA is heterologous to the promoter to which it is functionally linked.

As described above under v) the nucleic acid molecule obtainable by PCR using oligonucleotides as defined by SEQ IDs 20 to 29, 34 to 41, 44 to 51 and 54 to 57 as shown in Table 2 is obtainable for example from genomic DNA from *Arabidopsis* plants such as *A. thaliana* using the conditions as described in Example 1 below.

The skilled person is aware of variations in the temperature profile, cycle number and/or buffer composition or concentration to obtain the respective NEENA molecule. The specific combination of oligonucleotides to be used in the respective PCR reaction for obtaining a respective NEENA molecule is described in Table 2.

A person skilled in the art is aware of methods for rendering a unidirectional to a bidirectional promoter and of methods to use the complement or reverse complement of a promoter sequence for creating a promoter having the same promoter specificity as the original sequence. Such methods are for example described for constitutive as well as inducible promoters by Xie et al. (2001) "Bidirectionalization of polar promoters in plants" nature biotechnology 19 pages 677-679. The authors describe that it is sufficient to add a minimal promoter to the 5' prime end of any given promoter to receive a promoter controlling expression in both directions with same promoter specificity. Hence a high expression promoter functionally linked to a NEENA as described above is functional in complement or reverse complement and therefore the NEENA is functional in complement or reverse complement too.

In principal the NEENA may be functionally linked to any promoter such as tissue specific, inducible, developmental specific or constitutive promoters. The respective NEENA will lead to an enhanced seed-specific and/or seed-preferential expression of the heterologous nucleic acid under the control of the respective promoter to which the one or more NEENA is functionally linked to. The enhancement of expression of promoters other than seed-specific and/or seed-preferential promoters, for example constitutive promoters or promoters with differing tissue specificity, will render the specificity of these promoters. Expression of the nucleic acid under control of the respective promoter will be significantly increased in seeds, where the transcript of said nucleic acid may have not or only weakly been detected without the NEENA functionally linked to its promoter. Hence, tissue- or developmental specific or any other promoter may be rendered to seed-specific and/or seed-preferential promoters by functionally linking one or more of the NEENA molecules as described above to said promoter. It is therefore another embodiment of the invention to provide a method for rendering the specificity of any given promoter functional in plant to a seed-specific and/or seed preferential promoter by linking the respective promoter to a NEENA molecule comprising a sequence as described above under i) to vi).

Preferably, the one or more NEENA is functionally linked to any seed-specific and/or seed-preferential promoter and will enhance expression of the nucleic acid molecule under control of said promoter. Seed-specific and/or seed-preferential promoters to be used in any method of the invention may be derived from plants, for example monocotyledonous or dicotyledonous plants, from bacteria and/or viruses or may be synthetic promoters. Seed specific and/or seed-preferential promoters to be used are for example the SBP-promoter from *Vicia faba*, the Unknown Seed Protein-promoter (USP) from *Vicia faba*, the napin promoter from *Brassica napus*, the conlinin-promoter from *Linum usitatissmum*, the promoter from the *A. thaliana* gene At5g01670 encoding the peroxiredoxin like protein, the promoter of the peroxiredoxin like protein from *Linum usitatissmum*, the globulin like protein promoter from *Brassica napus*, the arcelin5-1 promoter from *Phaseolus vulgaris*, the Zein promoter from *Zea* maize, the globulin promoter from *Zea* maize, the pKG86 promoter from *Zea* maize as described in Example 6 below and the like.

The high expression seed-specific and/or seed-preferential promoters of the invention functionally linked to a NEENA may be employed in any plant comprising for example moss, fern, gymnosperm or angiosperm, for example monocotyledonous or dicotyledonous plant. In a preferred embodiment said promoter of the invention functionally linked to a NEENA may be employed in monocotyledonous or dicotyledonous plants, preferably crop plant such as corn, soy, canola, cotton, potato, sugar beet, rice, wheat, *sorghum*, barley, musa, sugarcane, *miscanthus* and the like. In a preferred embodiment of the invention, said promoter which is functionally linked to a NEENA may be employed in monocotyledonous crop plants such as corn, rice, wheat, *sorghum*, barley, musa, *miscanthus* or sugarcane. In an especially preferred embodiment the promoter functionally linked to a NEENA may be employed in dicotyledonous crop plants such as soy, canola, cotton or potato.

A high expressing seed-specific and/or seed-preferential promoter as used in the application means for example a promoter which is functionally linked to a NEENA causing enhanced seed-specific and/or seed-preferential expression of the promoter in a plant seed or part thereof wherein the accumulation of RNA or rate of synthesis of RNA in seeds derived from the nucleic acid molecule under the control of the respective promoter functionally linked to a NEENA is higher, preferably significantly higher than the expression in seeds caused by the same promoter lacking a NEENA of the invention. Preferably the amount of RNA of the respective nucleic acid and/or the rate of RNA synthesis and/or the RNA stability in a plant is increased 50% or more, for example 100% or more, preferably 200% or more, more preferably 5 fold or more, even more preferably 10 fold or more, most preferably 20 fold or more for example 50 fold compared to a control plant of same age grown under the same conditions comprising the same seed-specific and/or seed-preferential promoter the latter not being functionally linked to a NEENA of the invention.

When used herein, significantly higher refers to statistical significance the skilled person is aware how to determine, for example by applying statistical tests such as the t-test to the respective data sets.

Methods for detecting expression conferred by a promoter are known in the art. For example, the promoter may be functionally linked to a marker gene such as GUS, GFP or luciferase and the activity of the respective protein encoded by the respective marker gene may be determined in the plant or part thereof. As a representative example, the method for detecting luciferase is described in detail below. Other methods are for example measuring the steady state level or synthesis rate of RNA of the nucleic acid molecule controlled by the promoter by methods known in the art, for example Northern blot analysis, qPCR, run-on assays or other methods described in the art.

A skilled person is aware of various methods for functionally linking two or more nucleic acid molecules. Such methods may encompass restriction/ligation, ligase independent cloning, recombineering, recombination or synthesis. Other methods may be employed to functionally link two or more nucleic acid molecules.

A further embodiment of the present invention is a method for producing a plant or part thereof with, compared to a respective control plant or part thereof, enhanced seed-specific and/or seed-preferential expression of one or more nucleic acid molecule comprising the steps of introducing into the plant or part thereof one or more NEENA comprising a nucleic acid molecule as defined above under i) to vi) and functionally linking said one or more NEENA to a promoter, preferably a seed-specific and/or seed-preferential promoter and to a nucleic acid molecule being under the control of said promoter, preferably seed-specific and/or seed-preferential promoter, wherein the NEENA is heterologous to said nucleic acid molecule.

The NEENA may be heterologous to the nucleic acid molecule which is under the control of said promoter to which the NEENA is functionally linked or it may be heterologous to both the promoter and the nucleic acid molecule under the control of said promoter.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a NEENA of the invention is in its natural environment functionally linked to its native promoter, whereas in the present invention it is linked to another promoter which might be derived from the same organism, a different organism or might be a synthetic promoter. It may also mean that the NEENA of the present invention is linked to its native promoter but the nucleic acid molecule under control of said promoter is heterologous to the promoter comprising its native NEENA. It is in addition to be understood that the promoter and/or the nucleic acid molecule under the control of said promoter functionally linked to a NEENA of the invention are heterologous to said NEENA as their sequence has been manipulated by for example mutation such as insertions, deletions and the forth so that the natural sequence of the promoter and/or the nucleic acid molecule under control of said promoter is modified and therefore have become heterologous to a NEENA of the invention. It may also be understood that the NEENA is heterologous to the nucleic acid to which it is functionally linked when the NEENA is functionally linked to its native promoter wherein the position of the NEENA in relation to said promoter is changed so that the promoter shows higher expression after such manipulation.

A plant exhibiting enhanced seed-specific and/or seed-preferential expression of a nucleic acid molecule as meant herein means a plant having a higher, preferably statistically significant higher seed-specific and/or seed-preferential expression of a nucleic acid molecule compared to a control plant grown under the same conditions without the respective NEENA functionally linked to the respective nucleic acid molecule. Such control plant may be a wild-type plant or a transgenic plant comprising the same promoter controlling the same gene as in the plant of the invention wherein the promoter is not linked to a NEENA of the invention.

Producing a plant as used herein comprises methods for stable transformation such as introducing a recombinant DNA construct into a plant or part thereof by means of *Agrobacterium* mediated transformation, protoplast transformation, particle bombardment or the like and optionally subsequent regeneration of a transgenic plant. It also comprises methods for transient transformation of a plant or part thereof such as viral infection or *Agrobacterium* infiltration. A skilled person is aware of further methods for stable and/or transient transformation of a plant or part thereof. Approaches such as breeding methods or protoplast fusion might also be employed for production of a plant of the invention and are covered herewith.

The method of the invention may be applied to any plant, for example gymnosperm or angiosperm, preferably angiosperm, for example dicotyledonous or monocotyledonous plants, preferably dicotyledonous plants. Preferred monocotyledonous plants are for example corn, wheat, rice, barley, *sorghum*, musa, sugarcane, *miscanthus* and *brachypodium*, especially preferred monocotyledonous plants are corn, wheat and rice. Preferred dicotyledonous plants are for example soy, rape seed, canola, linseed, cotton, potato, sugar beet, *tagetes* and *Arabidopsis*, especially preferred dicotyledonous plants are soy, rape seed, canola and potato In one embodiment of the invention, the methods as defined above are comprising the steps of a) introducing the one or more NEENA comprising a nucleic acid molecule as defined above in i) to vi) into a plant or part thereof, and b) integrating said one or more NEENA into the genome of said plant or part thereof whereby said one or more NEENA is functionally linked to an endogenous preferably seed-specific and/or seed-preferential expressed nucleic acid heterologous to said one or more NEENA and optionally c) regenerating a plant or part thereof comprising said one or more NEENA from said transformed cell.

The one or more NEENA molecule may be introduced into the plant or part thereof by means of particle bombardment, protoplast electroporation, virus infection, *Agrobacterium* mediated transformation or any other approach known in the art. The NEENA molecule may be introduced integrated for example into a plasmid or viral DNA or viral RNA. The NEENA molecule may also be comprised on a BAC, YAC or artificial chromosome prior to introduction into the plant or part of the plant. It may be also introduced as a linear nucleic acid molecule comprising the NEENA sequence wherein additional sequences may be present adjacent to the NEENA sequence on the nucleic acid molecule. These sequences neighboring the NEENA sequence may be from about 20 bp, for example 20 bp to several hundred base pairs, for example 100 bp or more and may facilitate integration into the genome for example by homologous recombination. Any other method for genome integration may be employed, be it targeted integration approaches, such as homologous recombination or random integration approaches, such as illegitimate recombination.

The endogenous preferably seed-specific and/or seed-preferential expressed nucleic acid to which the NEENA molecule may be functionally linked may be any nucleic acid, preferably any seed-specific and/or seed-preferential expressed nucleic acid molecule. The nucleic acid molecule may be a protein coding nucleic acid molecule or a non coding molecule such as antisense RNA, rRNA, tRNA, miRNA, ta-siRNA, siRNA, dsRNA, snRNA, snoRNA or any other noncoding RNA known in the art.

The skilled person is aware of methods for identifying seed-specific and/or seed-preferential expressed nucleic acid molecules to which the method of the invention may preferably be applied for example by microarray chip hybridization, qPCR, Northern blot analysis, next generation sequencing etc.

A further way to perform the methods of the invention may be to a) provide an expression construct comprising one or more NEENA comprising a nucleic acid molecule as defined above in i) to vi) functionally linked to a promoter, preferably a seed-specific and/or seed-preferential promoter as defined above and to one or more nucleic acid molecule the latter being heterologous to said one or more NEENA and which is under the control of said promoter, preferably seed-specific and/or seed-preferential promoter and b) integrate said expression construct comprising said one or more NEENA into the genome of said plant or part thereof and optionally c) regenerate a plant or part thereof comprising said one or more expression construct from said transformed plant or part thereof.

The NEENA may be heterologous to the nucleic acid molecule which is under the control of said promoter to which the NEENA is functionally linked or it may be heterologous to both the promoter and the nucleic acid molecule under the control of said promoter.

The expression construct may be integrated into the genome of the respective plant with any method known in the art. The integration may be random using methods such as particle bombardment or *Agrobacterium* mediated transformation. In a preferred embodiment, the integration is via targeted integration for example by homologous recombination. The latter method would allow integrating the expression construct comprising a high expression promoter functionally linked to a NEENA into a favorable genome region. Favorable genome regions are for example genome regions known to comprise genes that are highly expressed for example in seeds and hence may increase expression derived from said expression construct compared to a genome region which shows no transcriptional activity.

In another preferred embodiment said one or more NEENA is functionally linked to a promoter, preferably a seed-specific and/or seed-preferential promoter close to the transcription start site of said heterologous nucleic acid molecule.

Close to the transcription start site as meant herein comprises functionally linking the one or more NEENA to a promoter, preferably a seed-specific and/or seed-preferential promoter 2500 bp or less, preferentially 2000 bp or less, more preferred 1500 bp or less, even more preferred 1000 bp or less and most preferred 500 bp or less away from the transcription start site of said heterologous nucleic acid molecule. It is to be understood that the NEENA may be integrated upstream or downstream in the respective distance from the transcription start site of the respective promoter. Hence, the one or more NEENA must not necessarily be included in the transcript of the respective heterologous nucleic acid under control of the preferably seed-specific and/or seed-preferential promoter the one or more NEENA is functionally linked to. Preferentially the one or more NEENA is integrated downstream of the transcription start site of the respective promoter, preferably seed-specific and/or seed-preferential promoter. The integration site downstream of the transcription start site may be in the 5' UTR, the 3' UTR, an exon or intron or it may replace an intron or partially or completely the 5' UTR or 3' UTR of the heterologous nucleic acid under the control of the preferably seed-specific and/or seed-preferential promoter. Preferentially the one or more NEENA is integrated in the 5' UTR or an intron or the NEENA is replacing an intron or a part or the complete 5'UTR, most preferentially it is integrated in the 5'UTR of the respective heterologous nucleic acid.

A further embodiment of the invention comprises a recombinant expression construct comprising one or more NEENA comprising a nucleic acid molecule as defined above in i) to vi).

The recombinant expression construct may further comprise one or more promoter, preferably seed-specific and/or seed-preferential promoter to which the one or more NEENA is functionally linked and optionally one or more expressed nucleic acid molecule the latter being heterologous to said one or more NEENA.

The NEENA may be heterologous to the nucleic acid molecule which is under the control of said promoter to which the NEENA is functionally linked or it may be heterologous to both the promoter and the nucleic acid molecule under the control of said promoter.

The expression construct may comprise one ore more, for example two or more, for example 5 or more, such as 10 or more combinations of promoters, preferably seed-specific and/or seed-preferential promoters functionally linked to a NEENA and a nucleic acid molecule to be expressed which is heterologous to the respective NEENA. The expression construct may also comprise further promoters not comprising a NEENA functionally linked to nucleic acid molecules to be expressed homologous or heterologous to the respective promoter.

A recombinant expression vector comprising one or more recombinant expression construct as defined above is another embodiment of the invention. A multitude of expression vectors that may be used in the present invention are known to a skilled person. Methods for introducing such a vector comprising such an expression construct comprising for example a promoter functionally linked to a NEENA and optionally other elements such as a terminator into the genome of a plant and for recovering transgenic plants from a transformed cell are also well known in the art. Depending on the method used for the transformation of a plant or part thereof the entire vector might be integrated into the genome of said plant or part thereof or certain components of the vector might be integrated into the genome, such as, for example a T-DNA.

A transgenic plant or part thereof comprising one or more heterologous NEENA as defined above in i) to vi) is also enclosed in this invention. A NEENA is to be understood as being heterologous to the plant if it is synthetic, derived from another organism or the same organism but its natural genomic localization is rendered compared to a control plant, for example a wild type plant. It is to be understood, that a rendered genomic localization means the NEENA is located on another chromosome or on the same chromosome but 10 kb or more, for example 10 kb, preferably 5 kb or more, for example 5 kb, more preferably 1000 bp or more, for example 1000 bp, even more preferably 500 bp or more, for example 500 bp, especially preferably 100 bp or more, for example 100 bp, most preferably 10 bp or more, for example 10 bp dislocated from its natural genomic localization, for example in a wild type plant.

A transgenic cell or transgenic plant or part thereof comprising a recombinant expression vector as defined above or a recombinant expression construct as defined above is a further embodiment of the invention. The transgenic cell, transgenic plant or part thereof may be selected from the group consisting of bacteria, fungi, yeasts, or plant, insect or mammalian cells or plants. Preferred transgenic cells are bacteria, fungi, yeasts, plant cells. Preferred bacteria are Enterobacteria such as *E. coli* and bacteria of the genus *Agrobacteria*, for example *Agrobacterium tumefaciens* and *Agrobacterium rhizogenes*. Preferred plants are monocotyledonous or dicotyledonous plants for example monocotyledonous or dicotyledonous crop plants such as corn, soy, canola, cotton, potato, sugar beet, rice, wheat, *sorghum*, barley, musa, sugarcane, *miscanthus* and the like. Preferred crop plants are corn, rice, wheat, soy, canola, cotton or potato. Especially preferred dicotyledonous crop plants are soy, canola, cotton or potato.

Especially preferred monocotyledonous crop plants are corn, wheat and rice.

A transgenic cell culture, transgenic seed, parts or propagation material derived from a transgenic cell or plant or part thereof as defined above comprising said heterologous NEENA as defined above in i) to vi) or said recombinant expression construct or said recombinant vector as defined above are other embodiments of the invention.

Transgenic parts or propagation material as meant herein comprise all tissues and organs, for example leaf, stem and fruit as well as material that is useful for propagation and/or regeneration of plants such as cuttings, scions, layers, branches or shoots comprising the respective NEENA, recombinant expression construct or recombinant vector.

A further embodiment of the invention is the use of the NEENA as defined above in i) to vi) or the recombinant construct or recombinant vector as defined above for enhancing expression in plants or parts thereof.

Hence the application at hand provides seed-specific and/or seed-preferential gene expression enhancing nucleic acid molecules comprising one or more promoter, preferably seed-specific and/or seed preferential promoter functionally linked to one ore more NEENA. Additionally use of such gene expression enhancing nucleic acid molecules and expression constructs, expression vectors, transgenic plants or parts thereof and transgenic cells comprising such gene expression enhancing nucleic acid molecules are provided.

A use of a transgenic cell culture, transgenic seed, parts or propagation material derived from a transgenic cell or plant or part thereof as defined above for the production of foodstuffs, animal feeds, seeds, pharmaceuticals or fine chemicals is also enclosed in this invention.

DEFINITIONS

Abbreviations: NEENA—nucleic acid expression enhancing nucleic acid, GFP—green fluorescence protein, GUS—beta-Glucuronidase, BAP—6-benzylaminopurine; 2,4-D-2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium, microl: Microliter.

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word or means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3 direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3 is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Enhanced expression: "enhance" or "increase" the expression of a nucleic acid molecule in a plant cell are used equivalently herein and mean that the level of expression of the nucleic acid molecule in a plant, part of a plant or plant cell after applying a method of the present invention is higher than its expression in the plant, part of the plant or plant cell before applying the method, or compared to a reference plant lacking a recombinant nucleic acid molecule of the invention. For example, the reference plant is comprising the same construct which is only lacking the respective NEENA. The term "enhanced" or "increased" as used herein are synonymous and means herein higher, preferably significantly higher expression of the nucleic acid molecule to be expressed. As used herein, an "enhancement" or "increase" of the level of an agent such as a protein, mRNA or RNA means that the level is increased relative to a substantially identical plant, part of a plant or plant cell grown under substantially identical conditions, lacking a recombinant nucleic acid molecule of the invention, for example lacking the NEENA molecule, the recombinant construct or recombinant vector of the invention. As used herein, "enhancement" or "increase" of the level of an agent, such as for example a preRNA, mRNA, rRNA, tRNA, snoRNA, snRNA expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a cell or organism lacking a recombinant nucleic acid molecule of the invention. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the induced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254). As one example for quantifying the activity of a protein, the detection of luciferase activity is described in the Examples below.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a seed-specific and/or seed-preferential promoter or of an inducible promoter, which initiates transcription only when the host cell is exposed to some particular external stimulus. In the case of a plant, the promoter can also be specific to a particular tissue or organ or stage of development.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or a NEENA) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

High expression seed-specific and/or seed-preferential promoter: A "high expression seed-specific and/or seed-preferential promoter" as used herein means a promoter causing seed-specific and/or seed-preferential expression in a plant or part thereof wherein the accumulation or rate of synthesis of RNA or stability of RNA derived from the nucleic acid molecule under the control of the respective promoter is higher, preferably significantly higher than the expression caused by the promoter lacking the NEENA of the invention. Preferably the amount of RNA and/or the rate of RNA synthesis and/or stability of RNA is increased 50% or more, for example 100% or more, preferably 200% or more, more preferably 5 fold or more, even more preferably 10 fold or more, most preferably 20 fold or more for example 50 fold relative to a seed-specific and/or seed-preferential promoter lacking a NEENA of the invention.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41 (% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions×100). The terms "homology" and "identity" are thus to be considered as synonyms.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in defines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perform gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -0 SeqAlign file [File Out] Optional; -J Believe the query define [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSITBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence homology are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the homology is calculated on the complete length of the query sequence, for example SEQ ID NO: 1.

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG.

Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron is comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

NEENA: see "Nucleic acid expression enhancing nucleic acid".

Non-coding: The term "non-coding" refers to sequences of nucleic acid molecules that do not encode part or all of an expressed protein. Non-coding sequences include but are not limited to introns, enhancers, promoter regions, 3 untranslated regions, and 5' untranslated regions.

Nucleic acid expression enhancing nucleic acid (NEENA): The term "nucleic acid expression enhancing nucleic acid" refers to a sequence and/or a nucleic acid molecule of a specific sequence having the intrinsic property to enhance expression of a nucleic acid under the control of a promoter to which the NEENA is functionally linked. Unlike promoter sequences, the NEENA as such is not able to drive expression. In order to fulfill the function of enhancing expression of a nucleic acid molecule functionally linked to the NEENA, the NEENA itself has to be functionally linked to a promoter. In distinction to enhancer sequences known in the art, the NEENA is acting in cis but not in trans and has to be located close to the transcription start site of the nucleic acid to be expressed.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, *sorghum*, millet, rye, *triticale*, or oats; the family of the Umbelliferae, especially the genus *Daucus*, very especially the species *carota* (carrot) and *Apium*, very especially the species *Graveolens dulce* (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus Glycine, very especially the species max (soybean), alfalfa, pea, lucerne, beans or peanut and many others; and the family of the Cruciferae (*Brassicacae*), especially the genus *Brassica*, very especially the species *napus* (oil seed rape), *campestris* (beet), *oleracea* cv Tastie (cabbage), *oleracea* cv Snowball Y (cauliflower) and *oleracea* cv Emperor (broccoli); and of the genus *Arabidopsis*, very especially the species *thaliana* and many others; the family of the Compositae, especially the genus *Lactuca*, very especially the species *sativa* (lettuce) and many others; the family of the Asteraceae such as sunflower, *Tagetes*, lettuce or *Calendula* and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases grassius.org/grasspromdb.html, mendel.cs.rhul.ac.uk/mendel.php?topic=plantprom, ppdb.gene.nagoya-u.ac.jp/cgi-bin/index.cgi. Promoters listed there may be addressed with the methods of the invention and are herewith included by reference. A promoter is located 5 (i.e., upstream), proximal to the transcriptional start site of a nucleotide sequence of interest whose transcription into mRNA it controls, and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules may also comprise molecules, which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

"Seed-specific promoter" in the context of this invention means a promoter which is regulating transcription of a nucleic acid molecule under control of the respective promoter in seeds wherein the transcription in any tissue or cell of the seeds contribute to more than 90%, preferably more than 95%, more preferably more than 99% of the entire quantity of the RNA transcribed from said nucleic acid sequence in the entire plant during any of its developmental stage. The term "seed-specific expression" and "seed-specific NEENA" are to be understood accordingly. Hence a "seed-specific NEENA" enhances the transcription of a seed-specific or seed-preferential promoter in a way, that the transcription in seeds derived from said promoter functionally linked to a respective NEENA contribute to more than 90%, preferably more than 95%, more preferably more than 99% of the entire quantity of the RNA transcribed from the respective promoter functionally linked to a NEENA in the entire plant during any of its developmental stage.

"Seed-preferential promoter" in the context of this invention means a promoter which is regulating transcription of a nucleic acid molecule under control of the respective promoter in seeds wherein the transcription in any tissue or cell of the seeds contribute to more than 50%, preferably more than 70%, more preferably more than 80% of the entire quantity of the RNA transcribed from said nucleic acid sequence in the entire plant during any of its developmental stage. The term "seed-preferential expression" and "seed-preferential NEENA" are to be understood accordingly. Hence a "seed-preferential NEENA" enhances the transcription of a seed-specific or seed-preferential promoter in a way, that the transcription in seeds derived from said promoter functionally linked to a respective NEENA contribute to more than 50%, preferably more than 70%, more preferably more than 80% of the entire quantity of the RNA transcribed from the respective promoter functionally linked to a NEENA in the entire plant during any of its developmental stage.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Significant increase or decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Small nucleic acid molecules: "small nucleic acid molecules" are understood as molecules consisting of nucleic acids or derivatives thereof such as RNA or DNA. They may be double-stranded or single-stranded and are between about 15 and about 30 bp, for example between 15 and 30 bp, more preferred between about 19 and about 26 bp, for example between 19 and 26 bp, even more preferred between about 20 and about 25 bp for example between 20 and 25 bp. In a especially preferred embodiment the oligonucleotides are between about 21 and about 24 bp, for example between 21 and 24 bp. In a most preferred embodiment, the small nucleic acid molecules are about 21 bp and about 24 bp, for example 21 bp and 24 bp.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems, Foster City, Calif., USA) using the Sanger technology (Sanger et al., 1977). Unless described otherwise, chemicals and reagents were obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases were from New England Biolabs (Ipswich, Mass., USA) or Roche Diagnostics GmbH (Penzberg, Germany). Oligonucleotides were synthesized by Eurofins MWG Operon (Ebersberg, Germany).

Example 1: Identification of Nucleic Acid Expression Enhancing Nucleic Acids (NEENA) Candidates from Genes with Seed-Specific or Seed-Preferential Expression

1.1 Identification of NEENA Molecules from *A. thaliana* Genes

Using publicly available genomic DNA sequences (e.g. ncbi.nlm.nih.gov/genomes/PLANTS/PlantList.html) and transcript expression data (e.g. weigelworld.org/resources/microarray/AtGenExpress/), a set of 19 NEENA candidates deriving from *Arabidopsis thaliana* transcripts with seed-specific or seed-preferential expression was selected for detailed analyses. The candidates were named as follows:

TABLE 1

| seed specific NEENA candidates (NEENAss). | | | |
|---|---|---|---|
| NEENA name | Locus | Annotation | SEQ ID NO |
| NEENAss1 | At1g62290 | aspartyl protease family protein | 1 |
| NEENAss2 | At1g65090 | expressed protein | 2 |
| NEENAss15 | At2g27040 | PAZ domain-containing protein | 3 |
| NEENAss18 | At1g01170 | ozone-responsive stress-related protein, putative | 4 |
| NEENAss14 | At5g63190 | MA3 domain-containing protein | 5 |
| NEENAss4 | At5g07830 | glycosyl hydrolase family 79 N-terminal domain-containing protein similar to beta-glucuronidase AtGUS2 | 6 |
| NEENAss13 | At2g04520 | eukaryotic translation initiation factor 1A, putative/eIF-1A | 7 |
| NEENAss3 | At5g60760 | 2-phosphoglycerate kinase-related | 8 |
| NEENAss5 | At1g11170 | expressed protein contains Pfam profile PF05212 | 9 |
| NEENAss11 | At4g37050 | PLA V/PLP4 (Patatin-like protein 4) | 10 |
| NEENAss8 | At1g56170 | HAP5B (Heme activator protein (yeast) homolog 5B) | 11 |
| NEENAss16 | At1g54100 | aldehyde dehydrogenase, putative/antiquitin | 12 |
| NEENAss9 | At3g12670 | CTP synthase, putative/UTP--ammonia ligase, putative | 13 |
| NEENAss20 | At4g04460 | aspartyl protease family protein | 14 |
| NEENAss10 | At1g04120 | ATMRP5 (*Arabidopsis thaliana* multidrug resistance-associated protein 5) | 15 |
| NEENAss6 | At2g41070 | basic leucine zipper transcription factor (BZIP12) | 16 |
| NEENAss12 | At1g05450 | protease inhibitor/seed storage/lipid transfer protein (LTP)-related | 17 |
| NEENAss7 | At4g03050 | 2-oxoglutarate-dependent dioxygenase, putative (AOP3) | 18 |
| NEENAss17 | At3g12490 | cysteine protease inhibitor, putative/cystatin | 19 |

1.2 Isolation of the NEENA Candidates

Genomic DNA was extracted from *A. thaliana* green tissue using the Qiagen DNeasy Plant Mini Kit (Qiagen, Hilden, Germany). Genomic DNA fragments containing putative NEENA molecules were isolated by conventional polymerase chain reaction (PCR). Primers were designed on the basis of the *A. thaliana* genome sequence with a multitude of NEENA candidates. The reaction comprised 19 sets of primers (Table 2) and followed the protocol outlined by Phusion High Fidelity DNA Polymerase (Cat No F-540L, New England Biolabs, Ipswich, Mass., USA). The isolated DNA was used as template DNA in a PCR amplification using the following primers:

TABLE 2

| Primer sequences | | | |
|---|---|---|---|
| Primer name | Sequence | SEQ ID NO | PCR yielding SEQ ID NO |
| NEENAss1_for | aataatggtacctggtgcttaaacactctggtgagt | 20 | 1 |
| NEENAss1_rev | aataatccatggtttgacctacaaaatcaaagcagtca | 21 | |
| NEENAss2_for | tttttggtaccagttctttgctttcgaagttgc | 22 | 2 |
| NEENAss2_rev | ttttttccatggtactacgtactgttttcaattct | 23 | |
| NEENAss3_for | aaaaaaggtaccatttccacacgctttctatcatttc | 24 | 8 |
| NEENAss3_rev | aaaaaaccatggttatctctctctaaaaaataaaaacgaatc | 25 | |
| NEENAss4_for | aataaaggtaccgtccagaattttctccattga | 26 | 6 |
| NEENAss4_rev | aataaaccatggtcttcactatccaaagctctca | 27 | |
| NEENAss5_for | tttttggtaccgtctactttcattacagtgactctg | 28 | 9 |
| NEENAss5_rev | ttttttccatggttatattttacctgcaacacaattcaa | 29 | |
| NEENAss6_for | ttttatggtacccactcgaatactgcatgcaa | 30 | 16 |
| NEENAss6_rev | ttttatccatggttatgtagcctttacacagaaaacaa | 31 | |
| NEENAss7_for | tatataggtaccaacaactatggcctgagggt | 32 | 18 |
| NEENAss7_rev | tatataccatggttatcttactgtttttaaccaaaaaataaaat | 33 | |
| NEENAss8_for | tttttaggtaccatcttagggtttcgcgagatctca | 34 | 11 |
| NEENAss8_rev | ttttttccatggtgctaagctatctctgttaatataaaattg | 35 | |
| NEENAss9_for | tttttggtaccattttttgttggtgaaaggtaga | 36 | 13 |
| NEENAss9_rev | tttttaccatggttacgtttttgtctctgcttcttct | 37 | |

TABLE 2-continued

| Primer sequences | | | |
|---|---|---|---|
| Primer name | Sequence | SEQ ID NO | PCR yielding SEQ ID NO |
| NEENAss10_for | tatattggtacctctgggaaatatcgattttgatct | 38 | 15 |
| NEENAss10_rev | tatataccatggtctcaccacatcccaaagctc | 39 | |
| NEENAss11_for | ttttatggtaccgcacaatcttagcttaccttgaa | 40 | 10 |
| NEENAss11_rev | ttttatccatggttatttaatccacaagccttgcctc | 41 | |
| NEENAss12_for | tttttaggtacctgtcggagaagtgggcg | 42 | 17 |
| NEENAsskor-rev | tttttaccatggagaagtgggcggacg | 43 | |
| NEENAss13_for | ttttatggtacctagcttaatctcagattcgaatcgt | 44 | 7 |
| NEENAss13_rev | ttttatccatggtagtatctacataccaatcatacaaatg | 45 | |
| NEENAss14_for | ttttttggtacctttcacgatttggaatttga | 46 | 5 |
| NEENAss14_rev | ttttttccatggtctacaacattaaaacgaccatta | 47 | |
| NEENAss15_for | tatataggtaccagggtttcgtttttgtttca | 48 | 3 |
| NEENAss15_rev | tatataccatggttatctcctgctcaaagaaacca | 49 | |
| NEENAss16_for | tttataggtaccagaagctcatttcttcgatac | 50 | 12 |
| NEENAss16_rev | tttataccatggtctctgcgcaaaaattcacc | 51 | |
| NEENAss17_for | tatattggtacctctaaaaatacagggcacc | 52 | 19 |
| NEENAss17_rev | tatattccatggttactcttcgttgcagaagccta | 53 | |
| NEENAss18_for | tatataggtaccactgtttaagcttcactgtct | 54 | 4 |
| NEENAss18_rev | tatataccatggtttcttctaaagctgaaagt | 55 | |
| NEENAss20_for | tatataggtaccttaagcttttaagaatctctactcaca | 56 | 14 |
| NEENAss20(2)_rev | atatatccatggttaaattttacctgtcatcaaaaacaaca | 57 | |

Amplification during the PCR was carried out with the following composition (50 microl):

3.00 microl *A. thaliana* genomic DNA (50 ng/microl)

10.00 microl 5× Phusion HF Buffer 4.00 microl dNTP (2.5 mM)

2.50 microl for Primer (10 microM)

2.50 microl rev Primer (10 microM)

0.50 microl Phusion HF DNA Polymerase (2 U/microl)

A touch-down approach was employed for the PCR with the following parameters: 98.0° C. for 30 sec (1 cycle), 98.0° C. for 30 sec, 56.0° C. for 30 sec and 72.0° C. for 60 sec (4 cycles), 4 additional cycles each for 54.0° C., 51.0° C. and 49.0° C. annealing temperature, followed by 20 cycles with 98.0° C. for 30 sec, 46.0° C. for 30 sec and 72.0° C. for 60 sec (4 cycles) and 72.0° C. for 5 min. The amplification products were loaded on a 2% (w/v) agarose gel and separated at 80V. The PCR products were excised from the gel and purified with the Qiagen Gel Extraction Kit (Qiagen, Hilden, Germany). Following a DNA restriction digest with NcoI (10 U/microl) and KpnI (10 U/microl) restriction endonuclease, the digested products were again purified with the Qiagen Gel Extraction Kit (Qiagen, Hilden, Germany).

1.3 Vector Construction

Using the Multisite Gateway System (Invitrogen, Carlsbad, Calif., USA), the promoter::NEENA::reporter-gene cassettes were assembled into binary constructs for plant transformation. The *A. thaliana* p-AtPXR (At1g48130, GenBank AC023673.3; WO2006089950; with the prefix p- denoting promoter) seed specific promoter was used in the reporter gene construct, and firefly luciferase (Promega, Madison, Wis., USA) was utilized as reporter protein for quantitatively determining the expression enhancing effects of the NEENA molecules to be analyzed.

The pENTR/A vector holding the p-AtPXR promoter was cloned via site specific recombination (BP-reaction) between the pDONR/A vector and p-AtPXR amplification products with primers p-AtPXR-for and p-AtPXR-rev (Table 3) on genomic DNA (see above) with site specific recombination sites at either end according to the manufacturers manual (Invitrogen, Carlsbad, Calif., USA). Positive pENTR/A clones underwent sequence analysis to ensure correctness of p-AtPXR promoter.

TABLE 3

| Primer sequences (p-AtPXR) | | |
|---|---|---|
| Primer name | Sequence | SEQ ID NO. |
| p-AtPXR-for | ggggacaactttgtatagaaaagttggccacatcatgtttagacttatc | 58 |
| p-AtPXR-rev | ggggactgctttttttgtacaaacttgtttaccttttatatttatatatag | 59 |

An ENTR/B vector containing the firefly luciferase coding sequence (Promega, Madison, Wis., USA) followed by the t-nos nopalin synthase transcriptional terminator (Genbank V00087) was generated. NEENA candidate PCR fragments (see above) were cloned separately upstream of the firefly luciferase coding sequence using KpnI and NcoI restriction enzymes. The resulting pENTR/B vectors are summarized in table 4, with promoter molecules having the prefix p-, coding sequences having the prefix c-, and terminator molecules having the prefix t-.

TABLE 4 all pENTR/B vectors plus and minus NEENA candidates

| pENTR/B vector | Composition of the partial expression cassette SEQ ID NO::reporter gene::terminator |
|---|---|
| LJK01 | MCS::c-LUC::t-nos |
| LJK19 | SEQ ID NO1::c-LUC::t-nos |
| LJK20 | SEQ ID NO2::c-LUC::t-nos |
| LJK21 | SEQ ID NO8::c-LUC::t-nos |
| LJK22 | SEQ ID NO6::c-LUC::t-nos |
| LJK23 | SEQ ID NO9::c-LUC::t-nos |
| LJK24 | SEQ ID NO16::c-LUC::t-nos |
| LJK25 | SEQ ID NO18::c-LUC::t-nos |
| LJK26 | SEQ ID NO11::c-LUC::t-nos |
| LJK27 | SEQ ID NO13::c-LUC::t-nos |
| LJK28 | SEQ ID NO15::c-LUC::t-nos |
| LJK29 | SEQ ID NO10::c-LUC::t-nos |
| LJK30 | SEQ ID NO17::c-LUC::t-nos |
| LJK31 | SEQ ID NO7::c-LUC::t-nos |
| LJK32 | SEQ ID NO5::c-LUC::t-nos |
| LJK33 | SEQ ID NO3::c-LUC::t-nos |
| LJK34 | SEQ ID NO12::c-LUC::t-nos |
| LJK35 | SEQ ID NO19::c-LUC::t-nos |
| LJK36 | SEQ ID NO4::c-LUC::t-nos |
| LJK38 | SEQ ID NO14::c-LUC::t-nos |

The pENTR/C vector was constructed by introduction of a multiple cloning site (SEQ ID NO60) via KpnI and HindIII restriction sites. By performing a site specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded 1 binary vector with p-AtPXR promoter, the firefly luciferase coding sequence c-LUC and the t-nos terminator and 19 vectors harboring SEQ ID NO1, NO2, NO3, NO4, NO5, NO6, NO7, NO8, NO9, NO10, NO11, NO12, NO13, NO14, NO15, NO16, NO17, NO18 and NO19 immediately upstream of the firefly luciferase coding sequence (Table 5), for which the combination with SEQ ID NO1 is given exemplary (SEQ ID NO61). Except for varying SEQ ID NO2 to NO19, the nucleotide sequence is identical in all vectors (Table 5). The resulting plant transformation vectors are summarized in table 5:

TABLE 5

Plant expression vectors for *A. thaliana* transformation

| plant expression vector | Composition of the expression cassette Promoter::SEQ ID NO::reporter gene::terminator | SEQ ID NO |
|---|---|---|
| LJK134 | p-AtPXR::-::c-LUC::t-nos | |
| LJK71 | p-AtPXR::SEQ ID NO1::c-LUC::t-nos | 61 |
| LJK72 | p-AtPXR::SEQ ID NO2::c-LUC::t-nos | |
| LJK73 | p-AtPXR::SEQ ID NO8::c-LUC::t-nos | |
| LJK74 | p-AtPXR::SEQ ID NO6::c-LUC::t-nos | |
| LJK75 | p-AtPXR::SEQ ID NO9::c-LUC::t-nos | |
| LJK76 | p-AtPXR::SEQ ID NO16::c-LUCA-nos | |
| LJK77 | p-AtPXR::SEQ ID NO18::c-LUCA-nos | |
| LJK78 | p-AtPXR::SEQ ID NO11::c-LUCA-nos | |
| LJK79 | p-AtPXR::SEQ ID NO13::c-LUCA-nos | |
| LJK80 | p-AtPXR::SEQ ID NO15::c-LUCA-nos | |
| LJK81 | p-AtPXR::SEQ ID NO10::c-LUCA-nos | |
| LJK82 | p-AtPXR::SEQ ID NO17::c-LUCA-nos | |
| LJK83 | p-AtPXR::SEQ ID NO7::c-LUC::t-nos | |
| LJK84 | p-AtPXR::SEQ ID NO5::c-LUC::t-nos | |
| LJK85 | p-AtPXR::SEQ ID NO3::c-LUC::t-nos | |
| LJK86 | p-AtPXR::SEQ ID NO12::c-LUCA-nos | |
| LJK87 | p-AtPXR::SEQ ID NO19::c-LUCA-nos | |
| LJK88 | p-AtPXR::SEQ ID NO4::c-LUC::t-nos | |
| LJK90 | p-AtPXR::SEQ ID NO14::c-LUCA-nos | |

The resulting vectors were subsequently used to generate transgenic *A. thaliana* plants.

Example 2: Screening for NEENA Molecules Enhancing Gene Expression in Transgenic *A. thaliana* Plants This example illustrates that only selected NEENA candidate molecules are capable of enhancing gene expression.

All binary constructs containing the selected NEENA candidate molecules described in example 1 were stably transformed into *Arabidopsis thaliana* plants along with a NEENA-less control construct. In order to generate transgenic *A. thaliana* plants, *Agrobacterium tumefadiens* (strain C58C1 pGV2260) was transformed with the various vector constructs described above. For *A. thaliana* transformation, the Floral Dip method was employed (Clough and Bent, 1998, Plant Journal 16: 735-743). T1 transgenic plants were selected by germinating and growing seedlings on Kanamycin. After 12 days, cotyledons of transformants and wild-type control plants were sampled and distributed in 96 well plates preloaded with 50 microl 0.5× Murashige-Skoog Medium and subjected to Luciferase reporter gene assays (amended protocol after Weigel and Glazebrook, 2002, *Arabidopsis*, a laboratory manual, Cold Spring Harbor Laboratory Press, Chapter 7, ISBN 0-87969-572-2). Luminescence of cotyledons was determined in a solution containing 0.1 mM D-Luciferin (Cat No: L-8220, BioSynth, Staad, Switzerland) and 0.01% Tween20 (Sigma Aldrich, St. Louis, USA) in a MicroLumat Plus LB96V (Berthold Technologies, Bad Wildbad, Germany) recorded at 60 min after D-Luciferin addition. Instrument readings were averaged for each construct and based on these average expression values, fold change values were calculated to assess the impact of presence of a putative NEENA over reporter gene constructs lacking the respective putative NEENA. In comparison to seed specific p-AtPXR promoter-only NEENA-less reporter gene constructs, the 19 tested NEENA candidates containing constructs showed negative as well as positive effects, ranging from 0.8-fold to 22.2-fold induction in Luciferase activity (FIG. 1). In total, 15 putative NEENA molecules comprising sequences with SEQ ID NO1, NO2, NO3, NO4, NO5, NO6, NO7, NO8, NO9, NO10, NO11, NO12, NO13, NO14 and NO15 conferred a greater than 2.5-fold increase in gene expression based on luciferase reporter gene activity compared to the NEENA-less promoter-only reporter gene construct (FIG. 1) and hence are functional NEENA molecules. Since a number of the tested NEENA candidate molecules have marginal or even negative effects on the enhancement of gene expression, not all putative NEENA molecules are mediating a common stimulatory effect, but rather that the selected NEENA sequences convey significant enhancement of gene expression (SEQ ID NO 1 to 15).

Example 3: Test of NEENA Molecules for Seed Specific Enhancement of Gene Expression in Oilseed Rape Plants This example illustrates that NEENA molecules can be used across species to enhance gene expression of a tissue specific promoter compared to a NEENA-less promoter-only approach.

NEENA molecules mediating the strongest enhancement in gene expression in the pre-screening (cp. Example 2, SEQ ID NO1, NO2, NO3, NO4, NO5, NO6 and NO7) were selected for determining the enhancement on gene expression levels in transgenic oilseed rape plants.

3.1 Vector Construction for *B. napus* Plant Transformation

For transformation of oilseed rape plants, reporter gene expression cassettes without and with gene expression control molecules (SEQ IDs NO1-NO7) were combined with a gene expression cassette carrying a selectable marker gene for detecting transgenic plant lines within a pENTR/C vector. By performing a site specific recombination (LR-reaction), as previously described (see above, 1.3), the pENTR/A, pENTR/B and the pENTR/C carrying the selectable marker cassette were combined with the pSUN destination vector according to the manufacturers (Invitrogen, Carlsbad, Calif., USA) Multisite Gateway manual. The reactions yielded one binary vector with p-AtPXR promoter, the firefly luciferase coding sequence c-LUC, the t-nos terminator and the selectable marker cassette as well as 7 vectors harboring SEQ ID NO1, NO2, NO3, NO4, NO5, NO6 and NO7 immediately upstream of the firefly luciferase coding sequence (Table 6), for which the combination with SEQ ID NO1 is given exemplary (SEQ ID NO62). Except for varying SEQ ID NO2 to NO7, the nucleotide sequence is identical in all vectors (Table 6). The resulting plant transformation vectors are summarized in table 6:

TABLE 6

Plant expression vectors for *B. napus* transformation

| plant expression vector | Composition of the expression cassette Promoter::SEQ ID NO::reporter gene::terminator | SEQ ID NO |
|---|---|---|
| LJK148 | p-AtPXR::-::c-LUC::t-nos | |
| LJK156 | p-AtPXR::SEQ ID NO1::c-LUC::t-nos | 62 |
| LJK157 | p-AtPXR::SEQ ID NO2::c-LUC::t-nos | |
| LJK158 | p-AtPXR::SEQ ID NO7::c-LUC::t-nos | |
| LJK159 | p-AtPXR::SEQ ID NO5::c-LUC::t-nos | |
| LJK160 | p-AtPXR::SEQ ID NO4::c-LUC::t-nos | |
| LJK161 | p-AtPXR::SEQ ID NO6::c-LUC::t-nos | |
| LJK162 | p-AtPXR::SEQ ID NO3::c-LUC::t-nos | |

3.2 Generation of Transgenic Rapeseed Plants (Amended Protocol According to Moloney et al., 1992, Plant Cell Reports, 8: 238-242).

In preparation for the generation of transgenic rapeseed plants, the binary vectors were transformed into *Agrobacterium tumefaciens* C58C1:pGV2260 (Deblaere et al., 1985, Nucl. Acids. Res. 13: 4777-4788). A 1:50 dilution of an overnight culture of *Agrobacteria* harboring the respective binary construct was grown in Murashige-Skoog Medium (Murashige and Skoog, 1962, Physiol. Plant 15, 473) supplemented with 3% saccharose (3MS-Medium). For the transformation of rapeseed plants, petioles or hypocotyledons of sterile plants were incubated with a 1:50 *Agrobacterium* solution for 5-10 minutes followed by a three-day co-incubation in darkness at 25° C. on 3 MS. Medium supplemented with 0.8% bacto-agar. After three days, the explants were transferred to MS-medium containing 500 mg/l Claforan (Cefotaxime-Sodium), 100 nM Imazetapyr, 20 microM Benzylaminopurin (BAP) and 1.6 g/l Glucose in a 16 h light/8 h darkness light regime, which was repeated in weekly periods. Growing shoots were transferred to MS-Medium containing 2% saccharose, 250 mg/l Claforan and 0.8% Bacto-agar. After 3 weeks, the growth hormone 2-Indolbutyl acid was added to the medium to promote root formation. Shoots were transferred to soil following root development, grown for two weeks in a growth chamber and grown to maturity in greenhouse conditions.

3.3 Plant Analysis

Tissue samples were collected from the generated transgenic plants from leaves, flowers and seeds of varying developmental stages, stored in a freezer at −80° C. subjected to a Luciferase reporter gene assay (amended protocol after Ow et al., 1986). After grinding, the frozen tissue samples were resuspended in 800 microl of buffer 1 (0.1 M Phosphate buffer pH7.8, 1 mM DTT (Sigma Aldrich, St. Louis, Mo., USA), 0.05% Tween 20 (Sigma Aldrich, St. Louis, Mo., USA) followed by centrifugation at 10 000 g for 10 min. 75 microl of the aqueous supernatant were transferred to 96-well plates. After addition of 25 microl of buffer 11 (80 mM gycine-glycyl (Carl Roth, Karlsruhe, Germany), 40 mM MgSO4 (Duchefa, Haarlem, The Netherlands), 60 mM ATP (Sigma Aldrich, St. Louis, Mo., USA), pH 7.8) and D-Luciferin to a final concentration of 0.5 mM (Cat No: L-8220, BioSynth, Staad, Switzerland), luminescence was recorded in a MicroLumat Plus LB96V (Berthold Technologies, Bad Wildbad, Germany) yielding the unit relative light unit RLU per minute (RLU/min).

In order to normalize the luciferase activity between samples, the protein concentration was determined in the aqueous supernatant in parallel to the luciferase activity (adapted from Bradford, 1976, Anal. Biochem. 72, 248). 5 microl of the aqueous cell extract in buffer I were mixed with 250 microl of Bradford reagent (Sigma Aldrich, St. Louis, Mo., USA), incubated for 10 min at room temperature. Absorption was determined at 595 nm in a plate reader (Thermo Electron Corporation, Multiskan Ascent 354). The total protein amounts in the samples were calculated with a previously generated standard concentration curve. Values resulting from a ratio of RLU/min and mg protein/ml sample were averaged for transgenic plants harboring identical constructs and fold change values were calculated to assess the impact of NEENA molecule presence over NEENA-less reporter gene constructs.

3.4 NEENA Sequences Mediate Strong Enhancement of Gene Expression in Oilseed Rape Seeds For assessing the potential of enhancing gene expression of selected NEENA molecules (SEQ ID NO1, NO2, NO3, NO4, NO5, NO6, NO7) in oilseed rape seeds, seeds of identical developmental stages were collected from individual transgenic oilseed rape plant lines harboring either a promoter-only reporter gene construct or Luciferase reporter gene constructs containing a NEENA (SEQ ID NO1, NO2, NO3, NO4, NO5, NO6 or NO7). 10 seeds were collected from each transgenic event, processed and analyzed for Luciferase activity as described above (Example 3.3).

Figure 2:
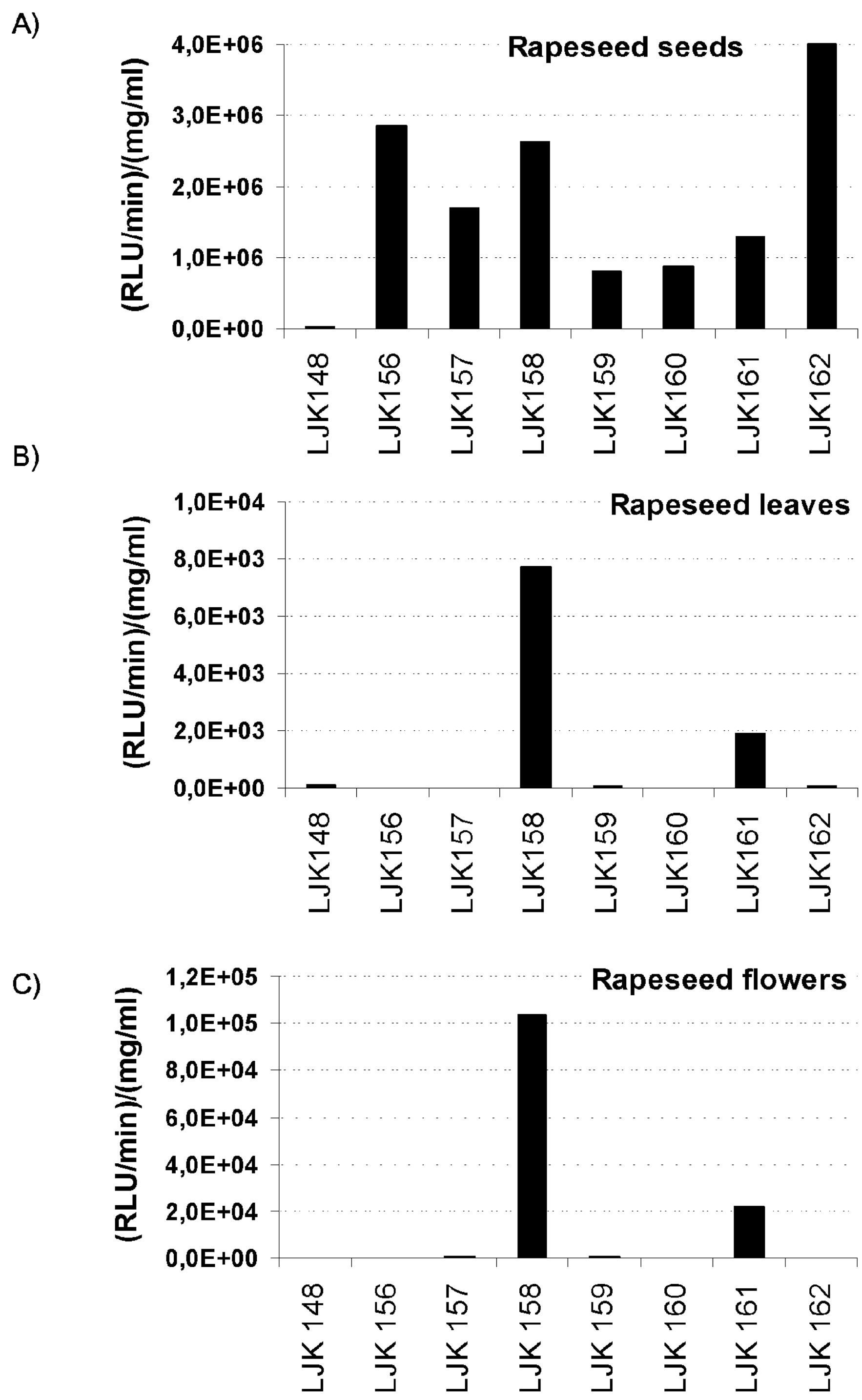
FIG. 2: Bar graphs of the luciferase reporter gene activity shown as relative light units (RLU) of independent transgenic oilseed rape plant lines harboring NEENA-less (LJK148) or NEENA-containing reporter gene constructs representing NEENA molecules from seed-preferred expressed genes (LJK156-LJK162) under the control of the p-AtPXR promoter and after normalization against the protein content of each sample. Expression values of plants harboring NEENA-containing constructs are shown in relation to plants expressing the NEENA-less control construct (LJK148) (averaged values, tissues of 20 independent transgenic plants analyzed). A) seed, B) leaf tissue, C) flowers.

In comparison to seed specific p-AtPXR promoter-only NEENA-less reporter gene constructs, the 7 tested NEENA molecules all mediated strong enhancements in gene expression, ranging from 54-fold to 380-fold induction in Luciferase activity in canola seeds (FIG. 2*a*). Comparable enhancement of expression was detected in oilseed rape seeds in later maturation stages (data not shown).

3.5 NEENA Molecules Boost Gene Expression Tissue Specifically in Oilseed Rape Seeds To assess the tissue specific enhancement of gene expression mediated by the NEENA molecules (SEQ ID NO1, NO2, NO3, NO4, NO5, NO6 or NO7), Luciferase activity was determined in fully developed leaves and open flowers of the transgenic oilseed rape plants harboring the reporter gene constructs outlined above. Three leaf samples of identical size as well as a whole flower were collected from each plant separately and subjected to Luciferase reporter gene assays as described above (Example 3.3). 5 (Seq. ID NO1, NO2, NO3, NO4, NO5) of the 7 tested NEENA molecules showed Luciferase expression levels comparable to that of the NEENA-less p-AtPXR promoter construct in leaves and flowers and thus do not alter the tissue specificity of the seed-specific p-AtPXR promoter (FIG. 2, band c). 2 NEENA molecules (SEQ ID NO6, NO7) slightly enhanced Luciferase activity in leaves and flowers of the analyzed oilseed rape plants (FIGS. 2, *b* and *c*) compared to plants comprising the NEENA-less construct. Hence, these NEENAs SEQ ID NO 6 and 7 are seed preferential NEENAs whereas the other NEENAs SEQ ID NO 1 to 5 are seed-specific NEENAs.

Example 4: Analysis of NEENA for Seed Specific Enhancement of Strong Seed Specific Promoters This example illuminates that the expression enhancing capabilities of NEENA molecules can be used in combination with a variety of promoter molecules in order to enhance tissue specific expression levels compared to that of promoters alone.

4.1 Vector Construction for *B. napus* Plant Transformation

Selected NEENA molecules of the group tested in example 3 (SEQ IDs NO1, NO2, NO3, NO5 and NO6) were tested for their effect on enhancing tissue specific gene expression of strong seed specific promoters p-LuPXR (WO2006089950, Sequence 9) and p-VfUSP (X56240, Baeumlein et al., 1991). Vector construction was performed as described above (cp. Example 1.3 and 3.1), with the primer sequences outlined in table 7 and vector LJB765 (WO2009016202) as DNA template. Positive pENTR/A clones underwent sequence analysis to ensure correctness of p-LuPXR and p-VfUSP promoters.

TABLE 7

Primer sequences for p-LuPXR and p-VfUSP

| Primer name | Sequence | SEQ ID NO. |
|---|---|---|
| p-LuPXR-for | ggggacaactttgtatagaaaagttcacgggcaggacatagggactactac | 63 |
| p-LuPXR-rev | ggggactgctttttgtacaaacttggatttatgataaaaatgtcggtttc | 64 |
| p-VfUSP-for | ggggacaactttgtatagaaaagttctgcagcaaatttacacattgccac | 65 |
| p-VfUSP-rev | ggggactgctttttgtacaaacttgactggctatgaagaaattataatc | 66 |

By performing a site specific recombination (LR-reaction) as previously described (see above, 1.3), the pENTR/A, pENTR/B vectors and the pENTR/C vector carrying the selectable marker cassette were combined with the pSUN destination vector according to the manufacturers (Invitrogen, Carlsbad, Calif., USA) Multisite Gateway manual. The reactions yielded 1 binary vector with p-LuPXR promoter, the firefly luciferase coding sequence and the t-nos terminator as well as the selectable marker cassette and 4 vectors harboring SEQ ID NO1, NO2, NO3 and NO6 immediately upstream of the firefly luciferase coding sequence (Table 8), for which the combination with SEQ ID NO1 is given exemplary (SEQ ID NO67). Except for varying SEQ ID NO2, NO3 and NO6, the nucleotide sequence is identical in all vectors (Table 8). Similarly, the p-VfUSP promoter was used to generate the promoter-only construct LJK219 as well as constructs LJK220, LJK221, LJK224 and LJK225 containing SEQ IDs NO1, NO2, NO3 and NO5 (Table 8). The resulting plant transformation vectors are summarized in table 8:

TABLE 8

Plant expression vectors for *B. napus* transformation

| plant expression vector | Composition of the expression cassette Promoter::SEQ ID NO::reporter gene::terminator | SEQ ID NO |
|---|---|---|
| LJK212 | p-LuPXR::-::c-LUC::t-nos | |
| LJK213 | p-LuPXR::SEQ ID NO1::c-LUC::t-nos | 67 |
| LJK214 | p-LuPXR::SEQ ID NO2::c-LUC::t-nos | |
| LJK215 | p-LuPXR::SEQ ID NO6::c-LUC::t-nos | |
| LJK218 | p-LuPXR::SEQ ID NO3::c-LUC::t-nos | |
| LJK219 | p-VfUSP::-::c-LUC::t-nos | |
| LJK220 | p-VfUSP::SEQ ID NO1::c-LUC::t-nos | |
| LJK221 | p-VfUSP::SEQ ID NO2::c-LUC::t-nos | |
| LJK224 | p-VfUSP::SEQ ID NO5::c-LUC::t-nos | |
| LJK225 | p-VfUSP::SEQ ID NO3::c-LUC::t-nos | |

4.2 NEENA Sequences Mediate Tissue Specific Enhancement of Gene Expression of Strong Seed Specific Promoters in Oilseed Rape Seeds Generation of transgenic rapeseed plants and plant analyses were conducted as described above (example 3.2 and 3.3).

In order to test the effect of selected NEENA molecules in combination with seed specific promoters (SEQ ID NO1, NO2, NO3, NO5 and NO6) in oilseed rape seeds, seeds of identical developmental stages were collected from individual transgenic oilseed rape plant lines harboring either a promoter-only reporter gene construct (LJK212 and LJK219) or Luciferase reporter gene constructs containing a NEENA (SEQ ID NO1, NO2, NO3, NO5 and NO6) (Table 9). From each transgenic event, 10 seeds were collected, processed and analyzed for Luciferase activity as described above (Example 3.3).

In comparison to seed specific p-LuPXR and p-VfUSP promoter-only NEENA-less reporter gene constructs, all tested NEENA molecules mediated strong enhancements in gene expression in oilseed rape seeds of medium maturity in combination with both, the p-LuPXR and p-VfUSP promoter (Table 9). Similar enhancement of expression was detected in oilseed rape seeds in later maturation stages.

TABLE 9

LUC expression in seeds of stably transformed oilseed rape plants.

| plant expression vector | Composition of the expression cassette Promoter::SEQ ID NO::reporter gene::terminator | LUC expression in oilseed rape seeds* | |
|---|---|---|---|
| LJK212 | p-LuPXR::-::c-LUC::t-nos | + | 20%** |
| LJK213 | p-LuPXR::SEQ ID NO1::c-LUC::t-nos | ++++ | 80% |
| LJK214 | p-LuPXR::SEQ ID NO2::c-LUC::t-nos | ++++ | 80% |
| LJK215 | p-LuPXR::SEQ ID NO6::c-LUC::t-nos | ++++ | 80% |
| LJK218 | p-LuPXR::SEQ ID NO3::c-LUC::t-nos | ++++ | 80% |
| LJK219 | p-VfUSP::-::c-LUC::t-nos | ++ | 40% |
| LJK220 | p-VfUSP::SEQ ID NO1::c-LUC::t-nos | +++++ | 100% |
| LJK221 | p-VfUSP::SEQ ID NO2::c-LUC::t-nos | +++++ | 100% |
| LJK224 | p-VfUSP::SEQ ID NO5::c-LUC::t-nos | ++++ | 80% |
| LJK225 | p-VfUSP::SEQ ID NO3::c-LUC::t-nos | +++++ | 100% |

*LUC expression given as a range of firefly luciferase activities (– no expression to +++++ very high expression), relative LUC expression compared to the expression of the linseed p-LuPXR promoter within the respective tissue.
**Relative luciferase expression compared to the expression controlled by the linseed peroxiredoxin promoter p-LuPXR.

To assess the tissue specific enhancement of gene expression mediated by the NEENA molecules (SEQ ID NO1, NO2, NO3, NO5 and NO6), Luciferase activity was determined in fully developed leaves of the transgenic oilseed rape plants harboring the reporter gene constructs outlined above. 3 leaf samples of identical size were collected from each plant separately and subjected to Luciferase reporter gene assays as described above (Example 3.2). The tissue specificities of the tested NEENA molecules (SEQ ID NO1, NO2, NO3, NO5, NO6) in combination with the p-LuPXR promoter and the p-VfUSP promoter resemble those tested with the p-AtPXR promoter analyzed above (example 3.5). As with the p-AtPXR promoter (example 3.5), the NEENA molecules (SEQ ID NO1, NO2, NO3 and NO5) showed no alteration of the tissue specificity of the p-LuPXR or p-VfUSP promoter (Table 10). Similar to the activity with the p-AtPXR promoter (example 3.5), the NEENA (SEQ ID NO6) conveyed enhancement of Luciferase activity in seeds, but also mediated Luciferase expression in the leaves of the analyzed oilseed rape plants (Table 10).

TABLE 10

LUC expression in leaves of stably transformed oilseed rape plants.

| plant expression vector | Composition of the expression cassette Promoter::SEQ ID NO::reporter gene::terminator | LUC expression in oilseed rape leaves* | |
|---|---|---|---|
| LJK212 | p-LuPXR::-::c-LUC::t-nos | – | 0%** |
| LJK213 | p-LuPXR::SEQ ID NO1::c-LUC::t-nos | – | 0% |
| LJK214 | p-LuPXR::SEQ ID NO2::c-LUC::t-nos | – | 0% |
| LJK215 | p-LuPXR::SEQ ID NO6::c-LUC::t-nos | + | 100% |
| LJK218 | p-LuPXR::SEQ ID NO3::c-LUC::t-nos | – | 0% |
| LJK219 | p-VfUSP::-::c-LUC::t-nos | – | 0% |
| LJK220 | p-VfUSP::SEQ ID NO1::c-LUC::t-nos | – | 0% |
| LJK221 | p-VfUSP::SEQ ID NO2::c-LUC::t-nos | – | 0% |
| LJK224 | p-VfUSP::SEQ ID NO5::c-LUC::t-nos | – | 0% |
| LJK225 | p-VfUSP::SEQ ID NO3::c-LUC::t-nos | – | 0% |

*LUC expression given as a range of firefly luciferase activities (– no expression to +++++ very high expression), relative LUC expression compared to the expression of the linseed p-LuPXR promoter within the respective tissue.
**Relative luciferase expression compared to the expression controlled by the linseed peroxiredoxin promoter p-LuPXR.

Example 5: Analysis of Tissue Specific Enhancement of Gene Expression in Soybean Plants This example illustrates that the claimed NEENA molecules can be used in a wide array of plant species and across species borders from different plant families to enhance gene expression tissue specifically compared to a NEENA-less promoter-only approach.

NEENA sequence molecules mediating the strongest enhancement in gene expression in the pre-screening (cp. Example 2, SEQ ID NO1, NO2, NO4, NO5, NO6 and NO7) were selected for determining the enhancement on gene expression levels in transgenic soybean plants. Plant expression vectors LJK148, LJK156, LJK157, LJK158, LJK159, LJK160 and LJK161 (cp. example 3.1) were used for stable soybean transformation.

5.1 Generation of Transgenic Soybean Plants (Amended Protocol According to WO2005/121345; Olhoft et al., 2007).

Soybean seed germination, propagation, *A. rhizogenes* and axillary meristem explant preparation, and inoculations were done as previously described (WO2005/121345; Olhoft et al., 2007) with the exception that the constructs LJK148, LJK156, LJK157, LJK158, LJK159, LJK160 and LJK161 (cp. example 3.1) each contained a mutated AHAS gene driven by the parsley ubiquitin promoter PcUbi4-2, mediating tolerance to imidazolinone herbicides for selection.

5.2 NEENA Sequences Mediate Strong Enhancement of Gene Expression in Soybean Plants Under Maintenance of Promoter Tissue Specificity Tissue samples were collected from the generated transgenic plants from leaves, flowers and seeds. The tissue samples were processed and analyzed as described above (cp. example 3.3)

Figure 3:
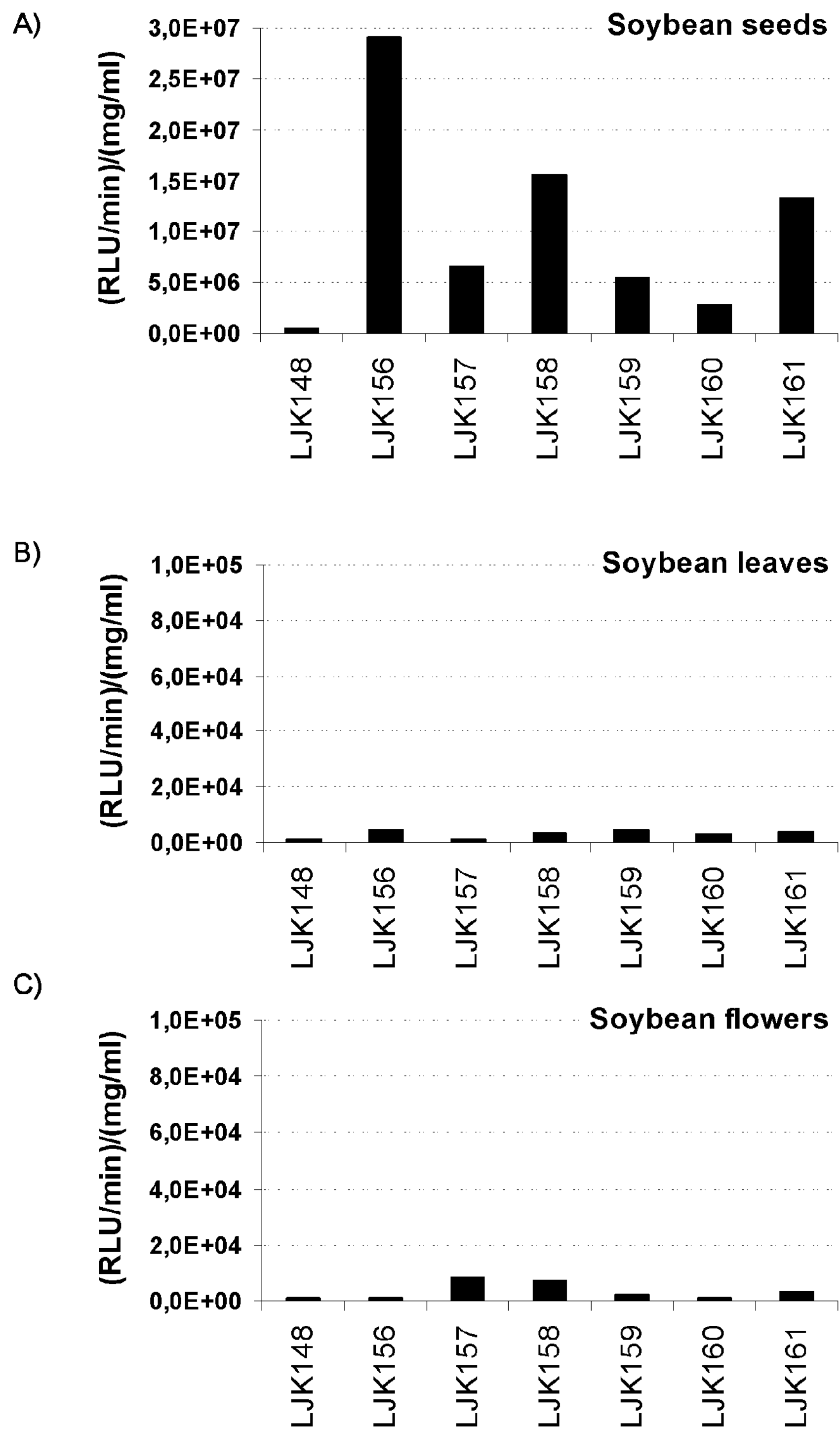
FIG. 3: Bar graphs of the luciferase reporter gene activity shown as relative light units (RLU) of independent transgenic soybean plant lines harboring NEENA-less (LJK148) or NEENA-containing reporter gene constructs representing NEENA molecules from seed-preferred expressed genes (LJK156-LJK161) under the control of the p-AtPXR promoter and after normalization against the protein content of each sample. Expression values of plants harboring NEENA-containing constructs are shown in relation to plants expressing the NEENA-less control construct (LJK148) (averaged values, tissues of 10 independent transgenic plants analyzed). A) seed B) leaf tissue, C) flowers.

In comparison to the seed-specific p-AtPXR promoter-only NEENA-less reporter gene construct LJK148, the seven tested NEENA molecules all mediated strong enhancements in gene expression in soybean seeds based on Luciferase activity (FIG. 3*a*). In contrast, no significant alterations in Luciferase activity mediated by NEENA molecules (SEQ ID NO1, NO2, NO4, NO5, NO6 and NO7) could be detected in soybean leaves and flowers (FIGS. 3, *b* and *c*).

Example 6: Analysis of NEENA Activity in Monocotyledonous Plants

This example describes the analysis of NEENA sequences with SEQ ID NO 1, 2, 3, 4, 5, 6 and 7 in monocotyledonous plants.

6.1 Vector Construction

For analyzing NEENA sequences with SEQ ID NO 1, 2, 3, 4, 5, 6 and 7 in monocotyledonous plants, a pUC-based expression vector harboring an expression cassette composed of the NEENA-less, seed specific monocotyledonous promoter p-KG86 from *Z. mais* is combined with a coding sequence of the beta-Glucuronidase (GUS) gene followed by the nopaline synthase (NOS) transcriptional terminator is used. Genomic DNA is extracted from *A. thaliana* green tissue using the Qiagen DNeasy Plant Mini Kit (Qiagen, Hilden, Germany). Genomic DNA fragments containing NEENA molecules are isolated by conventional polymerase chain reaction (PCR). Primers are designed on the basis of the *A. thaliana* genome sequence with a multitude of NEENA candidates. The reaction comprises 7 sets of primers (Table 11) and follows the protocol outlined by Phusion High Fidelity DNA Polymerase (Cat No F-540L, New England Biolabs, Ipswich, Mass., USA) using the following primers:

TABLE 11

Primer sequences

| Primer name | Sequence | SEQ ID NO | PCR yielding SEQ ID NO |
|---|---|---|---|
| NEENAss1_forII | aataatggcgcgcctggtgcttaaacactctggtgagt | 68 | 1 |
| NEENAss1_revII | aataatggcgcgcctttgacctacaaaatcaaagcagtca | 69 | |
| NEENAss2_forII | ttttttggcgcgccagttctttgctttcgaagttgc | 70 | 2 |
| NEENAss2_revII | ttttttggcgcgcctactacgtactgttttcaattct | 71 | |
| NEENAss4_forII | aataaaggcgcgccgtccagaattttctccattga | 72 | 6 |
| NEENAss4_revII | aataaaggcgcgcctcttcactatccaaagctctca | 73 | |
| NEENAss13_forII | ttttatggcgcgcctagcttaatctcagattcgaatcgt | 74 | 7 |
| NEENAss13_revII | ttttatggcgcgcctagtatctacataccaatcatacaaatg | 75 | |
| NEENAss14_forII | ttttttggcgcgcctttcacgatttggaatttga | 76 | 5 |
| NEENAss14_revII | ttttttggcgcgcctctacaacattaaaacgaccatta | 77 | |
| NEENAss15_forII | tatataggcgcgccagggtttcgtttttgtttca | 78 | 3 |
| NEENAss15_revII | tatataggcgcgccttatctcctgctcaaagaaacca | 79 | |
| NEENAss18_forII | tatataggcgcgccactgtttaagcttcactgtct | 80 | 4 |
| NEENAss18_revII | tatataggcgcgcctttcttctaaagctgaaagt | 81 | |

Amplification during the PCR and purification of the amplification products is carried out as detailed above (example 1.2). Following a DNA restriction digest with AscI (10 U/microl) restriction endonuclease, the digested products are purified with the Qiagen Gel Extraction Kit (Qiagen, Hilden, Germany).

NEENA PCR fragments (see above) are cloned separately upstream of the beta-Glucuronidase coding sequence using AscI restriction sites. The reaction yields one binary vector with the p-KG86 promoter, the beta-Glucuronidase coding sequence c-GUS and the t-nos terminator and seven vectors harboring SEQ ID NO1, NO2, NO3, NO4, NO5, NO6 and NO7, immediately upstream of the beta-Glucuronidase coding sequence (Table 12), for which the combination with SEQ ID NO1 is given exemplary (SEQ ID NO82). Except for varying SEQ ID NO2 to NO7, the nucleotide sequence is identical in all vectors (Table 12). The resulting vectors are summarized in table 12, with promoter molecules having the prefix p-, coding sequences having the prefix c-, and terminator molecules having the prefix t-.

TABLE 12

Plant expression vectors

| plant expression vector | Composition of the expression cassette Promoter::SEQ ID NO::reporter gene::terminator | SEQ ID NO |
|---|---|---|
| RTP2933 | p-KG86::-::c-GUS::t-nos | |
| LJK351 | p-KG86::SEQ ID NO1::c-GUS::t-nos | 82 |
| LJK352 | p-KG86::SEQ ID NO2::c-GUS::t-nos | |
| LJK353 | p-KG86::SEQ ID NO3::c-GUS::t-nos | |
| LJK354 | p-KG86::SEQ ID NO4::c-GUS::t-nos | |
| LJK355 | p-KG86::SEQ ID NO5::c-GUS::t-nos | |
| LJK356 | p-KG86::SEQ ID NO6::c-GUS::t-nos | |
| LJK357 | p-KG86::SEQ ID NO7::c-GUS::t-nos | |

The resulting vectors are used to analyze NEENA molecules in experiments outlined below (example 6.2).

6.2 Analysis of NEENA Molecules Enhancing Gene Expression in Monocotyledonous Plant Tissues These experiments are performed by bombardment of monocotyledonous plant tissues or culture cells (Example 6.2.1) or by *Agrobacterium*-mediated transformation (Example 6.2.2). The target tissue for these experiments can be plant tissues (e.g. leaf tissue), cultured plant cells (e.g. maize Black Mexican Sweetcorn (BMS), or plant embryos for *Agrobacterium* protocols.

6.2.1 Transient Assay Using Microprojectile Bombardment

The plasmid constructs are isolated using Qiagen plasmid kit (cat#12143). DNA is precipitated onto 0.6 microM gold particles (Bio-Rad cat#165-2262) according to the protocol described by Sanford et al. (1993) (Optimizing the biolistic process for different biological applications. Methods in Enzymology, 217: 483-509) and accelerated onto target tissues (e.g. two week old maize leaves, BMS cultured cells, etc.) using a PDS-1000/He system device (Bio-Rad). All DNA precipitation and bombardment steps are performed under sterile conditions at room temperature. Black Mexican Sweet corn (BMS) suspension cultured cells are propagated in BMS cell culture liquid medium [Murashige and Skoog (MS) salts (4.3 g/L), 3% (w/v) sucrose, myo-inositol (100 mg/L), 3 mg/L 2,4-dichlorophenoxyacetic acid (2,4-D), casein hydrolysate (1 g/L), thiamine (10 mg/L) and L-proline (1.15 g/L), pH 5.8]. Every week 10 mL of a culture of stationary cells are transferred to 40 mL of fresh medium and cultured on a rotary shaker operated at 110 rpm at 27° C. in a 250 mL flask.

60 mg of gold particles in a siliconized Eppendorf tube are resuspended in 100% ethanol followed by centrifugation for 30 seconds. The pellet is rinsed once in 100% ethanol and twice in sterile water with centrifugation after each wash. The pellet is finally resuspended in 1 mL sterile 50% glycerol. The gold suspension is then divided into 50 microL aliquots and stored at 4° C. The following reagents are added to one aliquot: 5 microL of 1 microg/microL total DNA, 50 microL 2.5 M $CaCl_2$, 20 microL 0.1 M spermidine, free base. The DNA solution is vortexed for 1 minute and placed at −80° C. for 3 min followed by centrifugation for 10 seconds. The supernatant is removed. The pellet is carefully resuspended in 1 mL 100% ethanol by flicking the tube followed by centrifugation for 10 seconds. The supernatant is removed and the pellet is carefully resuspended in 50 microL of 100% ethanol and placed at −80° C. until used (30 min to 4 hr prior to bombardment). If gold aggregates are visible in the solution the tubes are sonicated for one second in a waterbath sonicator just prior to use.

For bombardment, two-week-old maize leaves are cut into pieces approximately 1 cm in length and placed ad-axial side up on osmotic induction medium M-N6-702 [N6 salts (3.96 g/L), 3% (w/v) sucrose, 1.5 mg/L 2,4-dichlorophenoxyacetic acid (2,4-D), casein hydrolysate (100 mg/L), and L-proline (2.9 g/L), MS vitamin stock solution (1 mL/L), 0.2 M mannitol, 0.2 M sorbitol, pH 5.8]. The pieces are incubated for 1-2 hours.

In the case of BMS cultured cells, one-week-old suspension cells are pelleted at 1000 g in a Beckman/Coulter Avanti J25 centrifuge and the supernatant is discarded. Cells are placed onto round ash-free No 42 Whatman filters as a 1/16 inch thick layer using a spatula. The filter papers holding the plant materials are placed on osmotic induction media at 27° C. in darkness for 1-2 hours prior to bombardment. Just before bombardment the filters are removed from the medium and placed onto on a stack of sterile filter paper to allow the calli surface to partially dry.

Each plate is shot with 6 microL of gold-DNA solution twice, at 1,800 psi for the leaf materials and at 1,100 psi for the BMS cultured cells. To keep the position of plant materials, a sterilized wire mesh screen is laid on top of the sample. Following bombardment, the filters holding the samples are transferred onto M-N6-702 medium lacking mannitol and sorbitol and incubated for 2 days in darkness at 27° C. prior to transient assays.

The transient transformation via microprojectile bombardment of other monocotyledonous plants are carried out using, for example, a technique described in Wang et al., 1988 (Transient expression of foreign genes in rice, wheat and soybean cells following particle bombardment. Plant Molecular Biology, 11(4), 433-439), Christou, 1997 (Rice transformation: bombardment. Plant Mol Biol. 35 (1-2)).

Expression levels of the expressed genes in the constructs described above (example 6.1) are determined by GUS staining, quantification of luminescence/fluorescence, RT-PCR, protein abundance (detection by specific antibodies) or metabolic products generated via the expression cassettes described above using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining. Analyses of luciferase activities are performed as described above (see example 2 and 3.3).

In comparison to seed specific p-ZmKG86 promoter-only NEENA-less reporter gene constructs, the NEENA molecules all mediate strong enhancement in gene expression in these assays.

6.2.2 Transformation and Regeneration of Monocotyledonous Crop Plants

The *Agrobacterium*-mediated plant transformation using standard transformation and regeneration techniques may also be carried out for the purposes of transforming crop plants (Gelvin and Schilperoort, 1995, Plant Molecular Biology Manual, 2nd Edition, Dordrecht: Kluwer Academic Publ. ISBN 0-7923-2731-4; Glick and Thompson (1993) Methods in Plant Molecular Biology and Biotechnology, Boca Raton: CRC Press, ISBN 0-8493-5164-2). The transformation of maize or other monocotyledonous plants can be carried out using, for example, a technique described in U.S. Pat. No. 5,591,616. The transformation of plants using particle bombardment, polyethylene glycol-mediated DNA uptake or via the silicon carbonate fiber technique is described, for example, by Freeling & Walbot (1993) "The maize handbook" ISBN 3-540-97826-7, Springer Verlag New York).

Expression levels of the expressed genes are determined by GUS staining, quantification of luminescence or fluorescence, RT-PCR or protein abundance (detection by specific antibodies) using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining. Analyses of luciferase activities are performed as described above (examples 2 and 3.3).

In comparison to seed specific p-ZmKG86 promoter-only NEENA-less reporter gene constructs, the NEENA molecules mediate strong and tissue specific enhancement in gene expression in plants.

Example 7: Quantitative Analysis of NEENA Activity in Monocotyledonous Plants This example describes the analysis of NEENA sequences with SEQ ID NO 1 and 2 in corn plants.

7.1 Vector Construction

For analyzing NEENA sequences with SEQ ID NO 1 and 2 in monocotyledonous plants quantitatively, a pUC-based expression vector harboring an expression cassette composed of the NEENA-less, seed specific monocotyledonous promoter p-KG86 from *Z. mais* was combined with a coding sequence of the firefly luciferase (LUC) gene (Promega, Madison, Wis., USA) followed by the nopaline synthase (NOS) transcriptional terminator. Genomic DNA was extracted from *A. thaliana* green tissue using the Qiagen DNeasy Plant Mini Kit (Qiagen, Hilden, Germany). Genomic DNA fragments containing NEENA molecules were isolated by conventional polymerase chain reaction (PCR). Primers were designed on the basis of the *A. thaliana* genome sequence with a multitude of NEENA candidates. The reaction comprised 2 sets of primers (Table 11) and followed the protocol outlined by Phusion High Fidelity DNA Polymerase (Cat No F-540L, New England Biolabs, Ipswich, Mass., USA) using the following primers:

TABLE 11

| Primer sequences | | | |
|---|---|---|---|
| Primer name | Sequence | SEQ ID No | PCR yielding SEQ ID NO |
| NEENAss1_forIII | atatacgcgtggtgcttaaacactctggtgagt | 83 | 1 |
| NEENAss1_revIII | atatggcgcgcctttgacctacaaaatcaaagcagtca | 84 | |
| NEENAss2_forIII | atatacgcgtagttctttgctttcgaagttgc | 85 | 2 |
| NEENAss2_revIII | atatggcgcgcctactacgtactgttttcaattct | 86 | |

Amplification during the PCR and purification of the amplification products was carried out as detailed above (example 1.2). Following a DNA restriction digest with MluI (10 U/microl) and AscI (10 U/microl) restriction endonucleases, the digested products were purified with the Qiagen Gel Extraction Kit (Qiagen, Hilden, Germany).

NEENA PCR fragments (see above) were cloned separately upstream of the firefly luciferase coding sequence using AscI restriction sites. The reaction yielded one binary vector with the p-KG86 promoter, the firefly luciferase coding sequence c-LUC and the t-nos terminator and two vectors harboring SEQ ID NO1 and NO2, immediately upstream of the firefly luciferase coding sequence (Table 12), for which the combination with SEQ ID NO1 is given exemplary (SEQ ID NO87). Except for varying SEQ ID NO2, the nucleotide sequence is identical in the vectors (Table 12). The resulting vectors are summarized in table 12, with promoter molecules having the prefix p-, coding sequences having the prefix c-, and terminator molecules having the prefix t-.

TABLE 12

| Plant expression vectors | | |
|---|---|---|
| plant expression vector | Composition of the expression cassette Promoter::SEQ ID NO::reporter gene::terminator | SEQ ID NO |
| RTP5679 | p-KG86::-::c-LUC::t-nos | |
| RTP5683 | p-KG86::SEQ ID NO1::c-LUC::t-nos | 87 |
| RTP5684 | p-KG86::SEQ ID NO2::c-LUC::t-nos | |

The resulting vectors were used to analyze NEENA molecules in experiments outlined below (Example 7.2).

7.2 Generation of Transgenic Maize Plants

Maize germination, propagation, *A. tumefaciens* preparation and inoculations were done as previously described (WO2006136596, US20090249514) with the exception that the constructs RTP5679, RTP5683 and RTP5684 (cp. example 7.1) each contained a mutated AHAS gene driven by the corn ubiquitin promoter p-Ubi, mediating tolerance to imidazolinone herbicides for selection.

7.3 NEENA Sequences Mediate Strong and Tissue Specific Enhancement of Gene Expression in Corn Plants Tissue samples were collected from the generated transgenic plants from leaves and kernels. The tissue samples were processed and analyzed as described above (cp. example 3.3)

Figure 4:
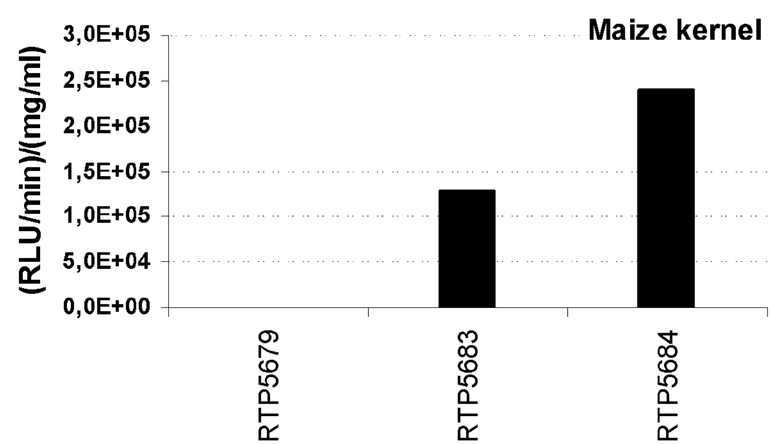
FIG. 4: Bar graph of the luciferase reporter gene activity shown as relative light units (RLU) of independent transgenic maize plant lines harboring NEENA-less (RTP5679) or NEENA-containing reporter gene constructs representing NEENA molecules from seed-preferred expressed genes (RTP5683-RTP5684) under the control of the p-KG86 promoter and after normalization against the protein content of each sample (averaged values, tissues of 15 independent transgenic plants analyzed). A) kernel, B) leaf tissue.
Figure 4:
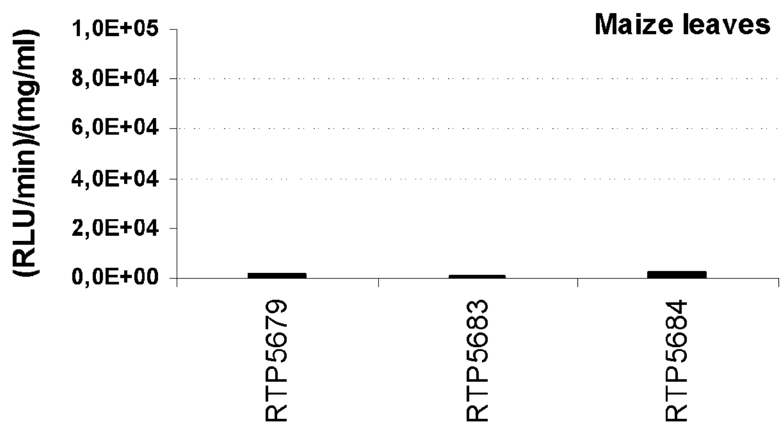

In comparison to the seed-specific p-KG86 promoter-only NEENA-less reporter gene construct, the two tested NEENA molecules (SEQ ID NO1 and NO2) mediated strong enhancements in gene expression in kernel (FIG. 4*a*). In contrast, no significant alterations in Luciferase activity mediated by NEENA molecules (SEQ ID NO1 and NO2) could be detected in maize leaves (FIG. 4*b*).

Example 8: Quantitative Analysis of NEENA Activity in Rice Plants

This example describes the analysis of NEENA sequences with SEQ ID NO 1 and 2 in rice plants.

8.1 Vector Construction

For analyzing NEENA sequences with SEQ ID NO 1 and 2 in rice plants quantitatively, pENTR/B vectors LJK1, LJK19 and LJK20 (compare example 1.3) were combined with a destination vector harboring the seed preferred rice PRO0090 promoter upstream of the recombination site using site specific recombination (LR-reaction) according to the manufacturers (Invitrogen, Carlsbad, Calif., USA) Gateway manual. The reactions yielded one binary vector with PRO0090 promoter, the firefly luciferase coding sequence c-LUC and the t-nos terminator as well as 2 vector harboring SEQ ID NO1 and NO2 immediately upstream of the firefly luciferase coding sequence (Table 13). Except for varying SEQ ID NO2, the nucleotide sequence is identical in the vectors (Table 13). The resulting vectors are summarized in table 13, with promoter molecules having the prefix p-, coding sequences having the prefix c-, and terminator molecules having the prefix t-.

TABLE 13

| Plant expression vectors | | |
|---|---|---|
| plant expression vector | Composition of the expression cassette Promoter::SEQ ID NO::reporter gene::terminator | SEQ ID NO |
| CD30977 | p-PRO0090::-::c-LUC::t-nos | |
| CD30971 | p-PRO0090::SEQ ID NO1::c-LUC::t-nos | — |
| CD30972 | p-PRO0090::SEQ ID NO2::c-LUC::t-nos | — |

The resulting vectors were used to analyze NEENA molecules in experiments outlined below (Example 8.2).

8.2 Generation of Transgenic Rice Plants

The *Agrobacterium* containing the respective expression vector was used to transform *Oryza sativa* plants. Mature dry seeds of the rice *japonica* cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the respective expression vector was used for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

8.3 NEENA Sequences Mediate Strong and Tissue Specific Enhancement of Gene Expression in Rice Plants Tissue samples were collected from the generated transgenic plants from leaves and seeds. The tissue samples were processed and analyzed as described above (cp. example 3.3)

Figure 5:
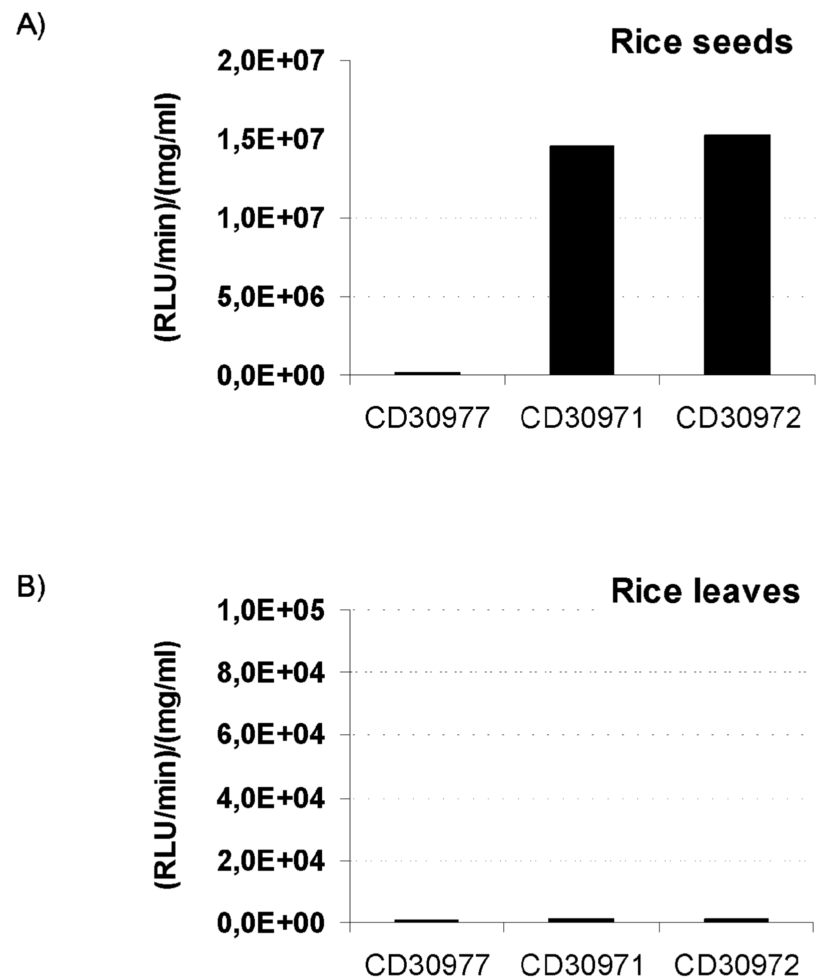
FIG. 5: Bar graph of the luciferase reporter gene activity shown as relative light units (RLU) of independent transgenic rice plant lines harboring NEENA-less (CD30977) or the NEENA-containing reporter gene construct representing a NEENA molecule from seed-preferred expressed genes (CD30971-CD30972) under the control of the rice PRO0090 promoter and after normalization against the protein content of each sample (averaged values, tissues of 15 independent transgenic plants analyzed). A) seeds, B) leaf tissue.

In comparison to the seed-specific PRO0090 promoter-only NEENA-less reporter gene construct, the tested NEENA molecules (SEQ ID NO 1 and NO2) mediated strong enhancements in gene expression in seeds (FIG. 5*a*). In contrast, no significant alterations in Luciferase activity mediated by NEENA molecules (SEQ ID NO1 and NO2) could be detected in rice leaves (FIG. 5*b*).

We claim:

1. A method for production of a high expression seed-specific expression construct, comprising functionally linking one or more nucleic acid expression enhancing nucleic acid (NEENA) molecules to a seed-specific promoter and to a nucleic acid molecule to be expressed under the control of said seed-specific promoter, wherein said NEENA is heterologous to said seed-specific promoter and said nucleic acid molecule, and wherein said NEENA comprises the nucleic acid sequence of SEQ ID NO: 4.

2. A method for producing a plant or part thereof with enhanced seed-specific expression of one or more nucleic acid molecule compared to a respective control plant or part thereof, comprising:

a) introducing one or more NEENA as defined in claim 1 into a plant cell, plant, or part thereof;

b) integrating said one or more NEENA into the genome of said plant cell, plant, or part thereof to produce a transformed plant cell, whereby said one or more NEENA is functionally linked to an endogenous seed-specific expressed nucleic acid heterologous to said one or more NEENA; and c) regenerating a plant or part thereof comprising said one or more NEENA from said transformed plant cell.

3. The method of claim 2, wherein the plant is a monocot or dicot plant.

4. The method of claim 2, wherein said one or more NEENA is functionally linked to the endogenous seed-specific expressed nucleic acid 2500 bp or fewer away from the transcription start site of said nucleic acid.

5. The method of claim 2, wherein said one or more NEENA is functionally linked to the endogenous seed-specific expressed nucleic acid upstream of the translational start site of the nucleic acid.

6. The method of claim 2, wherein said one or more NEENA is functionally linked to the endogenous seed-specific expressed nucleic acid within the 5'UTR of the nucleic acid.

7. A method for producing a plant or part thereof with enhanced seed-specific expression of one or more nucleic acid molecule compared to a respective control plant or part thereof, comprising:

a) providing an expression construct comprising one or more NEENA as defined in claim 1 functionally linked to a seed-specific promoter and to a nucleic acid molecule under the control of said seed-specific promoter, wherein said seed-specific promoter and said nucleic acid molecule are heterologous to said one or more NEENA;

b) integrating said expression construct into the genome of a plant or part thereof to produce a transformed plant or part thereof; and c) regenerating a plant or part thereof comprising said expression construct from said transformed plant or part thereof.

8. The method of claim 7, wherein the plant is a monocot or dicot plant.

9. The method of claim 7, wherein said one or more NEENA is functionally linked to the seed-specific promoter 2500 bp or fewer away from the transcription start site of said nucleic acid molecule.

10. The method of claim 7, wherein said one or more NEENA is functionally linked to the seed-specific promoter upstream of the translational start site of the nucleic acid molecule, and wherein the expression of said nucleic acid molecule is under the control of said seed-specific promoter.

11. The method of claim 7, wherein said one or more NEENA is functionally linked to the seed-specific promoter within the 5'UTR of the nucleic acid molecule, and wherein the expression of said nucleic acid molecule is under the control of said seed-specific promoter.

12. A recombinant expression construct comprising one or more NEENA functionally linked to a seed-specific promoter and to a nucleic acid molecule to be expressed under the control of said seed-specific promoter, wherein said NEENA is heterologous to said seed-specific promoter and said nucleic acid molecule, and wherein said NEENA comprises the nucleic acid sequence of SEQ ID NO: 4.

13. A recombinant expression vector comprising one or more recombinant expression construct of claim 12.

14. A transgenic plant cell, plant, or part thereof comprising one or more NEENA functionally linked to a seed-specific promoter and to a nucleic acid molecule to be expressed under the control of said seed-specific promoter, wherein said NEENA is heterologous to said seed-specific promoter and said nucleic acid molecule, and wherein said NEENA comprises the nucleic acid sequence of SEQ ID NO: 4.

15. A transgenic cell, plant, or part thereof comprising:

a) the recombinant expression construct of claim 12; or b) a recombinant expression vector comprising one or more of said recombinant expression construct.

16. The transgenic cell of claim 15, selected or derived from the group consisting of bacteria, fungi, yeasts, and plants.

17. The transgenic plant or part thereof of claim 15, wherein said plant is a monocot or dicot plant.

18. A transgenic cell, cell culture, seed, plant, plant part, or propagation material derived from the transgenic cell, plant, or part thereof of claim 15, wherein the transgenic cell, cell culture, seed, plant, plant part, or propagation material comprises said NEENA.

19. A method for the production of foodstuffs, animal feed, seeds, a pharmaceutical or a fine chemical comprising:

a) providing a transgenic cell culture, seed, plant, plant part, or propagation material derived from the transgenic cell or plant of claim 18; and b) preparing foodstuffs, animal feed, seeds, a pharmaceutical or a fine chemical from the transgenic cell culture, seed, plant, plant part, or propagation material of a).

20. A method for enhancing seed-specific expression of one or more nucleic acid molecule in a plant compared to a respective control plant, comprising transiently introducing into a plant the recombinant expression construct of claim 12.

* * * * *

```
SEQUENCE LISTING

<160> NUMBER OF SEQ ID NOS: 87

<210> SEQ ID NO 1
<211> LENGTH: 847
<212> TYPE: DNA
<213> ORGANISM: Arabidopsis thaliana

<400> SEQUENCE: 1

tggtgcttaa acactctggt gagttctagt acttctgcta tgatcgatct cattaccatt      60

tcttaaattt ctctccctaa atattccgag ttcttgattt ttgataactt caggttttct     120

ctttttgata aatctggtct ttccattttt tttttttgt ggttaattta gtttcctatg     180

ttcttcgatt gtattatgca tgatctgtgt ttggattctg ttagattatg tattggtgaa     240

tatgtatgtg tttttgcatg tctggttttg gtcttaaaaa tgttcaaatc tgatgatttg     300

attgaagctt ttttagtgtt ggtttgattc ttctcaaaac tactgttaat ttactatcat     360

gttttccaac tttgattcat gatgacactt ttgttctgct ttgttataaa attttggttg     420

gtttgatttt gtaattatag tgtaattttg ttaggaatga acatgtttta atactctgtt     480

ttcgatttgt cacacattcg aattattaat cgataattta actgaaaatt catggttcta     540

gatcttgttg tcatcagatt atttgtttcg ataattcatc aaatatgtag tccttttgct     600

gatttgcgac tgtttcattt tttctcaaaa ttgtttttg ttaagtttat ctaacagtta     660

tcgttgtcaa aagtctcttt cattttgcaa aatcttcttt tttttttgt ttgtaacttt     720

gtttttaag ctacacattt agtctgtaaa atagcatcga ggaacagttg tcttagtaga     780

cttgcatgtt cttgtaactt ctatttgttt cagtttgttg atgactgctt tgattttgta     840

ggtcaaa                                                              847


<210> SEQ ID NO 2
<211> LENGTH: 455
<212> TYPE: DNA
<213> ORGANISM: Arabidopsis thaliana

<400> SEQUENCE: 2
```

```
agttctttgc tttcgaagtt gccgcaacct aaacaggttt ttccttcttc tttcttctta      60

ttaactacga ccttgtcctt tgcctatgta aaattactag gttttcatca gttacactga     120

ttaagttcgt tatagtggaa gataaaatgc cctcaaagca ttttgcagga tatctttgat     180

ttttcaaaga tatggaactg tagagtttga tagtgttctt gaatgtggtt gcatgaagtt     240

tttttggtct gcatgttatt ttttcctcga aatatgtttt gagtccaaca agtgattcac     300

ttgggattca gaaagttgtt ttctcaatat gtaacagttt ttttctatgg agaaaaatca     360

tagggaccgt tggttttggc ttctttaatt ttgagctcag attaaaccca ttttacccgg     420

tgttcttggc agaattgaaa acagtacgta gtacc                                455


<210> SEQ ID NO 3
<211> LENGTH: 758
<212> TYPE: DNA
<213> ORGANISM: Arabidopsis thaliana

<400> SEQUENCE: 3

agggtttcgt ttttgtttca tcgataaact caaaggtgat gattttaggg tcttgtgagt      60

gtgctttttt gtttgattct actgtagggt ttatgttctt tagctcatag gttttgtgta     120

tttcttagaa atgtggcttc tttaatctct gggtttgtga ctttttgtgt ggtttctgtg     180

tttttcatat caaaaaccta ttttttccga gttttttttt acaaattctt actctcaagc     240

ttgaatactt cacatgcagt gttcttttgt agattttaga gttaatgtgt taaaaagttt     300

ggatttttct tgcttataga gcttcttcac tttgattttg tgggtttttt tgttttaaag     360

gtgagatttt tgatgaggtt tttgcttcaa agatgtcacc tttctgggtt tgtcttttga     420

ataaagctat gaactgtcac atggctgacg caattttgtt actatgtcat gaaagctgac     480

gtttttccgt gttatacatg tttgcttaca cttgcatgcg tcaaaaaaat tggggctttt     540

tagttttagt caaagatttt acttctcttt tgggatttat gaaggaaagt tgcaaacttt     600

ctcaaatttt accattttttg ctttgatgtt tgtttagatt gcgacagaac aaactcatat     660

atgttgaaat ttttgcttgg ttttgtatag gattgtgtct tttgcttata aatgttgaaa     720

tctgaacttt ttttttgttt ggtttctttg agcaggag                             758


<210> SEQ ID NO 4
<211> LENGTH: 252
<212> TYPE: DNA
<213> ORGANISM: Arabidopsis thaliana

<400> SEQUENCE: 4

actgtttaag cttcactgtc tctgaatcgg caaaggtaaa cgtatcaatt attctacaaa      60

cccttttatt tttcttttga attaccgtct tcattggtta tatgataact tgataagtaa     120

agcttcaata attgaatttg atctgtgttt ttttggcctt aatactaaat ccttacataa     180

gctttgttgc ttctcctctt gtgagttgag tgttaagttg taataatggt tcactttcag     240

ctttagaaga aa                                                         252


<210> SEQ ID NO 5
<211> LENGTH: 377
<212> TYPE: DNA
<213> ORGANISM: Arabidopsis thaliana

<400> SEQUENCE: 5

tttcacgatt tggaatttga ttcctgcgat cacaggtatg acaggttaga ttttgttttg      60
```

```
tatagttgta tacatacttc tttgtgatgt tttgtttact taatcgaatt tttggagtgt    120

tttaaggtct ctcgtttaga aatcgtggaa aatatcactg tgtgtgtgtt cttatgattc    180

acagtgttta tgggtttcat gttctttgtt ttatcattga atgggaagaa atttcgttgg    240

gatacaaatt tctcatgttc ttactgatcg ttattaggag tttggggaaa aaggaagagt    300

ttttttggtt ggttcgagtg attatgaggt tatttctgta tttgatttat gagttaatgg    360

tcgttttaat gttgtag                                                   377


<210> SEQ ID NO 6
<211> LENGTH: 718
<212> TYPE: DNA
<213> ORGANISM: Arabidopsis thaliana

<400> SEQUENCE: 6

gtccagaatt ttctccattg aagctggatt ctaaggtcag ttcttacttc tttatctcaa     60

tctgatgatt ccatatcgaa agtcttactt tttcacttca atttcaatct gatgattcta    120

agatctttga ttcgaggtcg atctctgata gttactacat gtttctgggt ttatttattt    180

ttaatccata tagtaattaa aaactcttat gaggtttaat tatggttact tgagaatttg    240

caatcgtcat ctttctttga ctcctatcca ttttttggtt tttcctttgt ttaatttctg    300

tttcataatt gtaattgtaa attaaccaaa acaaattgat cagaaacctt tttcctatgg    360

aatatttatc acacgcaagc ctgtgagttg tgactctgta atcacttcct tgttctggta    420

atttcagtgg ttaaggctct ccttttttct gatgttgtca gcaaaagtta gtttttcttc    480

ttctttaatg ggttaattac acctaaatct ctggttatta aacaatccag aaagaaaaaa    540

agtttattcc ttcctctatg tatatagttt cacatgcaag catcacttgt ttgttctgac    600

aaattgcaga gttttgagtt ctgttttttt tttttctaa tgttttgtct ttaagaaagt    660

tctgtttttt tttctgcagg aaagttatca aaagttttga gagctttgga tagtgaag      718


<210> SEQ ID NO 7
<211> LENGTH: 495
<212> TYPE: DNA
<213> ORGANISM: Arabidopsis thaliana

<400> SEQUENCE: 7

ctagcttaat ctcagattcg aatcgttcca tagtggtgag cttcgtgttc ttctttcgtc     60

tcttactcct gattctcgat tttagggttt tcagtaattg cgtcggcggc gaaagtcttt    120

atcgccgatc gatcttcctt atctagaaat tattgatcag aaactgttgg gttttgtttg    180

attcttgtca agttttgatt tttcatgcga aattgctcaa tcccaattca aagttacgat    240

ttttattgaa aaccctagat tggtttcttc aagtttgtca ctttgattca atctaatagc    300

ttagcttaat cgttaagtct cttttttggt tttaggtttc atttgcgatt taaaggttct    360

tgttttggta tttgttttgc tttggtcctt taagtttgag aggcttatgt agattataag    420

agagaagagt attgctttgc atgtttaaag gaagaacttt taactgaaca tttgtatgat    480

tggtatgtag atact                                                     495


<210> SEQ ID NO 8
<211> LENGTH: 139
<212> TYPE: DNA
<213> ORGANISM: Arabidopsis thaliana

<400> SEQUENCE: 8

atttccacac gctttctatc atttccaccc aaaaggtaac gcgcttttta tttcctttcc     60
```

tgcattcata aatttgtctc ctgcatgttg aaaaaaaaaa atttacatcg agattcgttt 120
ttatttttta gagagagat 139

<210> SEQ ID NO 9
<211> LENGTH: 889
<212> TYPE: DNA
<213> ORGANISM: Arabidopsis thaliana

<400> SEQUENCE: 9
gtctactttc attacagtga ctctgcatgc ttcaggtctc gtctaattct tgaattctct 60
tcttttctgt tccgtaattt actttctagg gtctctagat ttgtgtctcc tctaacaaaa 120
gatcctatct ttcgacaaat ttaatttcat cattgacctt tgtcgattcc attctctctc 180
tatctctctg tttcttcgaa aacctagagg ttttgaattt aatgattcct ttttatgtca 240
ataaatttgc aatcaatggg agctttttaa aatcatcgtt atatctataa acaaaaaaac 300
agtaattact cttcttagat ctaaaacaat taataaatct ttcccttttt tctcatcata 360
attttttcgt atttaactct tgtaaaaatt tgcttagccg tttcgctttc tcaggcccca 420
ggtgattcgt gtcttctagg tcagcttgtg aaacctgaga gaagccatct tttgtttgcg 480
gttacaaact ttgccgcttc aatatttcat tgctgttttc tgggaaaacc tttttctagt 540
tttttcggct tattatgcct tttaactttt tgtgcattta acatttattg ttagtgcttt 600
gcttagtgta aagtagtagt tctctttgta atattaccat aaggttcaga agtaaatttt 660
tctaaaattg ttttcttgtg ggaaattcag actgatttca gcaacatgca tgggcttaaa 720
atcagcttct aagactgaga tttagtgacc agtgtggtgg tgtcttgttc tctgttcttg 780
ggagaacaca aaggcagtgt ggagtctggt gagttttctg attcttgaaa agatttataa 840
attttcttgc aaaattagtc tttatgttga attgtgttgc aggtaaaat 889

<210> SEQ ID NO 10
<211> LENGTH: 433
<212> TYPE: DNA
<213> ORGANISM: Arabidopsis thaliana

<400> SEQUENCE: 10
gcacaatctt agcttacctt gaatcacaac ttcaggtata tgtaactgat tctaaattga 60
agattgtgtg caaatcttat atccattttt tattattaaa tttattgaaa aagctagcgg 120
tgtaaattaa tgtcacaaaa tcagtatatt gttagttttt gtttttttttg aagttttatg 180 caaatcttca aaaagtatat tcagtgttgt aattgacaaa tagagactct agttcttttt 240 tttttttct tttttttaac atctgactct tatagagact ctagttcatg tacacttttt 300
ttaatggaaa aacaaatttg aaactgaata tcttatttcc acgtagattg tatattagtt 360
taatttgatt gttatatttg taaatgtcta ctaaacagga attggatggt gaggaggcaa 420
ggcttgtgga tta 433

<210> SEQ ID NO 11
<211> LENGTH: 354
<212> TYPE: DNA
<213> ORGANISM: Arabidopsis thaliana

<400> SEQUENCE: 11
atcttagggt ttcgcgagat ctcactctca ctggtatgtc tgtgtttctt cttccatttt 60
ctgtttctat tggaaacttc tctctccaat ttcgttttct tcacttcttt gatcctttag 120

```
ctttgacaaa accgtagtaa aggatcaaaa gttatcatct ttggtccatg ttgtgaatcg    180

tgctctgctt gggtcgtgac tcccaaatcc ggatttgaaa ccagcatatc tgagcttaat    240

tcgagcatgc atgcgcttct ttttttctga ttttttttag actttggttc taaatccctt    300

aactttggat taactgtcaa tctacaattt tatattaaca gagatagctt agca          354
```

<210> SEQ ID NO 12
<211> LENGTH: 143
<212> TYPE: DNA
<213> ORGANISM: Arabidopsis thaliana

<400> SEQUENCE: 12

```
cagaagctca tttcttcgat acgatcaacc attaggtgat ttttttctct gatcttcgag     60

ttctgataat tgctcttttt tctctggctt tgttatcgat aatttctctg gattttcttt    120

ctggggtgaa tttttgcgca gag                                            143
```

<210> SEQ ID NO 13
<211> LENGTH: 182
<212> TYPE: DNA
<213> ORGANISM: Arabidopsis thaliana

<400> SEQUENCE: 13

```
atttttgttg gtgaaaggta gaattcgtaa atttcttctg ctcactttat tgtttcgact     60

catacccgat aatctcttct atgtttggta gagatatctt ctcaaagtct tatctttcct    120

taccgtgttc tgtgtttttt gatgatttag gtgaagaaga agaagcagag acaaaaacga    180

tt                                                                   182
```

<210> SEQ ID NO 14
<211> LENGTH: 665
<212> TYPE: DNA
<213> ORGANISM: Arabidopsis thaliana

<400> SEQUENCE: 14

```
ttaagctttt aagaatctct actcacattt tctctgtgag tgttctttta tacttctttg     60

ttatttccaa tttttctttc tttcctctaa aaattttagg aactattgaa tcatttaatt    120

tctgtttgtt gataaaattt cgatcaactg ttctcggctt accgatgcat tttttgtaaa    180

accgtctttt tttggtgaat aaaattttaa attcatacaa aaaaaaaaca tatttgatac    240

tattttagct ccattgtatc tgaatcttca tttgttaatt tttttgtttc ctctgttctc    300

acttgaattt tggaatattt tctctaggtt ttaccttata ttcttcactt taagaactat    360

atgaagattt gattggaagt aataatattc ggtgatagaa tctgagtttg tttgattctg    420

gtgtggggct tatatctaac ttttttcttt gtaccaatac attttcaatt ttacattttt    480

gattagctta aaatgtgaag gataccttgt aaataactat tacactattg cttgtcttag    540

tctaatagtc ttcactaata ttttgtgcag tagaagtaaa tattataaag agttgttgtt    600

tgattataga gagttgttgt ctattcttta acttgatgtg atgttgtttt tgatgacagg    660

taaaa                                                                665
```

<210> SEQ ID NO 15
<211> LENGTH: 252
<212> TYPE: DNA
<213> ORGANISM: Arabidopsis thaliana

<400> SEQUENCE: 15

```
tctgggaaat atcgattttg atctattaag agctggtgag agccaaagtt tcctttttgt     60
```

```
ttgtttgttt gtttgtttgt tgtttgtatt tttgtatctc tgtgatcgct tctacgtgtt    120

gggtcatgca gagaaactca ttttgttttg atttgcaatg tgtcaattcc actttgaaat    180

ataagattca tcgcctctct ctcctttgtt ttttttcttc ttctgcagct acgagctttg    240

ggatgtggtg ag                                                        252
```

<210> SEQ ID NO 16
<211> LENGTH: 186
<212> TYPE: DNA
<213> ORGANISM: Arabidopsis thaliana

<400> SEQUENCE: 16

```
tattcacaat ctcctgccac ctctcatttc tctagttgag ttgttatctg cgtttttaag     60

cactcgaata ctgcatgcaa attccctgat tgtttgttag taccttagag attctcgatt    120

ttttagttgt ttagattgaa ccaggattac taaattgtta ttgttttctg tgtaaaggct    180

acatat                                                               186
```

<210> SEQ ID NO 17
<211> LENGTH: 345
<212> TYPE: DNA
<213> ORGANISM: Arabidopsis thaliana

<400> SEQUENCE: 17

```
ctttgcagct tctgcagcac ctctccctac tccaggtact tatgtttttg ataattttat     60

tgatagactc tttacaatta tacttaagct tgttactttt tattgttacc aacaaaagct    120

aatgtatagt tcataactca caggtcctgc gtctttcggt ccgaccactt ctcctacaga    180

ttcgcaaact tctgatcctg aaggtactcg cgaacttttt actgcaactt ctagttctaa    240

ctccaaaaca ttttgttcag aatttgtttc taaaagattt tcgggtttgt tgacgtcaca    300

taactcgcag ggtctgcttc tttccgtccg cccacttctc cgaca                    345
```

<210> SEQ ID NO 18
<211> LENGTH: 285
<212> TYPE: DNA
<213> ORGANISM: Arabidopsis thaliana

<400> SEQUENCE: 18

```
aacaactatg gcctgagggt aacaagagta tcaggtatat gtgaaaactc tacttttgaa     60

gtttaccaaa aaaaatactc tacttttgga aagacattgc tcctaaaatc ttattagttg    120

tatataattt actaaaacac atagttcttg aattcttgtt aatgagcatg ttaccttgga    180

caagtgaccc tttttctaca ttttgttttt ctatcacacg tcatgcgttt tgattgtttc    240

cttacgagtt ttaattttat tttttggtta aaaacagtaa gataa                    285
```

<210> SEQ ID NO 19
<211> LENGTH: 137
<212> TYPE: DNA
<213> ORGANISM: Arabidopsis thaliana

<400> SEQUENCE: 19

```
tctaaaaata cagggcaccg aaccaaataa aggtgagaat gatgagaagc cgtttcttac     60

tcttcattgt tttcttctct ctatccctct tcatttcctc tctgatcgcc agtgatttag    120

gcttctgcaa cgaagag                                                   137
```

<210> SEQ ID NO 20

<211> LENGTH: 36
<212> TYPE: DNA
<213> ORGANISM: Artificial Sequence
<220> FEATURE:
<223> OTHER INFORMATION: synthetic sequence

<400> SEQUENCE: 20
aataatggta cctggtgctt aaacactctg gtgagt 36

<210> SEQ ID NO 21
<211> LENGTH: 38
<212> TYPE: DNA
<213> ORGANISM: Artificial Sequence
<220> FEATURE:
<223> OTHER INFORMATION: synthetic sequence

<400> SEQUENCE: 21
aataatccat ggtttgacct acaaaatcaa agcagtca 38

<210> SEQ ID NO 22
<211> LENGTH: 34
<212> TYPE: DNA
<213> ORGANISM: Artificial Sequence
<220> FEATURE:
<223> OTHER INFORMATION: synthetic sequence

<400> SEQUENCE: 22
ttttttggta ccagttcttt gctttcgaag ttgc 34

<210> SEQ ID NO 23
<211> LENGTH: 35
<212> TYPE: DNA
<213> ORGANISM: Artificial Sequence
<220> FEATURE:
<223> OTHER INFORMATION: synthetic sequence

<400> SEQUENCE: 23
ttttttccat ggtactacgt actgttttca attct 35

<210> SEQ ID NO 24
<211> LENGTH: 37
<212> TYPE: DNA
<213> ORGANISM: Artificial Sequence
<220> FEATURE:
<223> OTHER INFORMATION: synthetic sequence

<400> SEQUENCE: 24
aaaaaaggta ccatttccac acgctttcta tcatttc 37

<210> SEQ ID NO 25
<211> LENGTH: 42
<212> TYPE: DNA
<213> ORGANISM: Artificial Sequence
<220> FEATURE:
<223> OTHER INFORMATION: synthetic sequence

<400> SEQUENCE: 25
aaaaaaccat ggttatctct ctctaaaaaa taaaaacgaa tc 42

<210> SEQ ID NO 26
<211> LENGTH: 33
<212> TYPE: DNA
<213> ORGANISM: Artificial Sequence
<220> FEATURE:
<223> OTHER INFORMATION: synthetic sequence

<400> SEQUENCE: 26

```
aataaaggta ccgtccagaa ttttctccat tga                              33


<210> SEQ ID NO 27
<211> LENGTH: 34
<212> TYPE: DNA
<213> ORGANISM: Artificial Sequence
<220> FEATURE:
<223> OTHER INFORMATION: synthetic sequence

<400> SEQUENCE: 27

aataaaccat ggtcttcact atccaaagct ctca                             34


<210> SEQ ID NO 28
<211> LENGTH: 37
<212> TYPE: DNA
<213> ORGANISM: Artificial Sequence
<220> FEATURE:
<223> OTHER INFORMATION: synthetic sequence

<400> SEQUENCE: 28

tttttggta ccgtctactt tcattacagt gactctg                           37


<210> SEQ ID NO 29
<211> LENGTH: 39
<212> TYPE: DNA
<213> ORGANISM: Artificial Sequence
<220> FEATURE:
<223> OTHER INFORMATION: synthetic sequence

<400> SEQUENCE: 29

ttttttccat ggttatattt tacctgcaac acaattcaa                        39


<210> SEQ ID NO 30
<211> LENGTH: 32
<212> TYPE: DNA
<213> ORGANISM: Artificial Sequence
<220> FEATURE:
<223> OTHER INFORMATION: synthetic sequence

<400> SEQUENCE: 30

ttttatggta cccactcgaa tactgcatgc aa                               32


<210> SEQ ID NO 31
<211> LENGTH: 38
<212> TYPE: DNA
<213> ORGANISM: Artificial Sequence
<220> FEATURE:
<223> OTHER INFORMATION: synthetic sequence

<400> SEQUENCE: 31

ttttatccat ggttatgtag cctttacaca gaaaacaa                         38


<210> SEQ ID NO 32
<211> LENGTH: 32
<212> TYPE: DNA
<213> ORGANISM: Artificial Sequence
<220> FEATURE:
<223> OTHER INFORMATION: synthetic sequence

<400> SEQUENCE: 32

tatataggta ccaacaacta tggcctgagg gt                               32


<210> SEQ ID NO 33
<211> LENGTH: 44
<212> TYPE: DNA
```

<213> ORGANISM: Artificial Sequence
<220> FEATURE:
<223> OTHER INFORMATION: synthetic sequence

<400> SEQUENCE: 33
tatataccat ggttatctta ctgtttttaa ccaaaaaata aaat 44

<210> SEQ ID NO 34
<211> LENGTH: 36
<212> TYPE: DNA
<213> ORGANISM: Artificial Sequence
<220> FEATURE:
<223> OTHER INFORMATION: synthetic sequence

<400> SEQUENCE: 34
tttttaggta ccatcttagg gtttcgcgag atctca 36

<210> SEQ ID NO 35
<211> LENGTH: 42
<212> TYPE: DNA
<213> ORGANISM: Artificial Sequence
<220> FEATURE:
<223> OTHER INFORMATION: synthetic sequence

<400> SEQUENCE: 35 tttttccat ggtgctaagc tatctctgtt aatataaaat tg 42

<210> SEQ ID NO 36
<211> LENGTH: 34
<212> TYPE: DNA
<213> ORGANISM: Artificial Sequence
<220> FEATURE:
<223> OTHER INFORMATION: synthetic sequence

<400> SEQUENCE: 36
ttttttggta ccatttttgt tggtgaaagg taga 34

<210> SEQ ID NO 37
<211> LENGTH: 37
<212> TYPE: DNA
<213> ORGANISM: Artificial Sequence
<220> FEATURE:
<223> OTHER INFORMATION: synthetic sequence

<400> SEQUENCE: 37
tttttaccat ggttacgttt ttgtctctgc ttcttct 37

<210> SEQ ID NO 38
<211> LENGTH: 36
<212> TYPE: DNA
<213> ORGANISM: Artificial Sequence
<220> FEATURE:
<223> OTHER INFORMATION: synthetic sequence

<400> SEQUENCE: 38
tatattggta cctctgggaa atatcgattt tgatct 36

<210> SEQ ID NO 39
<211> LENGTH: 33
<212> TYPE: DNA
<213> ORGANISM: Artificial Sequence
<220> FEATURE:
<223> OTHER INFORMATION: synthetic sequence

<400> SEQUENCE: 39
tatataccat ggtctcacca catcccaaag ctc 33

<210> SEQ ID NO 40
<211> LENGTH: 35
<212> TYPE: DNA
<213> ORGANISM: Artificial Sequence
<220> FEATURE:
<223> OTHER INFORMATION: synthetic sequence

<400> SEQUENCE: 40
ttttatggta ccgcacaatc ttagcttacc ttgaa 35

<210> SEQ ID NO 41
<211> LENGTH: 37
<212> TYPE: DNA
<213> ORGANISM: Artificial Sequence
<220> FEATURE:
<223> OTHER INFORMATION: synthetic sequence

<400> SEQUENCE: 41
ttttatccat ggttatttaa tccacaagcc ttgcctc 37

<210> SEQ ID NO 42
<211> LENGTH: 29
<212> TYPE: DNA
<213> ORGANISM: Artificial Sequence
<220> FEATURE:
<223> OTHER INFORMATION: synthetic sequence

<400> SEQUENCE: 42
tttttaccat ggtgtcggag aagtgggcg 29

<210> SEQ ID NO 43
<211> LENGTH: 27
<212> TYPE: DNA
<213> ORGANISM: Artificial Sequence
<220> FEATURE:
<223> OTHER INFORMATION: synthetic sequence

<400> SEQUENCE: 43
tttttaccat ggagaagtgg gcggacg 27

<210> SEQ ID NO 44
<211> LENGTH: 37
<212> TYPE: DNA
<213> ORGANISM: Artificial Sequence
<220> FEATURE:
<223> OTHER INFORMATION: synthetic sequence

<400> SEQUENCE: 44
ttttatggta cctagcttaa tctcagattc gaatcgt 37

<210> SEQ ID NO 45
<211> LENGTH: 40
<212> TYPE: DNA
<213> ORGANISM: Artificial Sequence
<220> FEATURE:
<223> OTHER INFORMATION: synthetic sequence

<400> SEQUENCE: 45
ttttatccat ggtagtatct acataccaat catacaaatg 40

<210> SEQ ID NO 46
<211> LENGTH: 32
<212> TYPE: DNA
<213> ORGANISM: Artificial Sequence
<220> FEATURE:

```
<223> OTHER INFORMATION: synthetic sequence

<400> SEQUENCE: 46

ttttttggta cctttcacga tttggaattt ga                              32


<210> SEQ ID NO 47
<211> LENGTH: 36
<212> TYPE: DNA
<213> ORGANISM: Artificial Sequence
<220> FEATURE:
<223> OTHER INFORMATION: synthetic sequence

<400> SEQUENCE: 47

ttttttccat ggtctacaac attaaaacga ccatta                          36


<210> SEQ ID NO 48
<211> LENGTH: 32
<212> TYPE: DNA
<213> ORGANISM: Artificial Sequence
<220> FEATURE:
<223> OTHER INFORMATION: synthetic sequence

<400> SEQUENCE: 48

tatataggta ccagggtttc gtttttgttt ca                              32


<210> SEQ ID NO 49
<211> LENGTH: 35
<212> TYPE: DNA
<213> ORGANISM: Artificial Sequence
<220> FEATURE:
<223> OTHER INFORMATION: synthetic sequence

<400> SEQUENCE: 49

tatataccat ggttatctcc tgctcaaaga aacca                           35


<210> SEQ ID NO 50
<211> LENGTH: 33
<212> TYPE: DNA
<213> ORGANISM: Artificial Sequence
<220> FEATURE:
<223> OTHER INFORMATION: synthetic sequence

<400> SEQUENCE: 50

tttataggta ccagaagctc atttcttcga tac                             33


<210> SEQ ID NO 51
<211> LENGTH: 32
<212> TYPE: DNA
<213> ORGANISM: Artificial Sequence
<220> FEATURE:
<223> OTHER INFORMATION: synthetic sequence

<400> SEQUENCE: 51

tttataccat ggtctctgcg caaaaattca cc                              32


<210> SEQ ID NO 52
<211> LENGTH: 31
<212> TYPE: DNA
<213> ORGANISM: Artificial Sequence
<220> FEATURE:
<223> OTHER INFORMATION: synthetic sequence

<400> SEQUENCE: 52

tatattggta cctctaaaaa tacagggcac c                               31
```

<210> SEQ ID NO 53
<211> LENGTH: 35
<212> TYPE: DNA
<213> ORGANISM: Artificial Sequence
<220> FEATURE:
<223> OTHER INFORMATION: synthetic sequence

<400> SEQUENCE: 53
tatattccat ggttactctt cgttgcagaa gccta 35

<210> SEQ ID NO 54
<211> LENGTH: 33
<212> TYPE: DNA
<213> ORGANISM: Artificial Sequence
<220> FEATURE:
<223> OTHER INFORMATION: synthetic sequence

<400> SEQUENCE: 54
tatataggta ccactgttta agcttcactg tct 33

<210> SEQ ID NO 55
<211> LENGTH: 32
<212> TYPE: DNA
<213> ORGANISM: Artificial Sequence
<220> FEATURE:
<223> OTHER INFORMATION: synthetic sequence

<400> SEQUENCE: 55
tatataccat ggtttcttct aaagctgaaa gt 32

<210> SEQ ID NO 56
<211> LENGTH: 39
<212> TYPE: DNA
<213> ORGANISM: Artificial Sequence
<220> FEATURE:
<223> OTHER INFORMATION: synthetic sequence

<400> SEQUENCE: 56
tatataggta ccttaagctt ttaagaatct ctactcaca 39

<210> SEQ ID NO 57
<211> LENGTH: 41
<212> TYPE: DNA
<213> ORGANISM: Artificial Sequence
<220> FEATURE:
<223> OTHER INFORMATION: synthetic sequence

<400> SEQUENCE: 57
atatatccat ggttaaattt tacctgtcat caaaaacaac a 41

<210> SEQ ID NO 58
<211> LENGTH: 49
<212> TYPE: DNA
<213> ORGANISM: Artificial Sequence
<220> FEATURE:
<223> OTHER INFORMATION: synthetic sequence

<400> SEQUENCE: 58
ggggacaact ttgtatagaa aagttggcca catcatgttt agacttatc 49

<210> SEQ ID NO 59
<211> LENGTH: 50
<212> TYPE: DNA
<213> ORGANISM: Artificial Sequence
<220> FEATURE:
<223> OTHER INFORMATION: synthetic sequence

<400> SEQUENCE: 59
ggggactgct tttttgtaca aacttgttta ccttttatat ttatatatag 50

<210> SEQ ID NO 60
<211> LENGTH: 73
<212> TYPE: DNA
<213> ORGANISM: Artificial Sequence
<220> FEATURE:
<223> OTHER INFORMATION: synthetic sequence

<400> SEQUENCE: 60
ggtacccggg gatcctctag catatgctcg aggcggccgc agatatcaga tctggtcgac 60
ggcatgcaag ctt 73

<210> SEQ ID NO 61
<211> LENGTH: 12197
<212> TYPE: DNA
<213> ORGANISM: Artificial Sequence
<220> FEATURE:
<223> OTHER INFORMATION: vector sequence

<400> SEQUENCE: 61
gacatacaaa tggacgaacg gataaacctt ttcacgccct tttaaatatc cgattattct 60
aataaacgct cttttctctt aggtttaccc gccaatatat cctgtcaaac actgatagtt 120
taaactgaag gcgggaaacg acaatcagat ctagtaggaa acagctatga ccatgattac 180
gccaagctat cgattacgcc aagctatcaa ctttgtatag aaaagttggc cacatcatgt 240
ttagacttat ctccataaag aaaaccactc atcaaagcta atacaaaagc tctagtgtga 300
cacttcaacg tcacttcatc aggatcagca ggtaaattcc gaaaattctc acgcagccac 360
gctaaggaca catgagaacc atgaagatcc ttgggacctg gcctatgacc aagcaaatcc 420
tcacataaat cagcccagtt gtattttgta ctaccagtta ctgcaggtcc atcgacacgt 480
agacccaaca aaatattcac atcttgtaaa gtcacagtga tctctccagc aggaagatga 540
aaagtatgcg tttcgggtct ccatctctcc accaaagctg ttatcagagc ataatcaagt 600
tgtataaagg caaccttgta aactccatat agaccaaact ctatcaactt ttgacacacg 660
agaggatcca gaggccaatc tcgcatcccc aataacttgt gccgacatgt cagttcacga 720
ggaggaacct gaatgtgaag tataacggta aaaaggaaat aattaaaaca acggaagcaa 780
aacaagaaac aagatgaaat gagaaactag taacacacct catcttccca tatagcagct 840
gatctatgct catgttgcca caccaatata gattgatcaa ctggaccagg atccaaatca 900
aagtttaata gactttgcac ctccatctat ataatatatc acaggacaat aaacacaatg 960
atcagtgatt atacaacatc aaagaaaact tgtaattctg ggaatataac tgagaaatga 1020
gaattaaaga ttcataattt gaacacaaga aatcctaaac tggtacgaaa gaaaaattgc 1080
tcaacaaaaa aatcaagcta attactcgta tacaaagaca cgaagaacta atacaagaaa 1140
caagaaacaa caaaccacaa agagattgaa ccaatccaaa ttcgacaaca taaaccaagt 1200
gtgtgggtga ttggaatcag aggacgtacc aaagaaaagc gtccgtgatc aacaaaaacc 1260
aaaaagagac gtttgaaata aaccagagga agacgaagaa taattaagca aagagaagcg 1320
ttaagcggga gcgagaaagg aaacgagaga aagagagagc ttccagatcc gacagaagtt 1380
ttcggcttct tctttttcgt ttaagaactt ctgatcctcc taggtctgtc cgaagaacta 1440
atctttttga ggtaacgacg ccgtttttct caaaacatgg gcccattaac catagtctcg 1500
gcccaaacga aacttaatac gacaatgttt gggtgtaaac gcaaagattt tgtcgattat 1560

```
cacaagtaaa aaaataaata caaacacttg agtctctcta gacatcgtgc atcgccttag   1620
ctttaagttt tttctcgaaa caaaagagtt attttatttg aactttgaag attatacgaa   1680
gacacgtggc gtgaacccaa ttcataacaa cgccacgcta tactcttttg catgcacctc   1740
aatttgaaca tcatcaagtc tctctctctt tttctgactt tgatccacga acctaaccag   1800
cttgcgatct ctatttaatc ggtcctcgac gcaacttcaa cttctactac atccattcac   1860
atcaaatcaa tacagaaagt tttttctata tataaatata aaaggtaaac aagtttgtac   1920
aaaaaagcag gctggtacct ggtgcttaaa cactctggtg agttctagta cttctgctat   1980
gatcgatctc attaccattt cttaaatttc tctccctaaa tattccgagt tcttgatttt   2040
tgataacttc aggttttctc tttttgataa atctggtctt tccatttttt tttttttgtg   2100
gttaatttag tttcctatgt tcttcgattg tattatgcat gatctgtgtt tggattctgt   2160
tagattatgt attggtgaat atgtatgtgt ttttgcatgt ctggttttgg tcttaaaaat   2220
gttcaaatct gatgatttga ttgaagcttt tttagtgttg gtttgattct tctcaaaact   2280
actgttaatt tactatcatg ttttccaact ttgattcatg atgacacttt tgttctgctt   2340
tgttataaaa ttttggttgg tttgattttg taattatagt gtaattttgt taggaatgaa   2400
catgttttaa tactctgttt tcgatttgtc acacattcga attattaatc gataatttaa   2460
ctgaaaattc atggttctag atcttgttgt catcagatta tttgtttcga taattcatca   2520
aatatgtagt ccttttgctg atttgcgact gtttcatttt ttctcaaaat tgttttttgt   2580
taagtttatc taacagttat cgttgtcaaa agtctctttc attttgcaaa atcttctttt   2640
tttttttgtt tgtaactttg ttttttaagc tacacattta gtctgtaaaa tagcatcgag   2700
gaacagttgt cttagtagac ttgcatgttc ttgtaacttc tatttgtttc agtttgttga   2760
tgactgcttt gattttgtag gtcaaaccat ggaagacgcc aaaaacataa agaaaggccc   2820
ggcgccattc tatccgctgg aagatggaac cgctggagag caactgcata aggctatgaa   2880
gagatacgcc ctggttcctg gaacaattgc ttttacagat gcacatatcg aggtggacat   2940
cacttacgct gagtacttcg aaatgtccgt tcggttggca gaagctatga aacgatatgg   3000
gctgaataca aatcacagaa tcgtcgtatg cagtgaaaac tctcttcaat tctttatgcc   3060
ggtgttgggc gcgttattta tcggagttgc agttgcgccc gcgaacgaca tttataatga   3120
acgtgaattg ctcaacagta tgggcatttc gcagcctacc gtggtgttcg tttccaaaaa   3180
ggggttgcaa aaaattttga acgtgcaaaa aaagctccca atcatccaaa aaattattat   3240
catggattct aaaacggatt accagggatt tcagtcgatg tacacgttcg tcacatctca   3300
tctacctccc ggttttaatg aatacgattt tgtgccagag tccttcgata gggacaagac   3360
aattgcactg atcatgaact cctctggatc tactggtctg cctaaaggtg tcgctctgcc   3420
tcatagaact gcctgcgtga gattctcgca tgccagagat cctatttttg gcaatcaaat   3480
cattccggat actgcgattt taagtgttgt tccattccat cacggttttg gaatgtttac   3540
tacactcgga tatttgatat gtggatttcg agtcgtctta atgtatagat ttgaagaaga   3600
gctgtttctg aggagccttc aggattacaa gattcaaagt gcgctgctgg tgccaaccct   3660
attctccttc ttcgccaaaa gcactctgat tgacaaatac gatttatcta atttacacga   3720
aattgcttct ggtggcgctc ccctctctaa ggaagtcggg gaagcggttg ccaagaggtt   3780
ccatctgcca ggtatcaggc aaggatatgg gctcactgag actacatcag ctattctgat   3840
tacacccgag gggatgata aaccgggcgc ggtcggtaaa gttgttccat tttttgaagc   3900
```

```
gaaggttgtg gatctggata ccgggaaaac gctgggcgtt aatcaaagag gcgaactgtg   3960
tgtgagaggt cctatgatta tgtccggtta tgtaaacaat ccggaagcga ccaacgcctt   4020
gattgacaag gatggatggc tacattctgg agacatagct tactgggacg aagacgaaca   4080
cttcttcatc gttgaccgcc tgaagtctct gattaagtac aaaggctatc aggtggctcc   4140
cgctgaattg gaatccatct tgctccaaca ccccaacatc ttcgacgcag gtgtcgcagg   4200
tcttcccgac gatgacgccg gtgaacttcc cgccgccgtt gttgttttgg agcacggaaa   4260
gacgatgacg gaaaaagaga tcgtggatta cgtcgccagt caagtaacaa ccgcgaaaaa   4320
gttgcgcgga ggagttgtgt ttgtggacga agtaccgaaa ggtcttaccg gaaaactcga   4380
cgcaagaaaa atcagagaga tcctcataaa ggccaagaag ggcggaaaga tcgccgtgta   4440
actcgagcat atgggctcga atttccccga tcgttcaaac atttggcaat aaagtttctt   4500
aagattgaat cctgttgccg gtcttgcgat gattatcata taatttctgt tgaattacgt   4560
taagcatgta ataattaaca tgtaatgcat gacgttattt atgagatggg tttttatgat   4620
tagagtcccg caattataca tttaatacgc gatagaaaac aaaatatagc gcgcaaacta   4680
ggataaatta tcgcgcgcgg tgtcatctat gttactagat cgggaattca agcttggcgt   4740
aatcatggac ccagctttct tgtacaaagt ggggtacccg ggatcctctt agcatatgct   4800
cgaggcggcc gcagatatca gatctggtcg acggcatgca agcttggcgt aatcatggca   4860
actttattat acatagttga taattcactg gccggataat tcactggccg tcgttttaca   4920
acgactcagg atcctgtcaa acactgatag tttaaactga aggcgggaaa cgacaatctg   4980
atcatgagcg gagaattaag ggagtcacgt tatgaccccc gccgatgacg cgggacaagc   5040
cgttttacgt ttggaactga cagaaccgca acgttgaagg agccactcag ccgcgggttt   5100
ctggagttta atgagctaag cacatacgtc agaaaccatt attgcgcgtt caaaagtcgc   5160
ctaaggtcac tatcagctag caaatatttc ttgtcaaaaa tgctccactg acgttccata   5220
aattcccctc ggtatccaat tagagtctca tattcactct caatccaaat aatctgcacc   5280
ggatctggat cgtttcgcat gattgaacaa gatggattgc acgcaggttc tccggccgct   5340
tgggtggaga ggctattcgg ctatgactgg gcacaacaga caatcggctg ctctgatgcc   5400
gccgtgttcc ggctgtcagc gcaggggcgc ccggttcttt ttgtcaagac cgacctgtcc   5460
ggtgccctga atgaactgca ggacgaggca gcgcggctat cgtggctggc cacgacgggc   5520
gttccttgcg cagctgtgct cgacgttgtc actgaagcgg gaagggactg gctgctattg   5580
ggcgaagtgc cggggcagga tctcctgtca tctcaccttg ctcctgccga gaaagtatcc   5640
atcatggctg atgcaatgcg gcggctgcat acgcttgatc cggctacctg cccattcgac   5700
caccaagcga aacatcgcat cgagcgagca cgtactcgga tggaagccgg tcttgtcgat   5760
caggatgatc tggacgaaga gcatcagggg ctcgcgccag ccgaactgtt cgccaggctc   5820
aaggcgcgca tgcccgacgg cgaggatctc gtcgtgaccc atggcgatgc ctgcttgccg   5880
aatatcatgg tggaaaatgg ccgcttttct ggattcatcg actgtggccg gctgggtgtg   5940
gcggaccgct atcaggacat agcgttggct acccgtgata ttgctgaaga gcttggcggc   6000
gaatgggctg accgcttcct cgtgctttac ggtatcgccg ctcccgattc gcagcgcatc   6060
gccttctatc gccttcttga cgagttcttc tgagcgggac ccaagctcta gatcttgctg   6120
cgttcggata ttttcgtgga gttcccgcca cagacccgga tgatccccga tcgttcaaac   6180
atttggcaat aaagtttctt aagattgaat cctgttgccg gtcttgcgat gattatcata   6240
taatttctgt tgaattacgt taagcatgta ataattaaca tgtaatgcat gacgttattt   6300
```

-continued

```
atgagatggg tttttatgat tagagtcccg caattataca tttaatacgc gatagaaaac   6360
aaaatatagc gcgcaaacta ggataaatta tcgcgcgcgg tgtcatctat gttactagat   6420
cgggcctcct gtcaagctct gcttggtaat aattgtcatt agattgtttt tatgcataga   6480
tgcactcgaa atcagccaat tttagacaag tatcaaacgg atgttaattc agtacattaa   6540
agacgtccgc aatgtgttat taagttgtct aagcgtcaat ttgtttacac cacaatatat   6600
cctgccacca gccagccaac agctccccga ccggcagctc ggcacaaaat caccacgcgt   6660
taccaccacg ccggccggcc gcatggtgtt gaccgtgttc gccggcattg ccgagttcga   6720
gcgttcccta atcatcgacc gcacccggag cgggcgcgag gccgccaagg cccgaggcgt   6780
gaagtttggc ccccgcccta ccctcacccc ggcacagatc gcgcacgccc gcgagctgat   6840
cgaccaggaa ggccgcaccg tgaaagaggc ggctgcactg cttggcgtgc atcgctcgac   6900
cctgtaccgc gcacttgagc gcagcgagga agtgacgccc accgaggcca ggcggcgcgg   6960
tgccttccgt gaggacgcat tgaccgaggc cgacgccctg gcggccgccg agaatgaacg   7020
ccaagaggaa caagcatgaa accgcaccag gacggccagg acgaaccgtt tttcattacc   7080
gaagagatcg aggcggagat gatcgcggcc gggtacgtgt tcgagccgcc cgcgcacgtc   7140
tcaaccgtgc ggctgcatga aatcctggcc ggtttgtctg atgccaagct ggcggcctgg   7200
ccggccagct tggccgctga agaaaccgag cgccgccgtc taaaaaggtg atgtgtattt   7260
gagtaaaaca gcttgcgtca tgcggtcgct gcgtatatga tgcgatgagt aaataaacaa   7320
atacgcaagg ggaacgcatg aaggttatcg ctgtacttaa ccagaaaggc gggtcaggca   7380
agacgaccat cgcaacccat ctagcccgcg ccctgcaact cgccggggcc gatgttctgt   7440
tagtcgattc cgatccccag ggcagtgccc gcgattgggc ggccgtgcgg gaagatcaac   7500
cgctaaccgt tgtcggcatc gaccgcccga cgattgaccg cgacgtgaag gccatcggcc   7560
ggcgcgactt cgtagtgatc gacggagcgc cccaggcggc ggacttggct gtgtccgcga   7620
tcaaggcagc cgacttcgtg ctgattccgg tgcagccaag cccttacgac atatgggcca   7680
ccgccgacct ggtggagctg gttaagcagc gcattgaggt cacggatgga aggctacaag   7740
cggcctttgt cgtgtcgcgg gcgatcaaag gcacgcgcat cggcggtgag gttgccgagg   7800
cgctggccgg gtacgagctg cccattcttg agtcccgtat cacgcagcgc gtgagctacc   7860
caggcactgc cgccgccggc acaaccgttc ttgaatcaga acccgagggc gacgctgccc   7920
gcgaggtcca ggcgctggcc gctgaaatta aatcaaaact catttgagtt aatgaggtaa   7980
agagaaaatg agcaaaagca caaacacgct aagtgccggc cgtccgagcg cacgcagcag   8040
caaggctgca acgttggcca gcctggcaga cacgccagcc atgaagcggg tcaactttca   8100
gttgccggcg gaggatcaca ccaagctgaa gatgtacgcg gtacgccaag gcaagaccat   8160
taccgagctg ctatctgaat acatcgcgca gctaccagag taaatgagca aatgaataaa   8220
tgagtagatg aattttagcg gctaaaggag gcggcatgga aaatcaagaa caaccaggca   8280
ccgacgccgt ggaatgcccc atgtgtggag gaacgggcgg ttggccaggc gtaagcggct   8340
gggttgtctg ccggccctgc aatggcactg gaacccccaa gcccgaggaa tcggcgtgag   8400
cggtcgcaaa ccatccggcc cggtacaaat cggcgcggcg ctgggtgatg acctggtgga   8460
gaagttgaag gccgcgcagg ccgcccagcg gcaacgcatc gaggcagaag cacgccccgg   8520
tgaatcgtgg caagcggccg ctgatcgaat ccgcaaagaa tcccggcaac cgccggcagc   8580
cggtgcgccg tcgattagga agccgcccaa gggcgacgag caaccagatt ttttcgttcc   8640
```

```
gatgctctat gacgtgggca cccgcgatag tcgcagcatc atggacgtgg ccgttttccg   8700
tctgtcgaag cgtgaccgac gagctggcga ggtgatccgc tacgagcttc cagacgggca   8760
cgtagaggtt tccgcagggc cggccggcat ggccagtgtg tgggattacg acctggtact   8820
gatggcggtt tcccatctaa ccgaatccat gaaccgatac cgggaaggga agggagacaa   8880
gcccggccgc gtgttccgtc cacacgttgc ggacgtactc aagttctgcc ggcgagccga   8940
tggcggaaag cagaaagacg acctggtaga aacctgcatt cggttaaaca ccacgcacgt   9000
tgccatgcag cgtacgaaga aggccaagaa cggccgcctg gtgacggtat ccgagggtga   9060
agccttgatt agccgctaca agatcgtaaa gagcgaaacc gggcggccgg agtacatcga   9120
gatcgagcta gctgattgga tgtaccgcga gatcacagaa ggcaagaacc cggacgtgct   9180
gacggttcac cccgattact ttttgatcga tcccggcatc ggccgttttc tctaccgcct   9240
ggcacgccgc gccgcaggca aggcagaagc cagatggttg ttcaagacga tctacgaacg   9300
cagtggcagc gccggagagt tcaagaagtt ctgtttcacc gtgcgcaagc tgatcgggtc   9360
aaatgacctg ccggagtacg atttgaagga ggaggcgggg caggctggcc cgatcctagt   9420
catgcgctac cgcaacctga tcgagggcga agcatccgcc ggttcctaat gtacggagca   9480
gatgctaggg caaattgccc tagcagggga aaaaggtcga aaaggtctct ttcctgtgga   9540
tagcacgtac attgggaacc caaagccgta cattgggaac cggaacccgt acattgggaa   9600
cccaaagccg tacattggga accggtcaca catgtaagtg actgatataa aagagaaaaa   9660
aggcgatttt tccgcctaaa actctttaaa acttattaaa actcttaaaa cccgcctggc   9720
ctgtgcataa ctgtctggcc agcgcacagc cgaagagctg caaaaagcgc ctacccttcg   9780
gtcgctgcgc tccctacgcc ccgccgcttc gcgtcggcct atcgcggccg ctggccgctc   9840
aaaaatggct ggcctacggc caggcaatct accagggcgc ggacaagccg cgccgtcgcc   9900
actcgaccgc cggcgcccac atcaaggcac cctgcctcgc gcgtttcggt gatgacggtg   9960
aaaacctctg acacatgcag ctcccggaga cggtcacagc ttgtctgtaa gcggatgccg  10020
ggagcagaca agcccgtcag ggcgcgtcag cgggtgttgg cgggtgtcgg ggcgcagcca  10080
tgacccagtc acgtagcgat agcggagtgt atactggctt aactatgcgg catcagagca  10140
gattgtactg agagtgcacc atatgcggtg tgaaataccg cacagatgcg taaggagaaa  10200
ataccgcatc aggcgctctt ccgcttcctc gctcactgac tcgctgcgct cggtcgttcg  10260
gctgcggcga gcggtatcag ctcactcaaa ggcggtaata cggttatcca cagaatcagg  10320
ggataacgca ggaaagaaca tgtgagcaaa aggccagcaa aaggccagga accgtaaaaa  10380
ggccgcgttg ctggcgtttt tccataggct ccgcccccct gacgagcatc acaaaaatcg  10440
acgctcaagt cagaggtggc gaaacccgac aggactataa agataccagg cgtttccccc  10500
tggaagctcc ctcgtgcgct ctcctgttcc gaccctgccg cttaccggat acctgtccgc  10560
ctttctccct tcgggaagcg tggcgctttc tcatagctca cgctgtaggt atctcagttc  10620
ggtgtaggtc gttcgctcca agctgggctg tgtgcacgaa ccccccgttc agcccgaccg  10680
ctgcgcctta tccggtaact atcgtcttga gtccaacccg gtaagacacg acttatcgcc  10740
actggcagca gccactggta acaggattag cagagcgagg tatgtaggcg gtgctacaga  10800
gttcttgaag tggtggccta actacggcta cactagaagg acagtatttg gtatctgcgc  10860
tctgctgaag ccagttacct tcggaaaaag agttggtagc tcttgatccg gcaaacaaac  10920
caccgctggt agcggtggtt tttttgtttg caagcagcag attacgcgca gaaaaaaagg  10980
atctcaagaa gatcctttga tcttttctac ggggtctgac gctcagtgga acgaaaactc  11040
```

```
acgttaaggg attttggtca tgcatgatat atctcccaat ttgtgtaggg cttattatgc  11100

acgcttaaaa ataataaaag cagacttgac ctgatagttt ggctgtgagc aattatgtgc  11160

ttagtgcatc taacgcttga gttaagccgc gccgcgaagc ggcgtcggct tgaacgaatt  11220

tctagctaga cattatttgc cgactacctt ggtgatctcg cctttcacgt agtggacaaa  11280

ttcttccaac tgatctgcgc gcgaggccaa gcgatcttct tcttgtccaa gataagcctg  11340

tctagcttca agtatgacgg gctgatactg ggccggcagg cgctccattg cccagtcggc  11400

agcgacatcc ttcggcgcga ttttgccggt tactgcgctg taccaaatgc gggacaacgt  11460

aagcactaca tttcgctcat cgccagccca gtcgggcggc gagttccata gcgttaaggt  11520

ttcatttagc gcctcaaata gatcctgttc aggaaccgga tcaaagagtt cctccgccgc  11580

tggacctacc aaggcaacgc tatgttctct tgcttttgtc agcaagatag ccagatcaat  11640

gtcgatcgtg gctggctcga agatacctgc aagaatgtca ttgcgctgcc attctccaaa  11700

ttgcagttcg cgcttagctg gataacgcca cggaatgatg tcgtcgtgca caacaatggt  11760

gacttctaca gcgcggagaa tctcgctctc tccaggggaa gccgaagttt ccaaaaggtc  11820

gttgatcaaa gctcgccgcg ttgtttcatc aagccttacg gtcaccgtaa ccagcaaatc  11880

aatatcactg tgtggcttca ggccgccatc cactgcggag ccgtacaaat gtacggccag  11940

caacgtcggt tcgagatggc gctcgatgac gccaactacc tctgatagtt gagtcgatac  12000

ttcggcgatc accgcttccc ccatgatgtt taactttgtt ttagggcgac tgccctgctg  12060

cgtaacatcg ttgctgctcc ataacatcaa acatcgaccc acggcgtaac gcgcttgctg  12120

cttggatgcc cgaggcatag actgtacccc aaaaaaacag tcataacaag ccatgaaaac  12180

cgccactgcg ttccatg                                                 12197
```

<210> SEQ ID NO 62
<211> LENGTH: 14901
<212> TYPE: DNA
<213> ORGANISM: Artificial Sequence
<220> FEATURE:
<223> OTHER INFORMATION: vector sequence

<400> SEQUENCE: 62

```
gacatacaaa tggacgaacg gataaacctt ttcacgccct tttaaatatc cgattattct     60

aataaacgct cttttctctt aggtttaccc gccaatatat cctgtcaaac actgatagtt    120

taaactgaag gcgggaaacg acaatcagat ctagtaggaa acagctatga ccatgattac    180

gccaagctat cgattacgcc aagctatcaa ctttgtatag aaaagttggc cacatcatgt    240

ttagacttat ctccataaag aaaaccactc atcaaagcta atacaaaagc tctagtgtga    300

cacttcaacg tcacttcatc aggatcagca ggtaaattcc gaaaattctc acgcagccac    360

gctaaggaca catgagaacc atgaagatcc ttgggacctg gcctatgacc aagcaaatcc    420

tcacataaat cagcccagtt gtattttgta ctaccagtta ctgcaggtcc atcgacacgt    480

agacccaaca aaatattcac atcttgtaaa gtcacagtga tctctccagc aggaagatga    540

aaagtatgcg tttcgggtct ccatctctcc accaaagctg ttatcagagc ataatcaagt    600

tgtataaagg caaccttgta aactccatat agaccaaact ctatcaactt ttgacacacg    660

agaggatcca gaggccaatc tcgcatcccc aataacttgt gccgacatgt cagttcacga    720

ggaggaacct gaatgtgaag tataacggta aaaaggaaat aattaaaaca acggaagcaa    780

aacaagaaac aagatgaaat gagaaactag taacacacct catcttccca tatagcagct    840
```

-continued

```
gatctatgct catgttgcca caccaatata gattgatcaa ctggaccagg atccaaatca    900
aagtttaata gactttgcac ctccatctat ataatatatc acaggacaat aaacacaatg    960
atcagtgatt atacaacatc aaagaaaact tgtaattctg ggaatataac tgagaaatga   1020
gaattaaaga ttcataattt gaacacaaga aatcctaaac tggtacgaaa gaaaaattgc   1080
tcaacaaaaa aatcaagcta attactcgta tacaaagaca cgaagaacta atacaagaaa   1140
caagaaacaa caaaccacaa agagattgaa ccaatccaaa ttcgacaaca taaaccaagt   1200
gtgtgggtga ttggaatcag aggacgtacc aaagaaaagc gtccgtgatc aacaaaaacc   1260
aaaaagagac gtttgaaata aaccagagga agacgaagaa taattaagca aagagaagcg   1320
ttaagcggga gcgagaaagg aaacgagaga aagagagagc ttccagatcc gacagaagtt   1380
ttcggcttct tctttttcgt ttaagaactt ctgatcctcc taggtctgtc cgaagaacta   1440
atctttttga ggtaacgacg ccgtttttct caaaacatgg gcccattaac catagtctcg   1500
gcccaaacga aacttaatac gacaatgttt gggtgtaaac gcaaagattt tgtcgattat   1560
cacaagtaaa aaaataaata caaacacttg agtctctcta gacatcgtgc atcgccttag   1620
ctttaagttt tttctcgaaa caaaagagtt attttatttg aactttgaag attatacgaa   1680
gacacgtggc gtgaacccaa ttcataacaa cgccacgcta tactcttttg catgcacctc   1740
aatttgaaca tcatcaagtc tctctctctt tttctgactt tgatccacga acctaaccag   1800
cttgcgatct ctatttaatc ggtcctcgac gcaacttcaa cttctactac atccattcac   1860
atcaaatcaa tacagaaagt tttttctata tataaatata aaaggtaaac aagtttgtac   1920
aaaaaagcag gctggtacct ggtgcttaaa cactctggtg agttctagta cttctgctat   1980
gatcgatctc attaccattt cttaaatttc tctccctaaa tattccgagt tcttgatttt   2040
tgataacttc aggttttctc tttttgataa atctggtctt tccatttttt tttttttgtg   2100
gttaatttag tttcctatgt tcttcgattg tattatgcat gatctgtgtt tggattctgt   2160
tagattatgt attggtgaat atgtatgtgt ttttgcatgt ctggttttgg tcttaaaaat   2220
gttcaaatct gatgatttga ttgaagcttt tttagtgttg gtttgattct tctcaaaact   2280
actgttaatt tactatcatg ttttccaact ttgattcatg atgacacttt tgttctgctt   2340
tgttataaaa ttttggttgg tttgattttg taattatagt gtaattttgt taggaatgaa   2400
catgttttaa tactctgttt tcgatttgtc acacattcga attattaatc gataatttaa   2460
ctgaaaattc atggttctag atcttgttgt catcagatta tttgtttcga taattcatca   2520
aatatgtagt cctttttgctg atttgcgact gtttcatttt ttctcaaaat tgtttttttgt  2580
taagtttatc taacagttat cgttgtcaaa agtctctttc attttgcaaa atcttctttt   2640
tttttttgtt tgtaactttg ttttttaagc tacacattta gtctgtaaaa tagcatcgag   2700
gaacagttgt cttagtagac ttgcatgttc ttgtaacttc tatttgtttc agtttgttga   2760
tgactgcttt gattttgtag gtcaaaccat ggaagacgcc aaaaacataa agaaaggccc   2820
ggcgccattc tatccgctgg aagatggaac cgctggagag caactgcata aggctatgaa   2880
gagatacgcc ctggttcctg gaacaattgc ttttacagat gcacatatcg aggtggacat   2940
cacttacgct gagtacttcg aaatgtccgt tcggttggca gaagctatga aacgatatgg   3000
gctgaataca aatcacagaa tcgtcgtatg cagtgaaaac tctcttcaat tctttatgcc   3060
ggtgttgggc gcgttattta tcggagttgc agttgcgccc gcgaacgaca tttataatga   3120
acgtgaattg ctcaacagta tgggcatttc gcagcctacc gtggtgttcg tttccaaaaa   3180
ggggttgcaa aaaattttga acgtgcaaaa aaagctccca atcatccaaa aaattattat   3240
```

```
catggattct aaaacggatt accagggatt tcagtcgatg tacacgttcg tcacatctca   3300
tctacctccc ggttttaatg aatacgattt tgtgccagag tccttcgata gggacaagac   3360
aattgcactg atcatgaact cctctggatc tactggtctg cctaaaggtg tcgctctgcc   3420
tcatagaact gcctgcgtga gattctcgca tgccagagat cctatttttg gcaatcaaat   3480
cattccggat actgcgattt taagtgttgt tccattccat cacggttttg gaatgtttac   3540
tacactcgga tatttgatat gtggatttcg agtcgtctta atgtatagat ttgaagaaga   3600
gctgtttctg aggagccttc aggattacaa gattcaaagt gcgctgctgg tgccaaccct   3660
attctccttc ttcgccaaaa gcactctgat tgacaaatac gatttatcta atttacacga   3720
aattgcttct ggtggcgctc ccctctctaa ggaagtcggg gaagcggttg ccaagaggtt   3780
ccatctgcca ggtatcaggc aaggatatgg gctcactgag actacatcag ctattctgat   3840
tacacccgag gggatgata aaccgggcgc ggtcggtaaa gttgttccat tttttgaagc   3900
gaaggttgtg gatctggata ccgggaaaac gctgggcgtt aatcaaagag gcgaactgtg   3960
tgtgagaggt cctatgatta tgtccggtta tgtaaacaat ccggaagcga ccaacgcctt   4020
gattgacaag gatggatggc tacattctgg agacatagct tactgggacg aagacgaaca   4080
cttcttcatc gttgaccgcc tgaagtctct gattaagtac aaaggctatc aggtggctcc   4140
cgctgaattg gaatccatct tgctccaaca ccccaacatc ttcgacgcag gtgtcgcagg   4200
tcttcccgac gatgacgccg gtgaacttcc cgccgccgtt gttgttttgg agcacggaaa   4260
gacgatgacg gaaaaagaga tcgtggatta cgtcgccagt caagtaacaa ccgcgaaaaa   4320
gttgcgcgga ggagttgtgt ttgtggacga agtaccgaaa ggtcttaccg gaaaactcga   4380
cgcaagaaaa atcagagaga tcctcataaa ggccaagaag ggcggaaaga tcgccgtgta   4440
actcgagcat atgggctcga atttccccga tcgttcaaac atttggcaat aaagtttctt   4500
aagattgaat cctgttgccg gtcttgcgat gattatcata taatttctgt tgaattacgt   4560
taagcatgta ataattaaca tgtaatgcat gacgttattt atgagatggg tttttatgat   4620
tagagtcccg caattataca tttaatacgc gatagaaaac aaaatatagc gcgcaaacta   4680
ggataaatta tcgcgcgcgg tgtcatctat gttactagat cgggaattca agcttggcgt   4740
aatcatggac ccagctttct tgtacaaagt ggggtaccaa ttcgaatcca aaaattacgg   4800
atatgaatat aggcatatcc gtatccgaat tatccgtttg acagctagca acgattgtac   4860
aattgcttct ttaaaaaagg aagaaagaaa gaaagaaaag aatcaacatc agcgttaaca   4920
aacggccccg ttacggccca aacggtcata tagagtaacg gcgttaagcg ttgaaagact   4980
cctatcgaaa tacgtaaccg caaacgtgtc atagtcagat cccctcttcc ttcaccgcct   5040
caaacacaaa aataatcttc tacagcctat atatacaacc ccccttcta tctctccttt   5100
ctcacaattc atcatctttc tttctctacc cccaatttta agaaatcctc tcttctcctc   5160
ttcattttca aggtaaatct ctctctctct ctctctctct gttattcctt gttttaatta   5220
ggtatgtatt attgctagtt tgttaatctg cttatcttat gtatgcctta tgtgaatatc   5280
tttatcttgt tcatctcatc cgtttagaag ctataaattt gttgatttga ctgtgtatct   5340
acacgtggtt atgtttatat ctaatcagat atgaatttct tcatattgtt gcgtttgtgt   5400
gtaccaatcc gaaatcgttg attttttca tttaatcgtg tagctaattg tacgtataca   5460
tatggatcta cgtatcaatt gttcatctgt ttgtgtttgt atgtatacag atctgaaaac   5520
atcacttctc tcatctgatt gtgttgttac atacatagat atagatctgt tatatcattt   5580
```

```
tttttattaa ttgtgtatat atatatgtgc atagatctgg attacatgat tgtgattatt   5640
tacatgattt tgttatttac gtatgtatat atgtagatct ggactttttg gagttgttga   5700
cttgattgta tttgtgtgtg tatatgtgtg ttctgatctt gatatgttat gtatgtgcag   5760
ctgaaccatg gcggcggcaa caacaacaac aacaacatct tcttcgatct ccttctccac   5820
caaaccatct ccttcctcct ccaaatcacc attaccaatc tccagattct ccctcccatt   5880
ctccctaaac cccaacaaat catcctcctc ctcccgccgc cgcggtatca aatccagctc   5940
tccctcctcc atctccgccg tgctcaacac aaccaccaat gtcacaacca ctccctctcc   6000
aaccaaacct accaaacccg aaacattcat ctcccgattc gctccagatc aaccccgcaa   6060
aggcgctgat atcctcgtcg aagctttaga acgtcaaggc gtagaaaccg tattcgctta   6120
ccctggaggt acatcaatgg agattcacca agccttaacc cgctcttcct caatccgtaa   6180
cgtccttcct cgtcacgaac aaggaggtgt attcgcagca gaaggatacg ctcgatcctc   6240
aggtaaacca ggtatctgta tagccacttc aggtcccgga gctacaaatc tcgttagcgg   6300
attagccgat gcgttgttag atagtgttcc tcttgtagca atcacaggac aagtccctcg   6360
tcgtatgatt ggtacagatg cgtttcaaga gactccgatt gttgaggtaa cgcgttcgat   6420
tacgaagcat aactatcttg tgatggatgt tgaagatatc cctaggatta ttgaggaagc   6480
tttcttttta gctacttctg gtagacctgg acctgttttg gttgatgttc ctaaagatat   6540
tcaacaacag cttgcgattc ctaattggga acaggctatg agattacctg gttatatgtc   6600
taggatgcct aaacctccgg aagattctca tttggagcag attgttaggt tgatttctga   6660
gtctaagaag cctgtgttgt atgttggtgg tggttgtttg aattctagcg atgaattggg   6720
taggtttgtt gagcttacgg ggatccctgt tgcgagtacg ttgatggggc tgggatctta   6780
tccttgtgat gatgagttgt cgttacatat gcttggaatg catgggactg tgtatgcaaa   6840
ttacgctgtg gagcatagtg atttgttgtt ggcgtttggg gtaaggtttg atgatcgtgt   6900
cacgggtaag cttgaggctt ttgctagtag ggctaagatt gttcatattg atattgactc   6960
ggctgagatt gggaagaata agactcctca tgtgtctgtg tgtggtgatg ttaagctggc   7020
tttgcaaggg atgaataagg ttcttgagaa ccgagcggag gagcttaagc ttgattttgg   7080
agtttggagg aatgagttga acgtacagaa acagaagttt ccgttgagct ttaagacgtt   7140
tggggaagct attcctccac agtatgcgat taaggtcctt gatgagttga ctgatggaaa   7200
agccataata agtactggtg tcgggcaaca tcaaatgtgg gcggcgcagt tctacaatta   7260
caagaaacca aggcagtggc tatcatcagg aggccttgga gctatgggat ttggacttcc   7320
tgctgcgatt ggagcgtctg ttgctaaccc tgatgcgata gttgtggata ttgacggaga   7380
tggaagcttt ataatgaatg tgcaagagct agccactatt cgtgtagaga atcttccagt   7440
gaaggtactt ttattaaaca accagcatct tggcatggtt atgcaatggg aagatcggtt   7500
ctacaaagct aaccgagctc acacatttct cggggatccg gctcaggagg acgagatatt   7560
cccgaacatg ttgctgtttg cagcagcttg cgggattcca gcggcgaggg tgacaaagaa   7620
agcagatctc cgagaagcta ttcagacaat gctggataca ccaggacctt acctgttgga   7680
tgtgatttgt ccgcaccaag aacatgtgtt gccgatgatc ccgaatggtg gcactttcaa   7740
cgatgtcata acggaaggag atggccggat taaatactga gagatgaaac cggtgattat   7800
cagaaccttt tatggtcttt gtatgcatat ggtaaaaaaa cttagtttgc aatttcctgt   7860
ttgttttggt aatttgagtt tcttttagtt gttgatctgc ctgctttttg gtttacgtca   7920
gactactact gctgttgttg tttggtttcc tttctttcat tttataaata aataatccgg   7980
```

```
ttcggtttac tccttgtgac tggctcagtt tggttattgc gaaatgcgaa tggtaaattg   8040
agtaattgaa attcgttatt agggttctaa gctgttttaa cagtcactgg gttaatatct   8100
ctcgaatctt gcatggaaaa tgctcttacc attggttttt aattgaaatg tgctcatatg   8160
ggccgtggtt tccaaattaa ataaaactac gatgtcatcg agaagtaaaa tcaactgtgt   8220
ccacattatc agttttgtgt atacgatgaa atagggtaat tcaaaatcta gcttgatatg   8280
ccttttggtt cattttaacc ttctgtaaac attttttcag attttgaaca agtaaatcca   8340
aaaaaaaaaa aaaaaaatct caactcaaca ctaaattatt ttaatgtata aaagatgctt   8400
aaaacatttg gcttaaaaga aagaagctaa aaacatagag aactcttgta aattgaagta   8460
tgaaaatata ctgaattggg tattatatga atttttctga tttaggattc acatgatcca   8520
aaaaggaaat ccagaagcac taatcagaca ttggaagtag gaatatttca aaaagttttt   8580
tttttttaag taagtgacaa aagcttttaa aaaatagaaa agaaactagt attaaagttg   8640
taaatttaat aaacaaaaga aatttttat atttttcat ttctttttcc agcatgaggt   8700
tatgatggca ggatgtggat ttcatttttt tccttttgat agccttttaa ttgatctatt   8760
ataattgacg aaaaaatatt agttaattat agatatattt taggtagtat tagcaattta   8820
cacttccaaa agactatgta agttgtaaat atgatgcgtt gatctcttca tcattcaatg   8880
gttagtcaaa aaaataaaag cttaactagt aaactaaagt agtcaaaaat tgtactttag   8940
tttaaaatat tacatgaata atccaaaacg acatttatgt gaaacaaaaa caatatctag   9000
agtcgactta attaaactag tggcgcgcca attgactagt aggcctatcg attaattaag   9060
gccgcctcga gcatatgggc atgcaagctt ggcgtaatca tggcaacttt attatacata   9120
gttgataatt cactggccgg atctgcttgg taataattgt cattagattg tttttatgca   9180
tagatgcact cgaaatcagc caattttaga caagtatcaa acggatgtta attcagtaca   9240
ttaaagacgt ccgcaatgtg ttattaagtt gtctaagcgt caatttgttt acaccacaat   9300
atatcctgcc accagccagc caacagctcc ccgaccggca gctcggcaca aaatcaccac   9360
gcgttaccac cacgccggcc ggccgcatgg tgttgaccgt gttcgccggc attgccgagt   9420
tcgagcgttc cctaatcatc gaccgcaccc ggagcgggcg cgaggccgcc aaggcccgag   9480
gcgtgaagtt tggcccccgc cctaccctca ccccggcaca gatcgcgcac gcccgcgagc   9540
tgatcgacca ggaaggccgc accgtgaaag aggcggctgc actgcttggc gtgcatcgct   9600
cgaccctgta ccgcgcactt gagcgcagcg aggaagtgac gcccaccgag gccaggcggc   9660
gcggtgcctt ccgtgaggac gcattgaccg aggccgacgc cctggcggcc gccgagaatg   9720
aacgccaaga ggaacaagca tgaaaccgca ccaggacggc caggacgaac cgtttttcat   9780
taccgaagag atcgaggcgg agatgatcgc ggccgggtac gtgttcgagc cgcccgcgca   9840
cgtctcaacc gtgcggctgc atgaaatcct ggccggtttg tctgatgcca agctggcggc   9900
ctggccggcc agcttggccg ctgaagaaac cgagcgccgc cgtctaaaaa ggtgatgtgt   9960
atttgagtaa aacagcttgc gtcatgcggt cgctgcgtat atgatgcgat gagtaaataa   10020
acaaatacgc aaggggaacg catgaaggtt atcgctgtac ttaaccagaa aggcgggtca   10080
ggcaagacga ccatcgcaac ccatctagcc cgcgccctgc aactcgccgg ggccgatgtt   10140
ctgttagtcg attccgatcc ccagggcagt gcccgcgatt gggcggccgt gcgggaagat   10200
caaccgctaa ccgttgtcgg catcgaccgc ccgacgattg accgcgacgt gaaggccatc   10260
ggccggcgcg acttcgtagt gatcgacgga gcgccccagg cggcggactt ggctgtgtcc   10320
```

```
gcgatcaagg cagccgactt cgtgctgatt ccggtgcagc caagccctta cgacatatgg  10380
gccaccgccg acctggtgga gctggttaag cagcgcattg aggtcacgga tggaaggcta  10440
caagcggcct ttgtcgtgtc gcgggcgatc aaaggcacgc gcatcggcgg tgaggttgcc  10500
gaggcgctgg ccgggtacga gctgcccatt cttgagtccc gtatcacgca gcgcgtgagc  10560
tacccaggca ctgccgccgc cggcacaacc gttcttgaat cagaacccga gggcgacgct  10620
gcccgcgagg tccaggcgct ggccgctgaa attaaatcaa aactcatttg agttaatgag  10680
gtaaagagaa aatgagcaaa agcacaaaca cgctaagtgc cggccgtccg agcgcacgca  10740
gcagcaaggc tgcaacgttg gccagcctgg cagacacgcc agccatgaag cgggtcaact  10800
ttcagttgcc ggcggaggat cacaccaagc tgaagatgta cgcggtacgc caaggcaaga  10860
ccattaccga gctgctatct gaatacatcg cgcagctacc agagtaaatg agcaaatgaa  10920
taaatgagta gatgaatttt agcggctaaa ggaggcggca tggaaaatca agaacaacca  10980
ggcaccgacg ccgtggaatg ccccatgtgt ggaggaacgg gcggttggcc aggcgtaagc  11040
ggctgggttg tctgccggcc ctgcaatggc actggaaccc ccaagcccga ggaatcggcg  11100
tgagcggtcg caaaccatcc ggcccggtac aaatcggcgc ggcgctgggt gatgacctgg  11160
tggagaagtt gaaggccgcg caggccgccc agcggcaacg catcgaggca gaagcacgcc  11220
ccggtgaatc gtggcaagcg gccgctgatc gaatccgcaa agaatcccgg caaccgccgg  11280
cagccggtgc gccgtcgatt aggaagccgc ccaagggcga cgagcaacca gatttttcg   11340
ttccgatgct ctatgacgtg ggcacccgcg atagtcgcag catcatggac gtggccgttt  11400
tccgtctgtc gaagcgtgac cgacgagctg gcgaggtgat ccgctacgag cttccagacg  11460
ggcacgtaga ggtttccgca gggccggccg gcatggccag tgtgtgggat tacgacctgg  11520
tactgatggc ggtttcccat ctaaccgaat ccatgaaccg ataccgggaa gggaagggag  11580
acaagcccgg ccgcgtgttc cgtccacacg ttgcggacgt actcaagttc tgccggcgag  11640
ccgatggcgg aaagcagaaa gacgacctgg tagaaacctg cattcggtta aacaccacgc  11700
acgttgccat gcagcgtacg aagaaggcca agaacggccg cctggtgacg gtatccgagg  11760
gtgaagcctt gattagccgc tacaagatcg taaagagcga aaccgggcgg ccggagtaca  11820
tcgagatcga gctagctgat tggatgtacc gcgagatcac agaaggcaag aacccggacg  11880
tgctgacggt tcaccccgat tactttttga tcgatcccgg catcggccgt tttctctacc  11940
gcctggcacg ccgcgccgca ggcaaggcag aagccagatg gttgttcaag acgatctacg  12000
aacgcagtgg cagcgccgga gagttcaaga agttctgttt caccgtgcgc aagctgatcg  12060
ggtcaaatga cctgccggag tacgatttga aggaggaggc ggggcaggct ggcccgatcc  12120
tagtcatgcg ctaccgcaac ctgatcgagg gcgaagcatc cgccggttcc taatgtacgg  12180
agcagatgct agggcaaatt gccctagcag gggaaaaagg tcgaaaaggt ctctttcctg  12240
tggatagcac gtacattggg aacccaaagc cgtacattgg gaaccggaac ccgtacattg  12300
ggaacccaaa gccgtacatt gggaaccggt cacacatgta agtgactgat ataaaagaga  12360
aaaaaggcga tttttccgcc taaaactctt taaaacttat taaaactctt aaaacccgcc  12420
tggcctgtgc ataactgtct ggccagcgca cagccgaaga gctgcaaaaa gcgcctaccc  12480
ttcggtcgct gcgctcccta cgccccgccg cttcgcgtcg gcctatcgcg gccgctggcc  12540
gctcaaaaat ggctggccta cggccaggca atctaccagg gcgcggacaa gccgcgccgt  12600
cgccactcga ccgccggcgc ccacatcaag gcaccctgcc tcgcgcgttt cggtgatgac  12660
ggtgaaaacc tctgacacat gcagctcccg gagacggtca cagcttgtct gtaagcggat  12720
```

```
gccgggagca gacaagcccg tcagggcgcg tcagcgggtg ttggcgggtg tcggggcgca  12780
gccatgaccc agtcacgtag cgatagcgga gtgtatactg gcttaactat gcggcatcag  12840
agcagattgt actgagagtg caccatatgc ggtgtgaaat accgcacaga tgcgtaagga  12900
gaaaataccg catcaggcgc tcttccgctt cctcgctcac tgactcgctg cgctcggtcg  12960
ttcggctgcg gcgagcggta tcagctcact caaaggcggt aatacggtta tccacagaat  13020
caggggataa cgcaggaaag aacatgtgag caaaaggcca gcaaaaggcc aggaaccgta  13080
aaaaggccgc gttgctggcg tttttccata ggctccgccc ccctgacgag catcacaaaa  13140
atcgacgctc aagtcagagg tggcgaaacc cgacaggact ataaagatac caggcgtttc  13200
cccctggaag ctccctcgtg cgctctcctg ttccgaccct gccgcttacc ggatacctgt  13260
ccgcctttct cccttcggga agcgtggcgc tttctcatag ctcacgctgt aggtatctca  13320
gttcggtgta ggtcgttcgc tccaagctgg gctgtgtgca cgaacccccc gttcagcccg  13380
accgctgcgc cttatccggt aactatcgtc ttgagtccaa cccggtaaga cacgacttat  13440
cgccactggc agcagccact ggtaacagga ttagcagagc gaggtatgta ggcggtgcta  13500
cagagttctt gaagtggtgg cctaactacg gctacactag aaggacagta tttggtatct  13560
gcgctctgct gaagccagtt accttcggaa aaagagttgg tagctcttga tccggcaaac  13620
aaaccaccgc tggtagcggt ggtttttttg tttgcaagca gcagattacg cgcagaaaaa  13680
aaggatctca agaagatcct ttgatctttt ctacggggtc tgacgctcag tggaacgaaa  13740
actcacgtta agggattttg gtcatgcatg atatatctcc caatttgtgt agggcttatt  13800
atgcacgctt aaaaataata aaagcagact tgacctgata gtttggctgt gagcaattat  13860
gtgcttagtg catctaacgc ttgagttaag ccgcgccgcg aagcggcgtc ggcttgaacg  13920
aatttctagc tagacattat ttgccgacta ccttggtgat ctcgcctttc acgtagtgga  13980
caaattcttc caactgatct gcgcgcgagg ccaagcgatc ttcttcttgt ccaagataag  14040
cctgtctagc ttcaagtatg acgggctgat actgggccgg caggcgctcc attgcccagt  14100
cggcagcgac atccttcggc gcgattttgc cggttactgc gctgtaccaa atgcgggaca  14160
acgtaagcac tacatttcgc tcatcgccag cccagtcggg cggcgagttc catagcgtta  14220
aggtttcatt tagcgcctca aatagatcct gttcaggaac cggatcaaag agttcctccg  14280
ccgctggacc taccaaggca acgctatgtt ctcttgcttt tgtcagcaag atagccagat  14340
caatgtcgat cgtggctggc tcgaagatac ctgcaagaat gtcattgcgc tgccattctc  14400
caaattgcag ttcgcgctta gctggataac gccacggaat gatgtcgtcg tgcacaacaa  14460
tggtgacttc tacagcgcgg agaatctcgc tctctccagg ggaagccgaa gtttccaaaa  14520
ggtcgttgat caaagctcgc cgcgttgttt catcaagcct tacggtcacc gtaaccagca  14580
aatcaatatc actgtgtggc ttcaggccgc catccactgc ggagccgtac aaatgtacgg  14640
ccagcaacgt cggttcgaga tggcgctcga tgacgccaac tacctctgat agttgagtcg  14700
atacttcggc gatcaccgct tcccccatga tgtttaactt tgttttaggg cgactgccct  14760
gctgcgtaac atcgttgctg ctccataaca tcaaacatcg acccacggcg taacgcgctt  14820
gctgcttgga tgcccgaggc atagactgta ccccaaaaaa acagtcataa caagccatga  14880
aaaccgccac tgcgttccat g                                           14901
```

<210> SEQ ID NO 63
<211> LENGTH: 51
<212> TYPE: DNA

<213> ORGANISM: Artificial Sequence
<220> FEATURE:
<223> OTHER INFORMATION: synthetic sequence

<400> SEQUENCE: 63
ggggacaact ttgtatagaa aagttcacgg gcaggacata gggactacta c 51

<210> SEQ ID NO 64
<211> LENGTH: 51
<212> TYPE: DNA
<213> ORGANISM: Artificial Sequence
<220> FEATURE:
<223> OTHER INFORMATION: synthetic sequence

<400> SEQUENCE: 64
ggggactgct tttttgtaca aacttggatt tatgataaaa atgtcggttt c 51

<210> SEQ ID NO 65
<211> LENGTH: 50
<212> TYPE: DNA
<213> ORGANISM: Artificial Sequence
<220> FEATURE:
<223> OTHER INFORMATION: synthetic sequence

<400> SEQUENCE: 65
ggggacaact ttgtatagaa aagttctgca gcaaatttac acattgccac 50

<210> SEQ ID NO 66
<211> LENGTH: 50
<212> TYPE: DNA
<213> ORGANISM: Artificial Sequence
<220> FEATURE:
<223> OTHER INFORMATION: synthetic sequence

<400> SEQUENCE: 66
ggggactgct tttttgtaca aacttgactg gctatgaaga aattataatc 50

<210> SEQ ID NO 67
<211> LENGTH: 15029
<212> TYPE: DNA
<213> ORGANISM: Artificial Sequence
<220> FEATURE:
<223> OTHER INFORMATION: vector sequence

<400> SEQUENCE: 67
gacatacaaa tggacgaacg gataaacctt ttcacgccct tttaaatatc cgattattct 60
aataaacgct cttttctctt aggtttaccc gccaatatat cctgtcaaac actgatagtt 120
taaactgaag gcgggaaacg acaatcagat ctagtaggaa acagctatga ccatgattac 180
gccaagctat cgattacgcc aagctatcaa ctttgtatag aaaagttgcc atgattacgc 240
caagcttgca tgcccatatg ctcgaggcgg ccgcagatat cagatctggt cgaccacggg 300
caggacatag ggactactac aagcatagta tgcttcagac aaagagctag gaaagaactc 360
ttgatggagg ttaagagaaa aaagtgctag aggggcatag taatcaaact tgtcaaaacc 420
gtcatcatga tgagggatga cataatataa aaagttgact aaggtcttgg tagtactctt 480
tgattagtat tatatattgg tgagaacatg agtcaagagg agacaagaaa ccgaggaacc 540
atagtttagc aacaagatgg aagttgcaaa gttgagctag ccgctcgatt agttacatct 600
cctaagcagt actacaagga atggtctcta tactttcatg tttagcacat ggtagtgcgg 660
attgacaagt tagaaacagt gcttaggaga caaagagtca gtaaaggtat tgaaagagtg 720
aagttgatgc tcgacaggtc aggagaagtc cctccgccag atggtgacta ccaaggggtt 780

```
ggtatcagct gagacccaaa taagattctt cggttgaacc agtggttcga ccgagactct    840
tagggtggga tttcactgta agatttgtgc attttgttga atataaattg acaatttttt    900
ttatttaatt atagattatt tagaatgaat tacatattta gtttctaaca aggatagcaa    960
tggatgggta tgggtacagg ttaaacatat ctattaccca cccatctagt cgtcgggttt   1020
tacacgtacc cacccgttta cataaaccag accggaattt taaaccgtac ccgtccgtta   1080
gcgggtttca gatttacccg tttaatcggg taaaacctga ttactaaata tatatttttt   1140
atttgataaa caaaacaaaa atgttaatat tttcatattg gatgcaattt taagaaacac   1200
atattcataa atttccatat ttgtaggaaa ataaaaagaa aaatatattc aagaacacaa   1260
atttcaccga catgactttt attacagagt tggaattaga tctaacaatt gaaaaattaa   1320
aattaagata gaatatgttg aggaacatga catagtataa tgctgggtta cccgtcgggt   1380
aggtatcgag gcggatacta ctaaatccat cccactcgct atccgataat cactggtttc   1440
gggtataccc attcccgtca acaggccttt ttaaccggat aatttcaact tatagtgaat   1500
gaattttgaa taaatagtta gaataccaaa atcctggatt gcatttgcaa tcaaattttg   1560
tgaaccgtta aattttgcat gtacttggga tagatataat agaaccgaat tttcattagt   1620
ttaatttata acttactttg ttcaaagaaa aaaaatatct atccaattta cttataataa   1680
aaaataatct atccaagtta cttattataa tcaacttgta aaaaggtaag aatacaaatg   1740
tggtagcgta cgtgtgatta tatgtgacga aatgttatat ctaacaaaag tccaaattcc   1800
catggtaaaa aaaatcaaaa tgcatggcag gctgtttgta accttggaat aagatgttgg   1860
ccaattctgg agccgccacg tacgcaagac tcagggccac gttctcttca tgcaaggata   1920
gtagaacacc actccaccca cctcctatat tagacctttg cccaaccctc cccaactttc   1980
ccatcccatc cacaaagaaa ccgacatttt tatcataaat cactagtccc gggtacccaa   2040
gtttgtacaa aaaagcaggc tggtacctgg tgcttaaaca ctctggtgag ttctagtact   2100
tctgctatga tcgatctcat taccatttct taaatttctc tccctaaata ttccgagttc   2160
ttgatttttg ataacttcag gttttctctt tttgataaat ctggtctttc cattttttt    2220
tttttgtggt taatttagtt tcctatgttc ttcgattgta ttatgcatga tctgtgtttg   2280
gattctgtta gattatgtat tggtgaatat gtatgtgttt ttgcatgtct ggttttggtc   2340
ttaaaaatgt tcaaatctga tgatttgatt gaagcttttt tagtgttggt ttgattcttc   2400
tcaaaactac tgttaattta ctatcatgtt ttccaacttt gattcatgat gacacttttg   2460
ttctgctttg ttataaaatt ttggttggtt tgattttgta attatagtgt aattttgtta   2520
ggaatgaaca tgttttaata ctctgttttc gatttgtcac acattcgaat tattaatcga   2580
taatttaact gaaaattcat ggttctagat cttgttgtca tcagattatt tgtttcgata   2640
attcatcaaa tatgtagtcc ttttgctgat ttgcgactgt ttcatttttt ctcaaaattg   2700
ttttttgtta agtttatcta acagttatcg ttgtcaaaag tctctttcat tttgcaaaat   2760
cttctttttt tttttgtttg taactttgtt ttttaagcta cacatttagt ctgtaaaata   2820
gcatcgagga acagttgtct tagtagactt gcatgttctt gtaacttcta tttgtttcag   2880
tttgttgatg actgctttga ttttgtaggt caaaccatgg aagacgccaa aaacataaag   2940
aaaggcccgg cgccattcta tccgctggaa gatggaaccg ctggagagca actgcataag   3000
gctatgaaga gatacgccct ggttcctgga acaattgctt ttacagatgc acatatcgag   3060
gtggacatca cttacgctga gtacttcgaa atgtccgttc ggttggcaga agctatgaaa   3120
```

-continued

```
cgatatgggc tgaatacaaa tcacagaatc gtcgtatgca gtgaaaactc tcttcaattc   3180
tttatgccgg tgttgggcgc gttatttatc ggagttgcag ttgcgcccgc gaacgacatt   3240
tataatgaac gtgaattgct caacagtatg ggcatttcgc agcctaccgt ggtgttcgtt   3300
tccaaaaagg ggttgcaaaa aattttgaac gtgcaaaaaa agctcccaat catccaaaaa   3360
attattatca tggattctaa aacggattac cagggatttc agtcgatgta cacgttcgtc   3420
acatctcatc tacctcccgg ttttaatgaa tacgattttg tgccagagtc cttcgatagg   3480
gacaagacaa ttgcactgat catgaactcc tctggatcta ctggtctgcc taaaggtgtc   3540
gctctgcctc atagaactgc ctgcgtgaga ttctcgcatg ccagagatcc tatttttggc   3600
aatcaaatca ttccggatac tgcgatttta agtgttgttc cattccatca cggttttgga   3660
atgtttacta cactcggata tttgatatgt ggatttcgag tcgtcttaat gtatagattt   3720
gaagaagagc tgtttctgag gagccttcag gattacaaga ttcaaagtgc gctgctggtg   3780
ccaaccctat tctccttctt cgccaaaagc actctgattg acaaatacga tttatctaat   3840
ttacacgaaa ttgcttctgg tggcgctccc ctctctaagg aagtcgggga agcggttgcc   3900
aagaggttcc atctgccagg tatcaggcaa ggatatgggc tcactgagac tacatcagct   3960
attctgatta cacccgaggg ggatgataaa ccgggcgcgg tcggtaaagt tgttccattt   4020
tttgaagcga aggttgtgga tctggatacc gggaaaacgc tgggcgttaa tcaaagaggc   4080
gaactgtgtg tgagaggtcc tatgattatg tccggttatg taaacaatcc ggaagcgacc   4140
aacgccttga ttgacaagga tggatggcta cattctggag acatagctta ctgggacgaa   4200
gacgaacact tcttcatcgt tgaccgcctg aagtctctga ttaagtacaa aggctatcag   4260
gtggctcccg ctgaattgga atccatcttg ctccaacacc ccaacatctt cgacgcaggt   4320
gtcgcaggtc ttcccgacga tgacgccggt gaacttcccg ccgccgttgt tgttttggag   4380
cacggaaaga cgatgacgga aaaagagatc gtggattacg tcgccagtca agtaacaacc   4440
gcgaaaaagt tgcgcggagg agttgtgttt gtggacgaag taccgaaagg tcttaccgga   4500
aaactcgacg caagaaaaat cagagagatc ctcataaagg ccaagaaggg cggaaagatc   4560
gccgtgtaac tcgagcatat gggctcgaat ttccccgatc gttcaaacat ttggcaataa   4620
agtttcttaa gattgaatcc tgttgccggt cttgcgatga ttatcatata atttctgttg   4680
aattacgtta agcatgtaat aattaacatg taatgcatga cgttatttat gagatgggtt   4740
tttatgatta gagtcccgca attatacatt taatacgcga tagaaaacaa aatatagcgc   4800
gcaaactagg ataaattatc gcgcgcggtg tcatctatgt tactagatcg ggaattcaag   4860
cttggcgtaa tcatggaccc agctttcttg tacaaagtgg ggtaccaatt cgaatccaaa   4920
aattacggat atgaatatag gcatatccgt atccgaatta tccgtttgac agctagcaac   4980
gattgtacaa ttgcttcttt aaaaaaggaa gaaagaaaga aagaaaagaa tcaacatcag   5040
cgttaacaaa cggccccgtt acggcccaaa cggtcatata gagtaacggc gttaagcgtt   5100
gaaagactcc tatcgaaata cgtaaccgca aacgtgtcat agtcagatcc cctcttcctt   5160
caccgcctca aacacaaaaa taatcttcta cagcctatat atacaacccc cccttctatc   5220
tctcctttct cacaattcat catctttctt tctctacccc caattttaag aaatcctctc   5280
ttctcctctt cattttcaag gtaaatctct ctctctctct ctctctctgt tattccttgt   5340
tttaattagg tatgtattat tgctagtttg ttaatctgct tatcttatgt atgccttatg   5400
tgaatatctt tatcttgttc atctcatccg tttagaagct ataaatttgt tgatttgact   5460
gtgtatctac acgtggttat gtttatatct aatcagatat gaatttcttc atattgttgc   5520
```

```
gtttgtgtgt accaatccga aatcgttgat ttttttcatt taatcgtgta gctaattgta   5580
cgtatacata tggatctacg tatcaattgt tcatctgttt gtgtttgtat gtatacagat   5640
ctgaaaacat cacttctctc atctgattgt gttgttacat acatagatat agatctgtta   5700
tatcattttt tttattaatt gtgtatatat atatgtgcat agatctggat tacatgattg   5760
tgattattta catgattttg ttatttacgt atgtatatat gtagatctgg actttttgga   5820
gttgttgact tgattgtatt tgtgtgtgta tatgtgtgtt ctgatcttga tatgttatgt   5880
atgtgcagct gaaccatggc ggcggcaaca acaacaacaa caacatcttc ttcgatctcc   5940
ttctccacca aaccatctcc ttcctcctcc aaatcaccat taccaatctc cagattctcc   6000
ctcccattct ccctaaaccc caacaaatca tcctcctcct cccgccgccg cggtatcaaa   6060
tccagctctc cctcctccat ctccgccgtg ctcaacacaa ccaccaatgt cacaaccact   6120
ccctctccaa ccaaacctac caaacccgaa acattcatct cccgattcgc tccagatcaa   6180
ccccgcaaag gcgctgatat cctcgtcgaa gctttagaac gtcaaggcgt agaaaccgta   6240
ttcgcttacc ctggaggtac atcaatggag attcaccaag ccttaacccg ctcttcctca   6300
atccgtaacg tccttcctcg tcacgaacaa ggaggtgtat tcgcagcaga aggatacgct   6360
cgatcctcag gtaaaccagg tatctgtata gccacttcag gtcccggagc tacaaatctc   6420
gttagcggat tagccgatgc gttgttagat agtgttcctc ttgtagcaat cacaggacaa   6480
gtccctcgtc gtatgattgg tacagatgcg tttcaagaga ctccgattgt tgaggtaacg   6540
cgttcgatta cgaagcataa ctatcttgtg atggatgttg aagatatccc taggattatt   6600
gaggaagctt tctttttagc tacttctggt agacctggac ctgttttggt tgatgttcct   6660
aaagatattc aacaacagct tgcgattcct aattgggaac aggctatgag attacctggt   6720
tatatgtcta ggatgcctaa acctccggaa gattctcatt tggagcagat tgttaggttg   6780
atttctgagt ctaagaagcc tgtgttgtat gttggtggtg gttgtttgaa ttctagcgat   6840
gaattgggta ggtttgttga gcttacgggg atccctgttg cgagtacgtt gatggggctg   6900
ggatcttatc cttgtgatga tgagttgtcg ttacatatgc ttggaatgca tgggactgtg   6960
tatgcaaatt acgctgtgga gcatagtgat ttgttgttgg cgtttggggt aaggtttgat   7020
gatcgtgtca cgggtaagct tgaggctttt gctagtaggg ctaagattgt tcatattgat   7080
attgactcgg ctgagattgg gaagaataag actcctcatg tgtctgtgtg tggtgatgtt   7140
aagctggctt tgcaagggat gaataaggtt cttgagaacc gagcggagga gcttaagctt   7200
gattttggag tttggaggaa tgagttgaac gtacagaaac agaagtttcc gttgagcttt   7260
aagacgtttg gggaagctat tcctccacag tatgcgatta aggtccttga tgagttgact   7320
gatggaaaag ccataataag tactggtgtc gggcaacatc aaatgtgggc ggcgcagttc   7380
tacaattaca agaaaccaag gcagtggcta tcatcaggag gccttggagc tatgggattt   7440
ggacttcctg ctgcgattgg agcgtctgtt gctaaccctg atgcgatagt tgtggatatt   7500
gacggagatg gaagctttat aatgaatgtg caagagctag ccactattcg tgtagagaat   7560
cttccagtga aggtactttt attaaacaac cagcatcttg gcatggttat gcaatgggaa   7620
gatcggttct acaaagctaa ccgagctcac acatttctcg ggatccggct tcaggaggac   7680
gagatattcc cgaacatgtt gctgtttgca gcagcttgcg ggattccagc ggcgagggtg   7740
acaaagaaag cagatctccg agaagctatt cagacaatgc tggatacacc aggaccttac   7800
ctgttggatg tgatttgtcc gcaccaagaa catgtgttgc cgatgatccc gaatggtggc   7860
```

```
actttcaacg atgtcataac ggaaggagat ggccggatta aatactgaga gatgaaaccg   7920
gtgattatca gaacctttta tggtctttgt atgcatatgg taaaaaaact tagtttgcaa   7980
tttcctgttt gttttggtaa tttgagtttc ttttagttgt tgatctgcct gctttttggt   8040
ttacgtcaga ctactactgc tgttgttgtt tggtttcctt tctttcattt tataaataaa   8100
taatccggtt cggtttactc cttgtgactg gctcagtttg gttattgcga aatgcgaatg   8160
gtaaattgag taattgaaat tcgttattag ggttctaagc tgttttaaca gtcactgggt   8220
taatatctct cgaatcttgc atggaaaatg ctcttaccat tggtttttaa ttgaaatgtg   8280
ctcatatggg ccgtggtttc caaattaaat aaaactacga tgtcatcgag aagtaaaatc   8340
aactgtgtcc acattatcag ttttgtgtat acgatgaaat agggtaattc aaaatctagc   8400
ttgatatgcc ttttggttca ttttaacctt ctgtaaacat tttttcagat tttgaacaag   8460
taaatccaaa aaaaaaaaaa aaaaatctca actcaacact aaattatttt aatgtataaa   8520
agatgcttaa aacatttggc ttaaaagaaa gaagctaaaa acatagagaa ctcttgtaaa   8580
ttgaagtatg aaaatatact gaattgggta ttatatgaat ttttctgatt taggattcac   8640
atgatccaaa aaggaaatcc agaagcacta atcagacatt ggaagtagga atatttcaaa   8700
aagttttttt tttttaagta agtgacaaaa gcttttaaaa aatagaaaag aaactagtat   8760
taaagttgta aatttaataa acaaaagaaa tttttttatat tttttcattt ctttttccag   8820
catgaggtta tgatggcagg atgtggattt catttttttc cttttgatag ccttttaatt   8880
gatctattat aattgacgaa aaaatattag ttaattatag atatatttta ggtagtatta   8940
gcaatttaca cttccaaaag actatgtaag ttgtaaatat gatgcgttga tctcttcatc   9000
attcaatggt tagtcaaaaa aataaaagct taactagtaa actaaagtag tcaaaaattg   9060
tactttagtt taaaatatta catgaataat ccaaaacgac atttatgtga aacaaaaaca   9120
atatctagag tcgacttaat taaactagtg gcgcgccaat tgactagtag gcctatcgat   9180
taattaaggc cgcctcgagc atatgggcat gcaagcttgg cgtaatcatg gcaactttat   9240
tatacatagt tgataattca ctggccggat ctgcttggta ataattgtca ttagattgtt   9300
tttatgcata gatgcactcg aaatcagcca attttagaca agtatcaaac ggatgttaat   9360
tcagtacatt aaagacgtcc gcaatgtgtt attaagttgt ctaagcgtca atttgtttac   9420
accacaatat atcctgccac cagccagcca acagctcccc gaccggcagc tcggcacaaa   9480
atcaccacgc gttaccacca cgccggccgg ccgcatggtg ttgaccgtgt tcgccggcat   9540
tgccgagttc gagcgttccc taatcatcga ccgcacccgg agcgggcgcg aggccgccaa   9600
ggcccgaggc gtgaagtttg gcccccgccc taccctcacc ccggcacaga tcgcgcacgc   9660
ccgcgagctg atcgaccagg aaggccgcac cgtgaaagag gcggctgcac tgcttggcgt   9720
gcatcgctcg accctgtacc gcgcacttga gcgcagcgag gaagtgacgc ccaccgaggc   9780
caggcggcgc ggtgccttcc gtgaggacgc attgaccgag gccgacgccc tggcggccgc   9840
cgagaatgaa cgccaagagg aacaagcatg aaaccgcacc aggacggcca ggacgaaccg   9900
tttttcatta ccgaagagat cgaggcggag atgatcgcgg ccgggtacgt gttcgagccg   9960
cccgcgcacg tctcaaccgt gcggctgcat gaaatcctgg ccggtttgtc tgatgccaag  10020
ctggcggcct ggccggccag cttggccgct gaagaaaccg agcgccgccg tctaaaaagg  10080
tgatgtgtat ttgagtaaaa cagcttgcgt catgcggtcg ctgcgtatat gatgcgatga  10140
gtaaataaac aaatacgcaa ggggaacgca tgaaggttat cgctgtactt aaccagaaag  10200
gcgggtcagg caagacgacc atcgcaaccc atctagcccg cgccctgcaa ctcgccgggg  10260
```

```
ccgatgttct gttagtcgat tccgatcccc agggcagtgc ccgcgattgg gcggccgtgc  10320
gggaagatca accgctaacc gttgtcggca tcgaccgccc gacgattgac cgcgacgtga  10380
aggccatcgg ccggcgcgac ttcgtagtga tcgacggagc gccccaggcg gcggacttgg  10440
ctgtgtccgc gatcaaggca gccgacttcg tgctgattcc ggtgcagcca agcccttacg  10500
acatatgggc caccgccgac ctggtggagc tggttaagca gcgcattgag gtcacggatg  10560
gaaggctaca agcggccttt gtcgtgtcgc gggcgatcaa aggcacgcgc atcggcggtg  10620
aggttgccga ggcgctggcc gggtacgagc tgcccattct tgagtcccgt atcacgcagc  10680
gcgtgagcta cccaggcact gccgccgccg gcacaaccgt tcttgaatca gaacccgagg  10740
gcgacgctgc ccgcgaggtc caggcgctgg ccgctgaaat taaatcaaaa ctcatttgag  10800
ttaatgaggt aaagagaaaa tgagcaaaag cacaaacacg ctaagtgccg gccgtccgag  10860
cgcacgcagc agcaaggctg caacgttggc cagcctggca gacacgccag ccatgaagcg  10920
ggtcaacttt cagttgccgg cggaggatca caccaagctg aagatgtacg cggtacgcca  10980
aggcaagacc attaccgagc tgctatctga atacatcgcg cagctaccag agtaaatgag  11040
caaatgaata aatgagtaga tgaattttag cggctaaagg aggcggcatg gaaaatcaag  11100
aacaaccagg caccgacgcc gtggaatgcc ccatgtgtgg aggaacgggc ggttggccag  11160
gcgtaagcgg ctgggttgtc tgccggccct gcaatggcac tggaaccccc aagcccgagg  11220
aatcggcgtg agcggtcgca aaccatccgg cccggtacaa atcggcgcgg cgctgggtga  11280
tgacctggtg gagaagttga aggccgcgca ggccgcccag cggcaacgca tcgaggcaga  11340
agcacgcccc ggtgaatcgt ggcaagcggc cgctgatcga atccgcaaag aatcccggca  11400
accgccggca gccggtgcgc cgtcgattag gaagccgccc aagggcgacg agcaaccaga  11460
tttttcgtt ccgatgctct atgacgtggg cacccgcgat agtcgcagca tcatggacgt  11520
ggccgttttc cgtctgtcga agcgtgaccg acgagctggc gaggtgatcc gctacgagct  11580
tccagacggg cacgtagagg tttccgcagg gccggccggc atggccagtg tgtgggatta  11640
cgacctggta ctgatggcgg tttcccatct aaccgaatcc atgaaccgat accgggaagg  11700
gaagggagac aagcccggcc gcgtgttccg tccacacgtt gcggacgtac tcaagttctg  11760
ccggcgagcc gatggcggaa agcagaaaga cgacctggta gaaacctgca ttcggttaaa  11820
caccacgcac gttgccatgc agcgtacgaa gaaggccaag aacggccgcc tggtgacggt  11880
atccgagggt gaagccttga ttagccgcta caagatcgta aagagcgaaa ccgggcggcc  11940
ggagtacatc gagatcgagc tagctgattg gatgtaccgc gagatcacag aaggcaagaa  12000
cccggacgtg ctgacggttc accccgatta ctttttgatc gatcccggca tcggccgttt  12060
tctctaccgc ctggcacgcc gcgccgcagg caaggcagaa gccagatggt tgttcaagac  12120
gatctacgaa cgcagtggca gcgccggaga gttcaagaag ttctgtttca ccgtgcgcaa  12180
gctgatcggg tcaaatgacc tgccggagta cgatttgaag gaggaggcgg ggcaggctgg  12240
cccgatccta gtcatgcgct accgcaacct gatcgagggc gaagcatccg ccggttccta  12300
atgtacggag cagatgctag ggcaaattgc cctagcaggg gaaaaaggtc gaaaaggtct  12360
ctttcctgtg gatagcacgt acattgggaa cccaaagccg tacattggga accggaaccc  12420
gtacattggg aacccaaagc cgtacattgg gaaccggtca cacatgtaag tgactgatat  12480
aaaagagaaa aaaggcgatt tttccgccta aaactcttta aaacttatta aaactcttaa  12540
aacccgcctg gcctgtgcat aactgtctgg ccagcgcaca gccgaagagc tgcaaaaagc  12600
```

```
gcctaccctt cggtcgctgc gctccctacg ccccgccgct tcgcgtcggc ctatcgcggc  12660

cgctggccgc tcaaaaatgg ctggcctacg gccaggcaat ctaccagggc gcggacaagc  12720

cgcgccgtcg ccactcgacc gccggcgccc acatcaaggc accctgcctc gcgcgtttcg  12780

gtgatgacgg tgaaaacctc tgacacatgc agctcccgga gacggtcaca gcttgtctgt  12840

aagcggatgc cgggagcaga caagcccgtc agggcgcgtc agcgggtgtt ggcgggtgtc  12900

ggggcgcagc catgacccag tcacgtagcg atagcggagt gtatactggc ttaactatgc  12960

ggcatcagag cagattgtac tgagagtgca ccatatgcgg tgtgaaatac cgcacagatg  13020

cgtaaggaga aaataccgca tcaggcgctc ttccgcttcc tcgctcactg actcgctgcg  13080

ctcggtcgtt cggctgcggc gagcggtatc agctcactca aaggcggtaa tacggttatc  13140

cacagaatca ggggataacg caggaaagaa catgtgagca aaaggccagc aaaaggccag  13200

gaaccgtaaa aaggccgcgt tgctggcgtt tttccatagg ctccgccccc ctgacgagca  13260

tcacaaaaat cgacgctcaa gtcagaggtg gcgaaacccg acaggactat aaagatacca  13320

ggcgtttccc cctggaagct ccctcgtgcg ctctcctgtt ccgaccctgc cgcttaccgg  13380

atacctgtcc gcctttctcc cttcgggaag cgtggcgctt tctcatagct cacgctgtag  13440

gtatctcagt tcggtgtagg tcgttcgctc caagctgggc tgtgtgcacg aaccccccgt  13500

tcagcccgac cgctgcgcct tatccggtaa ctatcgtctt gagtccaacc cggtaagaca  13560

cgacttatcg ccactggcag cagccactgg taacaggatt agcagagcga ggtatgtagg  13620

cggtgctaca gagttcttga agtggtggcc taactacggc tacactagaa ggacagtatt  13680

tggtatctgc gctctgctga agccagttac cttcggaaaa agagttggta gctcttgatc  13740

cggcaaacaa accaccgctg gtagcggtgg tttttttgtt tgcaagcagc agattacgcg  13800

cagaaaaaaa ggatctcaag aagatccttt gatcttttct acggggtctg acgctcagtg  13860

gaacgaaaac tcacgttaag ggattttggt catgcatgat atatctccca atttgtgtag  13920

ggcttattat gcacgcttaa aaataataaa agcagacttg acctgatagt ttggctgtga  13980

gcaattatgt gcttagtgca tctaacgctt gagttaagcc gcgccgcgaa gcggcgtcgg  14040

cttgaacgaa tttctagcta gacattattt gccgactacc ttggtgatct cgcctttcac  14100

gtagtggaca aattcttcca actgatctgc gcgcgaggcc aagcgatctt cttcttgtcc  14160

aagataagcc tgtctagctt caagtatgac gggctgatac tgggccggca ggcgctccat  14220

tgcccagtcg gcagcgacat ccttcggcgc gattttgccg gttactgcgc tgtaccaaat  14280

gcgggacaac gtaagcacta catttcgctc atcgccagcc cagtcgggcg gcgagttcca  14340

tagcgttaag gtttcattta gcgcctcaaa tagatcctgt tcaggaaccg gatcaaagag  14400

ttcctccgcc gctggaccta ccaaggcaac gctatgttct cttgcttttg tcagcaagat  14460

agccagatca atgtcgatcg tggctggctc gaagatacct gcaagaatgt cattgcgctg  14520

ccattctcca aattgcagtt cgcgcttagc tggataacgc cacggaatga tgtcgtcgtg  14580

cacaacaatg gtgacttcta cagcgcggag aatctcgctc tctccagggg aagccgaagt  14640

ttccaaaagg tcgttgatca aagctcgccg cgttgtttca tcaagcctta cggtcaccgt  14700

aaccagcaaa tcaatatcac tgtgtggctt caggccgcca tccactgcgg agccgtacaa  14760

atgtacggcc agcaacgtcg gttcgagatg gcgctcgatg acgccaacta cctctgatag  14820

ttgagtcgat acttcggcga tcaccgcttc ccccatgatg tttaactttg ttttagggcg  14880

actgccctgc tgcgtaacat cgttgctgct ccataacatc aaacatcgac ccacggcgta  14940

acgcgcttgc tgcttggatg cccgaggcat agactgtacc ccaaaaaaac agtcataaca  15000
```

agccatgaaa accgccactg cgttccatg 15029

<210> SEQ ID NO 68
<211> LENGTH: 38
<212> TYPE: DNA
<213> ORGANISM: Artificial Sequence
<220> FEATURE:
<223> OTHER INFORMATION: synthetic sequence

<400> SEQUENCE: 68
aataatggcg cgcctggtgc ttaaacactc tggtgagt 38

<210> SEQ ID NO 69
<211> LENGTH: 40
<212> TYPE: DNA
<213> ORGANISM: Artificial Sequence
<220> FEATURE:
<223> OTHER INFORMATION: synthetic sequence

<400> SEQUENCE: 69
aataatggcg cgcctttgac ctacaaaatc aaagcagtca 40

<210> SEQ ID NO 70
<211> LENGTH: 36
<212> TYPE: DNA
<213> ORGANISM: Artificial Sequence
<220> FEATURE:
<223> OTHER INFORMATION: synthetic sequence

<400> SEQUENCE: 70
ttttttggcg cgccagttct ttgctttcga agttgc 36

<210> SEQ ID NO 71
<211> LENGTH: 37
<212> TYPE: DNA
<213> ORGANISM: Artificial Sequence
<220> FEATURE:
<223> OTHER INFORMATION: synthetic sequence

<400> SEQUENCE: 71
ttttttggcg cgcctactac gtactgtttt caattct 37

<210> SEQ ID NO 72
<211> LENGTH: 35
<212> TYPE: DNA
<213> ORGANISM: Artificial Sequence
<220> FEATURE:
<223> OTHER INFORMATION: synthetic sequence

<400> SEQUENCE: 72
aataaaggcg cgccgtccag aattttctcc attga 35

<210> SEQ ID NO 73
<211> LENGTH: 36
<212> TYPE: DNA
<213> ORGANISM: Artificial Sequence
<220> FEATURE:
<223> OTHER INFORMATION: synthetic sequence

<400> SEQUENCE: 73
aataaaggcg cgcctcttca ctatccaaag ctctca 36

<210> SEQ ID NO 74
<211> LENGTH: 39
<212> TYPE: DNA

<213> ORGANISM: Artificial Sequence
<220> FEATURE:
<223> OTHER INFORMATION: synthetic sequence

<400> SEQUENCE: 74
ttttatggcg cgcctagctt aatctcagat tcgaatcgt 39

<210> SEQ ID NO 75
<211> LENGTH: 42
<212> TYPE: DNA
<213> ORGANISM: Artificial Sequence
<220> FEATURE:
<223> OTHER INFORMATION: synthetic sequence

<400> SEQUENCE: 75
ttttatggcg cgcctagtat ctacatacca atcatacaaa tg 42

<210> SEQ ID NO 76
<211> LENGTH: 34
<212> TYPE: DNA
<213> ORGANISM: Artificial Sequence
<220> FEATURE:
<223> OTHER INFORMATION: synthetic sequence

<400> SEQUENCE: 76
ttttttggcg cgcctttcac gatttggaat ttga 34

<210> SEQ ID NO 77
<211> LENGTH: 38
<212> TYPE: DNA
<213> ORGANISM: Artificial Sequence
<220> FEATURE:
<223> OTHER INFORMATION: synthetic sequence

<400> SEQUENCE: 77
ttttttggcg cgcctctaca acattaaaac gaccatta 38

<210> SEQ ID NO 78
<211> LENGTH: 34
<212> TYPE: DNA
<213> ORGANISM: Artificial Sequence
<220> FEATURE:
<223> OTHER INFORMATION: synthetic sequence

<400> SEQUENCE: 78
tatataggcg cgccagggtt tcgtttttgt ttca 34

<210> SEQ ID NO 79
<211> LENGTH: 37
<212> TYPE: DNA
<213> ORGANISM: Artificial Sequence
<220> FEATURE:
<223> OTHER INFORMATION: synthetic sequence

<400> SEQUENCE: 79
tatataggcg cgccttatct cctgctcaaa gaaacca 37

<210> SEQ ID NO 80
<211> LENGTH: 35
<212> TYPE: DNA
<213> ORGANISM: Artificial Sequence
<220> FEATURE:
<223> OTHER INFORMATION: synthetic sequence

<400> SEQUENCE: 80
tatataggcg cgccactgtt taagcttcac tgtct 35

<210> SEQ ID NO 81
<211> LENGTH: 34
<212> TYPE: DNA
<213> ORGANISM: Artificial Sequence
<220> FEATURE:
<223> OTHER INFORMATION: synthetic sequence

<400> SEQUENCE: 81
tatataggcg cgcctttctt ctaaagctga aagt 34

<210> SEQ ID NO 82
<211> LENGTH: 14495
<212> TYPE: DNA
<213> ORGANISM: Artificial Sequence
<220> FEATURE:
<223> OTHER INFORMATION: vector sequence

<400> SEQUENCE: 82
gtgattttgt gccgagctgc cggtcgggga gctgttggct ggctggtggc aggatatatt 60
gtggtgtaaa caaattgacg cttagacaac ttaataacac attgcggacg tctttaatgt 120
actgaattta gttactgatc actgattaag tactgatatc ggtaccaagc ttccgcggct 180
gcagtgcagc gtgacccggt cgtgcccctc tctagagata atgagcattg catgtctaag 240
ttataaaaaa ttaccacata tttttttgt cacacttgtt tgaagtgcag tttatctatc 300
tttatacata tatttaaact ttactctacg aataatataa tctatagtac tacaataata 360
tcagtgtttt agagaatcat ataaatgaac agttagacat ggtctaaagg acaattgagt 420
attttgacaa caggactcta cagttttatc tttttagtgt gcatgtgttc tcctttttt 480 ttgcaaatag cttcacctat ataatacttc atccatttta ttagtacatc catttagggt 540
ttagggttaa tggtttttat agactaattt ttttagtaca tctattttat tctattttag 600
cctctaaatt aagaaaacta aaactctatt ttagtttttt tatttaatag tttagatata 660
aaatagaata aaataaagtg actaaaaatt aaacaaatac cctttaagaa attaaaaaaa 720
ctaaggaaac atttttcttg tttcgagtag ataatgccag cctgttaaac gccgtcgacg 780
agtctaacgg acaccaacca gcgaaccagc agcgtcgcgt cgggccaagc gaagcagacg 840
gcacggcatc tctgtcgctg cctctggacc cctctcgaga gttccgctcc accgttggac 900
ttgctccgct gtcggcatcc agaaattgcg tggcggagcg gcagacgtga gccggcacgg 960
caggcggcct cctcctcctc tcacggcacc ggcagctacg gggattcct ttcccaccgc 1020 tccttcgctt tcccttcctc gcccgccgta ataaatagac accccctcca caccctcttt 1080
ccccaacctc gtgttgttcg gagcgcacac acacacaacc agatctcccc caaatccacc 1140
cgtcggcacc tccgcttcaa ggtacgccgc tcgtcctccc cccccccccc cctctctacc 1200
ttctctagat cggcgttccg gtccatggtt agggcccggt agttctactt ctgttcatgt 1260
ttgtgttaga tccgtgtttg tgttagatcc gtgctgctag cgttcgtaca cggatgcgac 1320
ctgtacgtca gacacgttct gattgctaac ttgccagtgt ttctctttgg ggaatcctgg 1380
gatggctcta gccgttccgc agacgggatc gatttcatga ttttttttgt ttcgttgcat 1440
agggtttggt ttgccctttt cctttatttc aatatatgcc gtgcacttgt ttgtcgggtc 1500
atcttttcat gctttttttt gtcttggttg tgatgatgtg gtctggttgg gcggtcgttc 1560
tagatcggag tagaattctg tttcaaacta cctggtggat ttattaattt tggatctgta 1620
tgtgtgtgcc atacatattc atagttacga attgaagatg atggatggaa atatcgatct 1680

-continued

```
aggataggta tacatgttga tgcgggtttt actgatgcat atacagagat gctttttgtt   1740
cgcttggttg tgatgatgtg gtgtggttgg gcggtcgttc attcgttcta gatcggagta   1800
gaatactgtt tcaaactacc tggtgtattt attaattttg gaactgtatg tgtgtgtcat   1860
acatcttcat agttacgagt ttaagatgga tggaaatatc gatctaggat aggtatacat   1920
gttgatgtgg gttttactga tgcatataca tgatggcata tgcagcatct attcatatgc   1980
tctaaccttg agtacctatc tattataata aacaagtatg ttttataatt atttcgatct   2040
tgatatactt ggatgatggc atatgcagca gctatatgtg gattttttta gccctgcctt   2100
catacgctat ttatttgctt ggtactgttt cttttgtcga tgctcaccct gttgtttggt   2160
gttacttctg cagcccgggg gatccactag ttctagaaac catggccacc gccgccgccg   2220
cgtctaccgc gctcactggc gccactaccg ctgcgcccaa ggcgaggcgc cgggcgcacc   2280
tcctggccac ccgccgcgcc ctcgccgcgc ccatcaggtg ctcagcggcg tcacccgcca   2340
tgccgatggc tcccccggcc accccgctcc ggccgtgggg ccccaccgat ccccgcaagg   2400
gcgccgacat cctcgtcgag tccctcgagc gctgcggcgt ccgcgacgtc ttcgcctacc   2460
ccggcggcac gtccatggag atccaccagg cactcacccg ctcccccgtc atcgccaacc   2520
acctcttccg ccacgagcaa ggggaggcct ttgcggcctc cggctacgcg cgctcctcgg   2580
gccgcgtcgg cgtctgcatc gccacctccg gccccggcgc caccaacctt gtctccgcgc   2640
tcgccgacgc gctgctcgat tccgtcccca tggtcgccat cacgggacag gtgccgcgac   2700
gcatgattgg caccgacgcc ttccaggaga cgcccatcgt cgaggtcacc cgctccatca   2760
ccaagcacaa ctacctggtc ctcgacgtcg acgacatccc ccgcgtcgtg caggaggctt   2820
tcttcctcgc ctcctctggt cgaccggggc cggtgcttgt cgacatcccc aaggacatcc   2880
agcagcagat ggcggtgcct gtctgggaca agcccatgag tctgcctggg tacattgcgc   2940
gccttcccaa gccccctgcg actgagttgc ttgagcaggt gctgcgtctt gttggtgaat   3000
cccggcgccc tgttctttat gttggcggtg gctgcgcagc atctggtgag gagttgcgac   3060
gctttgtgga gctgactgga atcccggtca caactactct tatgggcctc ggcaacttcc   3120
ccagcgacga cccactgtct ctgcgcatgc taggtatgca tggcacggtg tatgcaaatt   3180
atgcagtgga taaggccgat ctgttgcttg cacttggtgt gcggtttgat gatcgtgtga   3240
cagggaagat tgaggctttt gcaagcaggg ctaagattgt gcacgttgat attgatccgg   3300
ctgagattgg caagaacaag cagccacatg tgtccatctg tgcagatgtt aagcttgctt   3360
tgcagggcat gaatgctctt cttgaaggaa gcacatcaaa gaagagcttt gactttggct   3420
catggaacga tgagttggat cagcagaaga gggaattccc ccttgggtat aaaacatcta   3480
atgaggagat ccagccacaa tatgctattc aggttcttga tgagctgacg aaaggcgagg   3540
ccatcatcgg cacaggtgtt gggcagcacc agatgtgggc ggcacagtac tacacttaca   3600
agcggccaag gcagtggttg tcttcagctg gtcttggggc tatgggattt ggtttgccgg   3660
ctgctgctgg tgcttctgtg gccaacccag gtgttactgt tgttgacatc gatggagatg   3720
gtagctttct catgaacgtt caggagctag ctatgatccg aattgagaac ctcccggtga   3780
aggtctttgt gctaaacaac cagcacctgg ggatggtggt gcagtgggag gacaggttct   3840
ataaggccaa cagagcgcac acatacttgg gaaacccaga gaatgaaagt gagatatatc   3900
cagatttcgt gacgatcgcc aaagggttca acattccagc ggtccgtgtg acaaagaaga   3960
acgaagtccg cgcagcgata aagaagatgc tcgagactcc agggccgtac ctcttggata   4020
taatcgtccc acaccaggag catgtgttgc ctatgatccc taatggtggg gctttcaagg   4080
```

```
atatgatcct ggatggtgat ggcaggactg tgtactgatc taaaatccag caagcaactg   4140
atctaaaatc cagcaagcac cgcctccctg ctagtacaag ggtgatatgt ttttatctgt   4200
gtgatgttct cctgtattct atcttttttt gtaggccgtc agctatctgt tatggtaatc   4260
ctatgtagct tccgaccttg taattgtgta gtctgttgtt ttccttctgg catgtgtcat   4320
aagagatcat ttaagtgcct tttgctacat ataaataaga taataagcac tgctatgcag   4380
tggttctgaa ttggcttctg ttgccaaatt taagtgtcca actggtcctt gcttttgttt   4440
tcgctatttt tttccttttt tagttattat tatattggta atttcaactc aacatatgat   4500
gtatggaata atgctagggc tgcaatttca aactatttta caaaccagaa tggcattttc   4560
gtggtttgag gggagtgaaa aaaaatgagg catttgactg aattagttac ctgatccatt   4620
ttcgtggttt ggatcattgg aattaaattc cattctaata atagtaattt tggcatatat   4680
caattaagtt aattcggttt tatgcaaaat atatttgtat actattatta tcaagatgtc   4740
ggagatattt atatgctaca tttttactat acaggagtga gatgaagagt gtcatgtaag   4800
ttacacagta gaaacaaatt ctattaatgc ataaaatcat ttccatcatc caccctatga   4860
atttgagata gacctatatc taaactttga aaagtggttg aatatcaaat tccaaattaa   4920
ataagttatt ttattgagtg aattctaatt tctctaaaac gaagggatct aaacgccctc   4980
taaagctaat ttggaaactc aaactttctt agcattggag gggattgaga aaaaatatta   5040
attcattttc atctcaatca ttcaatctcc aaagagattt gagttcctta ttagtctgtt   5100
ccatgcatca aatcggctca atgtgtcatt atttgccatg acgattgacg agttgttctg   5160
gggcctagcg ctttccacgc cgatgtgctg ggcctggtc ctggagaaga cagcttgata    5220
tttaaagcta tcaattgttt caattgattc ccacttcatt tttctaaatg tagaaaacgg   5280
tgacgtataa gaaaaagaat gaattaggac ttttattccg tacactaatc tagagcggcc   5340
caagcttgta cactagtacg cgtcaattga tttaaattta attaatcccg tgtccgtcaa   5400
tgtgatacta ctagcatagt actagtacca tgcatacaca cagcaggtcg gccgcctgga   5460
tggatcgatg atgatactac atcatcctgt catccatcca ggcgatctag aaggggcgtg   5520
gctagctagc aaactgtgac cggtttttct acgccgataa taatactttg tcatggtaca   5580
gacgtacagt actggttata tatatctgta gatttcaact gaaaagctag gatagctaga   5640
ttaattcctg agaaacacag ataaaattcg agcttggcta tagatgacaa aacggaagac   5700
gcatgcattg gacgacgtat gcaatgcgag cgcgtctcgt gtcgtcccgt ccaagtctgg   5760
cgatctcacg ccacgtgctc aacagctcaa ggactgttcg tcaccagcgt taaattcatt   5820
gaagggatga cgcatttcgg catttgtcat tgcttgtagc tatatatata tatccaacag   5880
atttctctca agcttttgta tgcgtgaatg taaagtctag cttatacgac agcacgtgca   5940
gatatattaa cgtcattatt aggtggagag caagatgcat gatctggtag aaattgtcga   6000
aaacacaaga gagagtgaag tgcacacttc tggtatagga gtgtatacgc cgctggttgg   6060
tgggcaatgc gcgccgcaat attggccaat gaaacctagc aacgcccact cgccacgccc   6120
catgaatggc ccccgcacgg cagcgagcca gccagtgccc gcgcgcggcc cagccggagt   6180
cggcggaacg cgccacgggg gacgaggcgc ccgagggccg aggcagcgcg gcatggcaag   6240
caagccgaag cgggcaagcg acctgcatgc agcccctgcc cctcgccctc gtcagtcgtc   6300
ccagcctccc actggaatcc acccaacccg cccttcctct ccaaagcacg cgccccgcga   6360
ctcgcctccg cctacgtgtc ggcagcgtcc ccgccggtcg cccacgtacc ccgccccgtt   6420
```

```
ctcccacgtg cccctccctc tgcgcgcgtc cgattggctg acccgccctt cttaagccgc   6480
gccagcctcc tgtccgggcc ccaacgccgt gctccgtcgt cgtctccgcc cccagagtga   6540
tcgagcccac tgacctggcc cccgagcctc agctcgtgag tccggcgcgc ctggtgctta   6600
aacactctgg tgagttctag tacttctgct atgatcgatc tcattaccat ttcttaaatt   6660
tctctcccta aatattccga gttcttgatt tttgataact tcaggttttc tctttttgat   6720
aaatctggtc tttccatttt tttttttttg tggttaattt agtttcctat gttcttcgat   6780
tgtattatgc atgatctgtg tttggattct gttagattat gtattggtga atatgtatgt   6840
gtttttgcat gtctggtttt ggtcttaaaa atgttcaaat ctgatgattt gattgaagct   6900
tttttagtgt tggtttgatt cttctcaaaa ctactgttaa tttactatca tgttttccaa   6960
ctttgattca tgatgacact tttgttctgc tttgttataa aattttggtt ggtttgattt   7020
tgtaattata gtgtaatttt gttaggaatg aacatgtttt aatactctgt tttcgatttg   7080
tcacacattc gaattattaa tcgataattt aactgaaaat tcatggttct agatcttgtt   7140
gtcatcagat tatttgtttc gataattcat caaatatgta gtccttttgc tgatttgcga   7200
ctgtttcatt ttttctcaaa attgtttttt gttaagttta tctaacagtt atcgttgtca   7260
aaagtctctt tcattttgca aaatcttctt tttttttttg tttgtaactt tgttttttaa   7320
gctacacatt tagtctgtaa aatagcatcg aggaacagtt gtcttagtag acttgcatgt   7380
tcttgtaact tctatttgtt tcagtttgtt gatgactgct ttgattttgt aggtcaaagg   7440
cgcgccggat ccccgggtgg tcagtccctt atgttacgtc ctgtagaaac cccaacccgt   7500
gaaatcaaaa aactcgacgg cctgtgggca ttcagtctgg atcgcgaaaa ctgtggaatt   7560
gatcagcgtt ggtgggaaag cgcgttacaa gaaagccggg caattgctgt gccaggcagt   7620
tttaacgatc agttcgccga tgcagatatt cgtaattatg cgggcaacgt ctggtatcag   7680
cgcgaagtct ttataccgaa aggttgggca ggccagcgta tcgtgctgcg tttcgatgcg   7740
gtcactcatt acggcaaagt gtgggtcaat aatcaggaag tgatggagca tcagggcggc   7800
tatacgccat ttgaagccga tgtcacgccg tatgttattg ccgggaaaag tgtacgtaag   7860
tttctgcttc tacctttgat atatatataa taattatcat taattagtag taatataata   7920
tttcaaatat ttttttcaaa ataaaagaat gtagtatata gcaattgctt ttctgtagtt   7980
tataagtgtg tatattttaa tttataactt ttctaatata tgaccaaaat ttgttgatgt   8040
gcaggtatca ccgtttgtgt gaacaacgaa ctgaactggc agactatccc gccgggaatg   8100
gtgattaccg acgaaaacgg caagaaaaag cagtcttact tccatgattt ctttaactat   8160
gccggaatcc atcgcagcgt aatgctctac accacgccga acacctgggt ggacgatatc   8220
accgtggtga cgcatgtcgc gcaagactgt aaccacgcgt ctgttgactg gcaggtggtg   8280
gccaatggtg atgtcagcgt tgaactgcgt gatgcggatc aacaggtggt tgcaactgga   8340
caaggcacta gcgggacttt gcaagtggtg aatccgcacc tctggcaacc gggtgaaggt   8400
tatctctatg aactgtgcgt cacagccaaa agccagacag agtgtgatat ctacccgctt   8460
cgcgtcggca tccggtcagt ggcagtgaag ggcgaacagt tcctgattaa ccacaaaccg   8520
ttctacttta ctggctttgg tcgtcatgaa gatgcggact tgcgtggcaa aggattcgat   8580
aacgtgctga tggtgcacga ccacgcatta atggactgga ttggggccaa ctcctaccgt   8640
acctcgcatt acccttacgc tgaagagatg ctcgactggg cagatgaaca tggcatcgtg   8700
gtgattgatg aaactgctgc tgtcggcttt aacctctctt taggcattgg tttcgaagcg   8760
ggcaacaagc cgaaagaact gtacagcgaa gaggcagtca acggggaaac tcagcaagcg   8820
```

```
cacttacagg cgattaaaga gctgatagcg cgtgacaaaa accacccaag cgtggtgatg   8880
tggagtattg ccaacgaacc ggatacccgt ccgcaaggtg cacgggaata tttcgcgcca   8940
ctggcggaag caacgcgtaa actcgacccg acgcgtccga tcacctgcgt caatgtaatg   9000
ttctgcgacg ctcacaccga taccatcagc gatctctttg atgtgctgtg cctgaaccgt   9060
tattacggat ggtatgtcca aagcggcgat ttggaaacgg cagagaaggt actggaaaaa   9120
gaacttctgg cctggcagga gaaactgcat cagccgatta tcatcaccga atacggcgtg   9180
gatacgttag ccgggctgca ctcaatgtac accgacatgt ggagtgaaga gtatcagtgt   9240
gcatggctgg atatgtatca ccgcgtcttt gatcgcgtca gcgccgtcgt cggtgaacag   9300
gtatggaatt tcgccgattt tgcgacctcg caaggcatat tgcgcgttgg cggtaacaag   9360
aaagggatct tcactcgcga ccgcaaaccg aagtcggcgg cttttctgct gcaaaaacgc   9420
tggactggca tgaacttcgg tgaaaaaccg cagcagggag gcaaacaatg aatcaacaac   9480
tctcctggcg caccatcgtc ggctacagcc tcgggaattg ctaccgagct cctgcaggcc   9540
taggatcgtt caaacatttg gcaataaagt ttcttaagat tgaatcctgt tgccggtctt   9600
gcgatgatta tcatataatt tctgttgaat tacgttaagc atgtaataat taacatgtaa   9660
tgcatgacgt tatttatgag atgggttttt atgattagag tcccgcaatt atacatttaa   9720
tacgcgatag aaaacaaaat atagcgcgca aactaggata aattatcgcg cgcggtgtca   9780
tctatgttac tagatcggcc ggccgtttaa acttagttac taatcagtga tcagattgtc   9840
gtttcccgcc ttcactttaa actatcagtg tttgacagga tatattggcg ggtaaaccta   9900
agagaaaaga gcgtttatta gaataatcgg atatttaaaa gggcgtgaaa aggtttatcc   9960
gttcgtccat ttgtatgtca atattggggg ggggggaaag ccacgttgtg tctcaaaatc  10020
tctgatgtta cattgcacaa gataaaaata tatcatcatg aacaataaaa ctgtctgctt  10080
acataaacag taatacaagg ggtgttcgcc accatgagcc atatccagcg tgaaacctcg  10140
tgctcccgcc cgcgcctcaa ttccaatatg gatgccgacc tttatggcta caagtgggcg  10200
cgcgacaacg tcggccagtc gggcgcgacc atttatcggc tttatggcaa acccgatgcc  10260
ccggaactgt tcctgaagca cggcaaaggc agcgtcgcaa acgatgtcac cgatgagatg  10320
gtccgcctga actggcttac cgagttcatg ccgctgccga cgattaagca tttcatccgt  10380
accccggacg atgcctggct cttgaccacg gccattccgg gcaaaacggc ctttcaggtc  10440
cttgaagagt acccggactc cggtgagaat atcgtggacg ccctcgcggt cttcctccgc  10500
cgtttgcata gcatccccgt gtgcaactgc cccttcaact cggaccgggt tttccgcctg  10560
gcacaggccc agtcgcgcat gaataacggc ctcgttgacg cgagcgattt cgacgatgaa  10620
cggaatggct ggccggtgga acaggtttgg aaggaaatgc acaaactgct tccgttctcg  10680
ccggattcgg tggtcacgca tggtgatttt tccctggata atctgatctt tgacgagggc  10740
aagctgatcg gctgcatcga cgtgggtcgc gtcggtatcg ccgaccgcta tcaggacctg  10800
gcgatcttgt ggaattgcct cggcgagttc tcgccctcgc tccagaagcg cctgttccag  10860
aagtacggca tcgacaaccc ggatatgaac aagctccagt tccacctcat gctggacgaa  10920
tttttttgaa cagaattggt taattggttg taacactggc agagcattac gctgacttga  10980
cgggacggcg gctttgttga ataaatcgaa cttttgctga gttgaaggat cgatgagttg  11040
aaggaccccg tagaaaagat caaaggatct tcttgagatc cttttttct gcgcgtaatc   11100
tgctgcttgc aaacaaaaaa accaccgcta ccagcggtgg tttgtttgcc ggatcaagag  11160
```

-continued

```
ctaccaactc tttttccgaa ggtaactggc ttcagcagag cgcagatacc aaatactgtc  11220
cttctagtgt agccgtagtt aggccaccac ttcaagaact ctgtagcacc gcctacatac  11280
ctcgctctgc taatcctgtt accagtggct gctgccagtg gcgataagtc gtgtcttacc  11340
gggttggact caagacgata gttaccggat aaggcgcagc ggtcgggctg aacggggggt  11400
tcgtgcacac agcccagctt ggagcgaacg acctacaccg aactgagata cctacagcgt  11460
gagctatgag aaagcgccac gcttcccgaa gggagaaagg cggacaggta tccggtaagc  11520
ggcagggtcg gaacaggaga gcgcacgagg gagcttccag ggggaaacgc ctggtatctt  11580
tatagtcctg tcgggtttcg ccacctctga cttgagcgtc gatttttgtg atgctcgtca  11640
ggggggcgga gcctatggaa aaacgccagc aacgcggcct ttttacggtt cctggccttt  11700
tgctggcctt ttgctcacat gttctttcct gcgttatccc ctgattctgt ggataaccgt  11760
attaccgcct ttgagtgagc tgataccgct cgccgcagcc gaacgaccga gcgcagcgag  11820
tcagtgagcg aggaagcgga agagcgcctg atgcggtatt ttctccttac gcatctgtgc  11880
ggtatttcac accgcatagg ccgcgatagg ccgacgcgaa gcggcggggc gtagggagcg  11940
cagcgaccga agggtaggcg ctttttgcag ctcttcggct gtgcgctggc cagacagtta  12000
tgcacaggcc aggcgggttt taagagtttt aataagtttt aaagagtttt aggcggaaaa  12060
atcgcctttt ttctctttta tatcagtcac ttacatgtgt gaccggttcc caatgtacgg  12120
ctttgggttc ccaatgtacg ggttccggtt cccaatgtac ggctttgggt tcccaatgta  12180
cgtgctatcc acaggaaaga gaccttttcg accttttttcc cctgctaggg caatttgccc  12240
tagcatctgc tccgtacatt aggaaccggc ggatgcttcg ccctcgatca ggttgcggta  12300
gcgcatgact aggatcgggc cagcctgccc cgcctcctcc ttcaaatcgt actccggcag  12360
gtcatttgac ccgatcagct tgcgcacggt gaaacagaac ttcttgaact ctccggcgct  12420
gccactgcgt tcgtagatcg tcttgaacaa ccatctggct tctgccttgc ctgcggcgcg  12480
gcgtgccagg cggtagagaa aacggccgat gccggggtcg atcaaaaagt aatcggggtg  12540
aaccgtcagc acgtccgggt tcttgccttc tgtgatctcg cggtacatcc aatcagcaag  12600
ctcgatctcg atgtactccg gccgcccggt ttcgctcttt acgatcttgt agcggctaat  12660
caaggcttca ccctcggata ccgtcaccag gcggccgttc ttggccttct tggtacgctg  12720
catggcaacg tgcgtggtgt ttaaccgaat gcaggtttct accaggtcgt ctttctgctt  12780
tccgccatcg gctcgccggc agaacttgag tacgtccgca acgtgtggac ggaacacgcg  12840
gccgggcttg tctcccttcc cttcccggta tcggttcatg gattcggtta gatgggaaac  12900
cgccatcagt accaggtcgt aatcccacac actggccatg ccggcggggc ctgcggaaac  12960
ctctacgtgc ccgtctggaa gctcgtagcg gatcacctcg ccagctcgtc ggtcacgctt  13020
cgacagacgg aaaacggcca cgtccatgat gctgcgacta tcgcgggtgc ccacgtcata  13080
gagcatcgga acgaaaaaat ctggttgctc gtcgcccttg ggcggcttcc taatcgacgg  13140
cgcaccggct gccggcggtt gccgggattc tttgcggatt cgatcagcgg ccccttgcca  13200
cgattcaccg gggcgtgctt ctgcctcgat gcgttgccgc tgggcggcct gcgcggcctt  13260
caacttctcc accaggtcat cacccagcgc cgcgccgatt tgtaccgggc cggatggttt  13320
gcgaccgctc acgccgattc ctcgggcttg gggggttccag tgccattgca gggccggcag  13380
acaacccagc cgcttacgcc tggccaaccg cccgttcctc cacacatggg gcattccacg  13440
gcgtcggtgc ctggttgttc ttgattttcc atgccgcctc ctttagccgc taaaattcat  13500
ctactcattt attcatttgc tcatttactc tggtagctgc gcgatgtatt cagatagcag  13560
```

ctcggtaatg gtcttgcctt ggcgtaccgc gtacatcttc agcttggtgt gatcctccgc 13620
cggcaactga aagttgaccc gcttcatggc tggcgtgtct gccaggctgg ccaacgttgc 13680
agccttgctg ctgcgtgcgc tcggacggcc ggcacttagc gtgtttgtgc ttttgctcat 13740
tttctcttta cctcattaac tcaaatgagt tttgatttaa tttcagcggc cagcgcctgg 13800
acctcgcggg cagcgtcgcc ctcgggttct gattcaagaa cggttgtgcc ggcggcggca 13860
gtgcctgggt agctcacgcg ctgcgtgata cgggactcaa gaatgggcag ctcgtacccg 13920
gccagcgcct cggcaacctc accgccgatg cgcgtgcctt tgatcgcccg cgacacgaca 13980
aaggccgctt gtagccttcc atccgtgacc tcaatgcgct gcttaaccag ctccaccagg 14040
tcggcggtgg cccaaatgtc gtaagggctt ggctgcaccg gaatcagcac gaagtcggct 14100
gccttgatcg cggacacagc caagtccgcc gcctggggcg ctccgtcgat cactacgaag 14160
tcgcgccggc cgatggcctt cacgtcgcgg tcaatcgtcg ggcggtcgat gccgacaacg 14220
gttagcggtt gatcttcccg cacggccgcc caatcgcggg cactgccctg gggatcggaa 14280
tcgactaaca gaacatcggc cccggcgagt tgcagggcgc gggctagatg ggttgcgatg 14340
gtcgtcttgc ctgacccgcc tttctggtta agtacagcga taaccttcat gcgttcccct 14400
tgcgtatttg tttatttact catcgcatca tatacgcagc gaccgcatga cgcaagctgt 14460
tttactcaaa tacacatcac ctttttagat gatca 14495

<210> SEQ ID NO 83
<211> LENGTH: 33
<212> TYPE: DNA
<213> ORGANISM: Artificial Sequence
<220> FEATURE:
<223> OTHER INFORMATION: synthetic sequence

<400> SEQUENCE: 83
atatacgcgt ggtgcttaaa cactctggtg agt 33

<210> SEQ ID NO 84
<211> LENGTH: 38
<212> TYPE: DNA
<213> ORGANISM: Artificial Sequence
<220> FEATURE:
<223> OTHER INFORMATION: synthetic sequence

<400> SEQUENCE: 84
atatggcgcg cctttgacct acaaaatcaa agcagtca 38

<210> SEQ ID NO 85
<211> LENGTH: 32
<212> TYPE: DNA
<213> ORGANISM: Artificial Sequence
<220> FEATURE:
<223> OTHER INFORMATION: synthetic sequence

<400> SEQUENCE: 85
atatacgcgt agttctttgc tttcgaagtt gc 32

<210> SEQ ID NO 86
<211> LENGTH: 35
<212> TYPE: DNA
<213> ORGANISM: Artificial Sequence
<220> FEATURE:
<223> OTHER INFORMATION: synthetic sequence

<400> SEQUENCE: 86
atatggcgcg cctactacgt actgttttca attct 35

<210> SEQ ID NO 87
<211> LENGTH: 14065
<212> TYPE: DNA
<213> ORGANISM: Artificial Sequence
<220> FEATURE:
<223> OTHER INFORMATION: vector sequence

<400> SEQUENCE: 87
gtgattttgt gccgagctgc cggtcgggga gctgttggct ggctggtggc aggatatatt 60
gtggtgtaaa caaattgacg cttagacaac ttaataacac attgcggacg tctttaatgt 120
actgaattta gttactgatc actgattaag tactgatatc ggtaccaagc ttccgcggct 180
gcagtgcagc gtgacccggt cgtgcccctc tctagagata atgagcattg catgtctaag 240
ttataaaaaa ttaccacata ttttttttgt cacacttgtt tgaagtgcag tttatctatc 300
tttatacata tatttaaact ttactctacg aataatataa tctatagtac tacaataata 360
tcagtgtttt agagaatcat ataaatgaac agttagacat ggtctaaagg acaattgagt 420
attttgacaa caggactcta cagttttatc tttttagtgt gcatgtgttc tccttttttt 480
ttgcaaatag cttcacctat ataatacttc atccatttta ttagtacatc catttagggt 540
ttagggttaa tggtttttat agactaattt ttttagtaca tctattttat tctattttag 600
cctctaaatt aagaaaacta aaactctatt ttagtttttt tatttaatag tttagatata 660
aaatagaata aaataaagtg actaaaaatt aaacaaatac cctttaagaa attaaaaaaa 720
ctaaggaaac atttttcttg tttcgagtag ataatgccag cctgttaaac gccgtcgacg 780
agtctaacgg acaccaacca gcgaaccagc agcgtcgcgt cgggccaagc gaagcagacg 840
gcacggcatc tctgtcgctg cctctggacc cctctcgaga gttccgctcc accgttggac 900
ttgctccgct gtcggcatcc agaaattgcg tggcggagcg gcagacgtga gccggcacgg 960
caggcggcct cctcctcctc tcacggcacc ggcagctacg ggggattcct ttcccaccgc 1020
tccttcgctt tcccttcctc gcccgccgta ataaatagac accccctcca caccctcttt 1080
ccccaacctc gtgttgttcg gagcgcacac acacacaacc agatctcccc caaatccacc 1140
cgtcggcacc tccgcttcaa ggtacgccgc tcgtcctccc cccccccccc cctctctacc 1200
ttctctagat cggcgttccg gtccatggtt agggcccggt agttctactt ctgttcatgt 1260
ttgtgttaga tccgtgtttg tgttagatcc gtgctgctag cgttcgtaca cggatgcgac 1320
ctgtacgtca gacacgttct gattgctaac ttgccagtgt ttctctttgg ggaatcctgg 1380
gatggctcta gccgttccgc agacgggatc gatttcatga ttttttttgt ttcgttgcat 1440
agggtttggt ttgccctttt cctttatttc aatatatgcc gtgcacttgt ttgtcgggtc 1500
atcttttcat gctttttttt gtcttggttg tgatgatgtg gtctggttgg gcggtcgttc 1560
tagatcggag tagaattctg tttcaaacta cctggtggat ttattaattt tggatctgta 1620
tgtgtgtgcc atacatattc atagttacga attgaagatg atggatggaa atatcgatct 1680
aggataggta tacatgttga tgcgggtttt actgatgcat atacagagat gctttttgtt 1740
cgcttggttg tgatgatgtg gtgtggttgg gcggtcgttc attcgttcta gatcggagta 1800
gaatactgtt tcaaactacc tggtgtattt attaattttg gaactgtatg tgtgtgtcat 1860
acatcttcat agttacgagt ttaagatgga tggaaatatc gatctaggat aggtatacat 1920
gttgatgtgg gttttactga tgcatataca tgatggcata tgcagcatct attcatatgc 1980
tctaaccttg agtacctatc tattataata aacaagtatg ttttataatt atttcgatct 2040

```
tgatatactt ggatgatggc atatgcagca gctatatgtg gattttttta gccctgcctt   2100
catacgctat ttatttgctt ggtactgttt cttttgtcga tgctcaccct gttgtttggt   2160
gttacttctg cagcccgggg gatccactag ttctagaaac catggccacc gccgccgccg   2220
cgtctaccgc gctcactggc gccactaccg ctgcgcccaa ggcgaggcgc cgggcgcacc   2280
tcctggccac ccgccgcgcc ctcgccgcgc ccatcaggtg ctcagcggcg tcacccgcca   2340
tgccgatggc tcccccggcc accccgctcc ggccgtgggg ccccaccgat ccccgcaagg   2400
gcgccgacat cctcgtcgag tccctcgagc gctgcggcgt ccgcgacgtc ttcgcctacc   2460
ccggcggcac gtccatggag atccaccagg cactcacccg ctcccccgtc atcgccaacc   2520
acctcttccg ccacgagcaa ggggaggcct ttgcggcctc cggctacgcg cgctcctcgg   2580
gccgcgtcgg cgtctgcatc gccacctccg gccccggcgc caccaacctt gtctccgcgc   2640
tcgccgacgc gctgctcgat tccgtcccca tggtcgccat cacgggacag gtgccgcgac   2700
gcatgattgg caccgacgcc ttccaggaga cgcccatcgt cgaggtcacc cgctccatca   2760
ccaagcacaa ctacctggtc ctcgacgtcg acgacatccc ccgcgtcgtg caggaggctt   2820
tcttcctcgc ctcctctggt cgaccggggc cggtgcttgt cgacatcccc aaggacatcc   2880
agcagcagat ggcggtgcct gtctgggaca agcccatgag tctgcctggg tacattgcgc   2940
gccttcccaa gcccccctgcg actgagttgc ttgagcaggt gctgcgtctt gttggtgaat   3000
cccggcgccc tgttctttat gttggcggtg gctgcgcagc atctggtgag gagttgcgac   3060
gctttgtgga gctgactgga atcccggtca caactactct tatgggcctc ggcaacttcc   3120
ccagcgacga cccactgtct ctgcgcatgc taggtatgca tggcacggtg tatgcaaatt   3180
atgcagtgga taaggccgat ctgttgcttg cacttggtgt gcggtttgat gatcgtgtga   3240
cagggaagat tgaggctttt gcaagcaggg ctaagattgt gcacgttgat attgatccgg   3300
ctgagattgg caagaacaag cagccacatg tgtccatctg tgcagatgtt aagcttgctt   3360
tgcagggcat gaatgctctt cttgaaggaa gcacatcaaa gaagagcttt gactttggct   3420
catggaacga tgagttggat cagcagaaga gggaattccc ccttgggtat aaaacatcta   3480
atgaggagat ccagccacaa tatgctattc aggttcttga tgagctgacg aaaggcgagg   3540
ccatcatcgg cacaggtgtt gggcagcacc agatgtgggc ggcacagtac tacacttaca   3600
agcggccaag gcagtggttg tcttcagctg gtcttggggc tatgggattt ggtttgccgg   3660
ctgctgctgg tgcttctgtg gccaacccag gtgttactgt tgttgacatc gatggagatg   3720
gtagctttct catgaacgtt caggagctag ctatgatccg aattgagaac ctcccggtga   3780
aggtctttgt gctaaacaac cagcacctgg ggatggtggt gcagtgggag gacaggttct   3840
ataaggccaa cagagcgcac acatacttgg gaaacccaga gaatgaaagt gagatatatc   3900
cagatttcgt gacgatcgcc aaagggttca acattccagc ggtccgtgtg acaaagaaga   3960
acgaagtccg cgcagcgata aagaagatgc tcgagactcc agggccgtac ctcttggata   4020
taatcgtccc acaccaggag catgtgttgc ctatgatccc taatggtggg gctttcaagg   4080
atatgatcct ggatggtgat ggcaggactg tgtactgatc taaaatccag caagcaactg   4140
atctaaaatc cagcaagcac cgcctccctg ctagtacaag ggtgatatgt ttttatctgt   4200
gtgatgttct cctgtattct atcttttttt gtaggccgtc agctatctgt tatggtaatc   4260
ctatgtagct tccgaccttg taattgtgta gtctgttgtt ttccttctgg catgtgtcat   4320
aagagatcat ttaagtgcct tttgctacat ataaataaga taataagcac tgctatgcag   4380
```

```
tggttctgaa ttggcttctg ttgccaaatt taagtgtcca actggtcctt gcttttgttt   4440
tcgctatttt tttccttttt tagttattat tatattggta atttcaactc aacatatgat   4500
gtatggaata atgctagggc tgcaatttca aactatttta caaaccagaa tggcattttc   4560
gtggtttgag gggagtgaaa aaaaatgagg catttgactg aattagttac ctgatccatt   4620
ttcgtggttt ggatcattgg aattaaattc cattctaata atagtaattt tggcatatat   4680
caattaagtt aattcggttt tatgcaaaat atatttgtat actattatta tcaagatgtc   4740
ggagatattt atatgctaca tttttactat acaggagtga gatgaagagt gtcatgtaag   4800
ttacacagta gaaacaaatt ctattaatgc ataaaatcat ttccatcatc caccctatga   4860
atttgagata gacctatatc taaactttga aaagtggttg aatatcaaat tccaaattaa   4920
ataagttatt ttattgagtg aattctaatt tctctaaaac gaagggatct aaacgccctc   4980
taaagctaat ttggaaactc aaactttctt agcattggag gggattgaga aaaaatatta   5040
attcattttc atctcaatca ttcaatctcc aaagagattt gagttcctta ttagtctgtt   5100
ccatgcatca aatcggctca atgtgtcatt atttgccatg acgattgacg agttgttctg   5160
gggcctagcg ctttccacgc cgatgtgctg gggcctggtc ctggagaaga cagcttgata   5220
tttaaagcta tcaattgttt caattgattc ccacttcatt tttctaaatg tagaaaacgg   5280
tgacgtataa gaaaaagaat gaattaggac ttttattccg tacactaatc tagagcggcc   5340
caagcttgta cactagtacg cgtcaattga tttaaattta attaatcccg tgtccgtcaa   5400
tgtgatacta ctagcatagt actagtacca tgcatacaca cagcaggtcg gccgcctgga   5460
tggatcgatg atgatactac atcatcctgt catccatcca ggcgatctag aaggggcgtg   5520
gctagctagc aaactgtgac cggtttttct acgccgataa taatactttg tcatggtaca   5580
gacgtacagt actggttata tatatctgta gatttcaact gaaaagctag gatagctaga   5640
ttaattcctg agaaacacag ataaaattcg agcttggcta tagatgacaa aacggaagac   5700
gcatgcattg gacgacgtat gcaatgcgag cgcgtctcgt gtcgtcccgt ccaagtctgg   5760
cgatctcacg ccacgtgctc aacagctcaa ggactgttcg tcaccagcgt taaattcatt   5820
gaagggatga cgcatttcgg catttgtcat tgcttgtagc tatatatata tatccaacag   5880
atttctctca agcttttgta tgcgtgaatg taaagtctag cttatacgac agcacgtgca   5940
gatatattaa cgtcattatt aggtggagag caagatgcat gatctggtag aaattgtcga   6000
aaacacaaga gagagtgaag tgcacacttc tggtatagga gtgtatacgc cgctggttgg   6060
tgggcaatgc gcgccgcaat attggccaat gaaacctagc aacgcccact cgccacgccc   6120
catgaatggc ccccgcacgg cagcgagcca gccagtgccc gcgcgcggcc cagccggagt   6180
cggcggaacg cgccacgggg gacgaggcgc ccgagggccg aggcagcgcg gcatggcaag   6240
caagccgaag cgggcaagcg acctgcatgc agcccctgcc cctcgccctc gtcagtcgtc   6300
ccagcctccc actggaatcc acccaacccg cccttcctct ccaaagcacg cgccccgcga   6360
ctcgcctccg cctacgtgtc ggcagcgtcc ccgccggtcg cccacgtacc ccgccccgtt   6420
ctcccacgtg cccctccctc tgcgcgcgtc cgattggctg acccgccctt cttaagccgc   6480
gccagcctcc tgtccgggcc ccaacgccgt gctccgtcgt cgtctccgcc cccagagtga   6540
tcgagcccac tgacctggcc cccgagcctc agctcgtgag tccggcgcgt ggtgcttaaa   6600
cactctggtg agttctagta cttctgctat gatcgatctc attaccattt cttaaatttc   6660
tctccctaaa tattccgagt tcttgatttt tgataacttc aggttttctc tttttgataa   6720
atctggtctt tccatttttt tttttttgtg gttaatttag tttcctatgt tcttcgattg   6780
```

```
tattatgcat gatctgtgtt tggattctgt tagattatgt attggtgaat atgtatgtgt   6840
ttttgcatgt ctggttttgg tcttaaaaat gttcaaatct gatgatttga ttgaagcttt   6900
tttagtgttg gtttgattct tctcaaaact actgttaatt tactatcatg ttttccaact   6960
ttgattcatg atgacacttt tgttctgctt tgttataaaa ttttggttgg tttgattttg   7020
taattatagt gtaattttgt taggaatgaa catgttttaa tactctgttt tcgatttgtc   7080
acacattcga attattaatc gataatttaa ctgaaaattc atggttctag atcttgttgt   7140
catcagatta tttgtttcga taattcatca aatatgtagt ccttttgctg atttgcgact   7200
gtttcatttt ttctcaaaat tgttttttgt taagtttatc taacagttat cgttgtcaaa   7260
agtctctttc attttgcaaa atcttctttt ttttttgtt tgtaactttg tttttaagc   7320
tacacattta gtctgtaaaa tagcatcgag gaacagttgt cttagtagac ttgcatgttc   7380
ttgtaacttc tatttgtttc agtttgttga tgactgcttt gattttgtag gtcaaaggcg   7440
cgccaccatg gaagacgcca aaaacataaa gaaaggcccg gcgccattct atccgctgga   7500
agatggaacc gctggagagc aactgcataa ggctatgaag agatacgccc tggttcctgg   7560
aacaattgct tttacagatg cacatatcga ggtggacatc acttacgctg agtacttcga   7620
aatgtccgtt cggttggcag aagctatgaa acgatatggg ctgaatacaa atcacagaat   7680
cgtcgtatgc agtgaaaact ctcttcaatt ctttatgccg gtgttgggcg cgttatttat   7740
cggagttgca gttgcgcccg cgaacgacat ttataatgaa cgtgaattgc tcaacagtat   7800
gggcatttcg cagcctaccg tggtgttcgt ttccaaaaag gggttgcaaa aaattttgaa   7860
cgtgcaaaaa aagctcccaa tcatccaaaa aattattatc atggattcta aaacggatta   7920
ccagggattt cagtcgatgt acacgttcgt cacatctcat ctacctcccg gttttaatga   7980
atacgatttt gtgccagagt ccttcgatag ggacaagaca attgcactga tcatgaactc   8040
ctctggatct actggtctgc ctaaaggtgt cgctctgcct catagaactg cctgcgtgag   8100
attctcgcat gccagagatc ctatttttgg caatcaaatc attccggata ctgcgatttt   8160
aagtgttgtt ccattccatc acggttttgg aatgtttact acactcggat atttgatatg   8220
tggatttcga gtcgtcttaa tgtatagatt tgaagaagag ctgtttctga ggagccttca   8280
ggattacaag attcaaagtg cgctgctggt gccaacccta ttctccttct tcgccaaaag   8340
cactctgatt gacaaatacg atttatctaa tttacacgaa attgcttctg gtggcgctcc   8400
cctctctaag gaagtcgggg aagcggttgc caagaggttc catctgccag gtatcaggca   8460
aggatatggg ctcactgaga ctacatcagc tattctgatt acacccgagg gggatgataa   8520
accgggcgcg gtcggtaaag ttgttccatt ttttgaagcg aaggttgtgg atctggatac   8580
cgggaaaacg ctgggcgtta atcaaagagg cgaactgtgt gtgagaggtc ctatgattat   8640
gtccggttat gtaaacaatc cggaagcgac caacgccttg attgacaagg atggatggct   8700
acattctgga gacatagctt actgggacga agacgaacac ttcttcatcg ttgaccgcct   8760
gaagtctctg attaagtaca aaggctatca ggtggctccc gctgaattgg aatccatctt   8820
gctccaacac cccaacatct tcgacgcagg tgtcgcaggt cttcccgacg atgacgccgg   8880
tgaacttccc gccgccgttg ttgttttgga gcacggaaag acgatgacgg aaaaagagat   8940
cgtggattac gtcgccagtc aagtaacaac cgcgaaaaag ttgcgcggag gagttgtgtt   9000
tgtggacgaa gtaccgaaag gtcttaccgg aaaactcgac gcaagaaaaa tcagagagat   9060
cctcataaag gccaagaagg gcggaaagat cgccgtgtaa cctgcaggcc taggatcgtt   9120
```

```
caaacatttg gcaataaagt ttcttaagat tgaatcctgt tgccggtctt gcgatgatta   9180

tcatataatt tctgttgaat tacgttaagc atgtaataat taacatgtaa tgcatgacgt   9240

tatttatgag atgggttttt atgattagag tcccgcaatt atacatttaa tacgcgatag   9300

aaaacaaaat atagcgcgca aactaggata aattatcgcg cgcggtgtca tctatgttac   9360

tagatcggcc ggccgtttaa acttagttac taatcagtga tcagattgtc gtttcccgcc   9420

ttcactttaa actatcagtg tttgacagga tatattggcg ggtaaaccta agagaaaaga   9480

gcgtttatta gaataatcgg atatttaaaa gggcgtgaaa aggtttatcc gttcgtccat   9540

ttgtatgtca atattggggg ggggggaaag ccacgttgtg tctcaaaatc tctgatgtta   9600

cattgcacaa gataaaaata tatcatcatg aacaataaaa ctgtctgctt acataaacag   9660

taatacaagg ggtgttcgcc accatgagcc atatccagcg tgaaacctcg tgctcccgcc   9720

cgcgcctcaa ttccaatatg gatgccgacc tttatggcta caagtgggcg cgcgacaacg   9780

tcggccagtc gggcgcgacc atttatcggc tttatggcaa acccgatgcc ccggaactgt   9840

tcctgaagca cggcaaaggc agcgtcgcaa acgatgtcac cgatgagatg gtccgcctga   9900

actggcttac cgagttcatg ccgctgccga cgattaagca tttcatccgt accccggacg   9960

atgcctggct cttgaccacg gccattccgg gcaaaacggc ctttcaggtc cttgaagagt  10020

acccggactc cggtgagaat atcgtggacg ccctcgcggt cttcctccgc cgtttgcata  10080

gcatccccgt gtgcaactgc cccttcaact cggaccgggt tttccgcctg gcacaggccc  10140

agtcgcgcat gaataacggc ctcgttgacg cgagcgattt cgacgatgaa cggaatggct  10200

ggccggtgga acaggtttgg aaggaaatgc acaaactgct tccgttctcg ccggattcgg  10260

tggtcacgca tggtgatttt tccctggata atctgatctt tgacgagggc aagctgatcg  10320

gctgcatcga cgtgggtcgc gtcggtatcg ccgaccgcta tcaggacctg gcgatcttgt  10380

ggaattgcct cggcgagttc tcgccctcgc tccagaagcg cctgttccag aagtacggca  10440

tcgacaaccc ggatatgaac aagctccagt tccacctcat gctggacgaa tttttttgaa  10500

cagaattggt taattggttg taacactggc agagcattac gctgacttga cgggacggcg  10560

gctttgttga ataaatcgaa cttttgctga gttgaaggat cgatgagttg aaggaccccg  10620

tagaaaagat caaaggatct tcttgagatc cttttttttct gcgcgtaatc tgctgcttgc  10680

aaacaaaaaa accaccgcta ccagcggtgg tttgtttgcc ggatcaagag ctaccaactc  10740

tttttccgaa ggtaactggc ttcagcagag cgcagatacc aaatactgtc cttctagtgt  10800

agccgtagtt aggccaccac ttcaagaact ctgtagcacc gcctacatac ctcgctctgc  10860

taatcctgtt accagtggct gctgccagtg gcgataagtc gtgtcttacc gggttggact  10920

caagacgata gttaccggat aaggcgcagc ggtcgggctg aacggggggt tcgtgcacac  10980

agcccagctt ggagcgaacg acctacaccg aactgagata cctacagcgt gagctatgag  11040

aaagcgccac gcttcccgaa gggagaaagg cggacaggta tccggtaagc ggcagggtcg  11100

gaacaggaga gcgcacgagg gagcttccag ggggaaacgc ctggtatctt tatagtcctg  11160

tcgggtttcg ccacctctga cttgagcgtc gatttttgtg atgctcgtca ggggggcgga  11220

gcctatggaa aaacgccagc aacgcggcct ttttacggtt cctggccttt tgctggcctt  11280

ttgctcacat gttctttcct gcgttatccc ctgattctgt ggataaccgt attaccgcct  11340

ttgagtgagc tgataccgct cgccgcagcc gaacgaccga gcgcagcgag tcagtgagcg  11400

aggaagcgga agagcgcctg atgcggtatt ttctccttac gcatctgtgc ggtatttcac  11460

accgcatagg ccgcgatagg ccgacgcgaa gcggcggggc gtagggagcg cagcgaccga  11520
```

```
agggtaggcg ctttttgcag ctcttcggct gtgcgctggc cagacagtta tgcacaggcc  11580
aggcgggttt taagagtttt aataagtttt aaagagtttt aggcggaaaa atcgcctttt  11640
ttctctttta tatcagtcac ttacatgtgt gaccggttcc caatgtacgg ctttgggttc  11700
ccaatgtacg ggttccggtt cccaatgtac ggctttgggt tcccaatgta cgtgctatcc  11760
acaggaaaga gaccttttcg accttttttcc cctgctaggg caatttgccc tagcatctgc  11820
tccgtacatt aggaaccggc ggatgcttcg ccctcgatca ggttgcggta gcgcatgact  11880
aggatcgggc cagcctgccc cgcctcctcc ttcaaatcgt actccggcag gtcatttgac  11940
ccgatcagct tgcgcacggt gaaacagaac ttcttgaact ctccggcgct gccactgcgt  12000
tcgtagatcg tcttgaacaa ccatctggct tctgccttgc ctgcggcgcg gcgtgccagg  12060
cggtagagaa aacggccgat gccggggtcg atcaaaaagt aatcggggtg aaccgtcagc  12120
acgtccgggt tcttgccttc tgtgatctcg cggtacatcc aatcagcaag ctcgatctcg  12180
atgtactccg gccgcccggt ttcgctcttt acgatcttgt agcggctaat caaggcttca  12240
ccctcggata ccgtcaccag gcggccgttc ttggccttct tggtacgctg catggcaacg  12300
tgcgtggtgt ttaaccgaat gcaggtttct accaggtcgt ctttctgctt tccgccatcg  12360
gctcgccggc agaacttgag tacgtccgca acgtgtggac ggaacacgcg gccgggcttg  12420
tctcccttcc cttcccggta tcggttcatg gattcggtta gatgggaaac cgccatcagt  12480
accaggtcgt aatcccacac actggccatg ccggcggggc ctgcggaaac ctctacgtgc  12540
ccgtctggaa gctcgtagcg gatcacctcg ccagctcgtc ggtcacgctt cgacagacgg  12600
aaaacggcca cgtccatgat gctgcgacta tcgcgggtgc ccacgtcata gagcatcgga  12660
acgaaaaaat ctggttgctc gtcgcccttg ggcggcttcc taatcgacgg cgcaccggct  12720
gccggcggtt gccgggattc tttgcggatt cgatcagcgg ccccttgcca cgattcaccg  12780
gggcgtgctt ctgcctcgat gcgttgccgc tgggcggcct gcgcggcctt caacttctcc  12840
accaggtcat cacccagcgc cgcgccgatt tgtaccgggc cggatggttt gcgaccgctc  12900
acgccgattc ctcgggcttg gggggttccag tgccattgca gggccggcag acaacccagc  12960
cgcttacgcc tggccaaccg cccgttcctc cacacatggg gcattccacg gcgtcggtgc  13020
ctggttgttc ttgattttcc atgccgcctc ctttagccgc taaaattcat ctactcattt  13080
attcatttgc tcatttactc tggtagctgc gcgatgtatt cagatagcag ctcggtaatg  13140
gtcttgcctt ggcgtaccgc gtacatcttc agcttggtgt gatcctccgc cggcaactga  13200
aagttgaccc gcttcatggc tggcgtgtct gccaggctgg ccaacgttgc agccttgctg  13260
ctgcgtgcgc tcggacggcc ggcacttagc gtgtttgtgc ttttgctcat tttctcttta  13320
cctcattaac tcaaatgagt tttgatttaa tttcagcggc cagcgcctgg acctcgcggg  13380
cagcgtcgcc ctcgggttct gattcaagaa cggttgtgcc ggcggcggca gtgcctgggt  13440
agctcacgcg ctgcgtgata cgggactcaa gaatgggcag ctcgtacccg gccagcgcct  13500
cggcaacctc accgccgatg cgcgtgcctt tgatcgcccg cgacacgaca aaggccgctt  13560
gtagccttcc atccgtgacc tcaatgcgct gcttaaccag ctccaccagg tcggcggtgg  13620
cccaaatgtc gtaagggctt ggctgcaccg gaatcagcac gaagtcggct gccttgatcg  13680
cggacacagc caagtccgcc gcctggggcg ctccgtcgat cactacgaag tcgcgccggc  13740
cgatggcctt cacgtcgcgg tcaatcgtcg ggcggtcgat gccgacaacg gttagcggtt  13800
gatcttcccg cacggccgcc caatcgcggg cactgccctg ggatcggaa tcgactaaca  13860
```

-continued

```
gaacatcggc cccggcgagt tgcagggcgc gggctagatg ggttgcgatg gtcgtcttgc  13920

ctgacccgcc tttctggtta agtacagcga taaccttcat gcgttcccct tgcgtatttg  13980

tttatttact catcgcatca tatacgcagc gaccgcatga cgcaagctgt tttactcaaa  14040

tacacatcac ctttttagat gatca                                         14065
```